(12) United States Patent
Speier

(10) Patent No.: US 9,980,996 B2
(45) Date of Patent: *May 29, 2018

(54) PHARMACEUTICAL COMPOSITION AND METHOD OF MANUFACTURING

(71) Applicant: Gary J. Speier, Eden Prairie, MN (US)

(72) Inventor: Gary J. Speier, Eden Prairie, MN (US)

(*) Notice: Subject to any disclaimer, the term of this patent is extended or adjusted under 35 U.S.C. 154(b) by 0 days. days.

This patent is subject to a terminal disclaimer.

(21) Appl. No.: 14/694,303

(22) Filed: Apr. 23, 2015

(65) Prior Publication Data

US 2015/0297653 A1    Oct. 22, 2015

Related U.S. Application Data

(63) Continuation of application No. 14/255,296, filed on Apr. 17, 2014, now Pat. No. 9,044,390.

(51) Int. Cl.

| | |
|---|---|
| *A01N 65/00* | (2009.01) |
| *A61K 36/185* | (2006.01) |
| *A61K 9/00* | (2006.01) |
| *A61K 9/70* | (2006.01) |
| *A61K 31/352* | (2006.01) |
| *A61K 36/00* | (2006.01) |

(52) U.S. Cl.
CPC ............. *A61K 36/185* (2013.01); *A61K 9/006* (2013.01); *A61K 9/7023* (2013.01); *A61K 31/352* (2013.01); *A61K 36/00* (2013.01); *A61K 2236/37* (2013.01)

(58) Field of Classification Search
CPC ...................................................... A61K 36/00
USPC ........................................................ 424/725
See application file for complete search history.

(56) References Cited

U.S. PATENT DOCUMENTS

| | | |
|---|---|---|
| 6,241,975 B1 | 6/2001 | Moon et al. |
| 6,403,126 B1 | 6/2002 | Webster et al. |
| 6,503,532 B1 | 1/2003 | Murty |
| 6,730,330 B2 | 5/2004 | Whittle |
| 7,025,992 B2 | 4/2006 | Whittle |
| 7,344,736 B2 | 3/2008 | Whittle et al. |
| 7,622,140 B2 | 11/2009 | Whittle et al. |
| 7,722,904 B2 | 5/2010 | Schneider et al. |
| 8,029,831 B2 | 10/2011 | Pacioretty |
| 8,048,456 B2 | 11/2011 | Burke-Colvin et al. |
| 8,501,250 B2 | 8/2013 | Ismail et al. |
| 8,535,740 B2 | 9/2013 | Babish et al. |
| 2002/0136752 A1 | 9/2002 | Whittle |
| 2003/0021752 A1 | 1/2003 | Whittle |
| 2003/0206974 A1 | 11/2003 | Ilic et al. |
| 2004/0033280 A1 | 2/2004 | Whittle |
| 2004/0147767 A1 | 7/2004 | Whittle et al. |
| 2004/0192760 A1 | 9/2004 | Whittle et al. |
| 2008/0103193 A1 | 5/2008 | Castor et al. |
| 2008/0167483 A1 | 7/2008 | Whittle et al. |
| 2008/0262099 A1 | 10/2008 | Whittle et al. |
| 2009/0068291 A1 | 3/2009 | Cyr |
| 2009/0117211 A1 | 5/2009 | Schneider et al. |
| 2010/0119606 A1 | 5/2010 | Whittle et al. |
| 2011/0052737 A1 | 3/2011 | Florence et al. |
| 2011/0064832 A1 | 3/2011 | Burke-Colvin et al. |
| 2011/0076346 A1 | 3/2011 | Babish et al. |
| 2011/0217753 A1 | 9/2011 | Cyr |
| 2011/0244060 A1 | 10/2011 | Ismail et al. |
| 2012/0046366 A1 | 2/2012 | Ismail |
| 2012/0225136 A1 | 9/2012 | Whittle |
| 2013/0253210 A1 | 9/2013 | Ismail et al. |
| 2013/0316432 A1 | 11/2013 | Cyr |
| 2014/0248379 A1 | 9/2014 | Mueller |

FOREIGN PATENT DOCUMENTS

| | | |
|---|---|---|
| EP | 1802274 B1 | 9/2008 |
| EP | 2286793 A2 | 2/2011 |
| EP | 2292211 A2 | 3/2011 |
| EP | 2298283 A2 | 3/2011 |
| EP | 2298284 A2 | 3/2011 |
| EP | 2311475 A2 | 4/2011 |
| EP | 1385595 B1 | 5/2012 |
| EP | 1536810 B1 | 8/2012 |
| EP | 2524695 A1 | 11/2012 |
| EP | 1361864 B1 | 12/2013 |
| WO | WO-02024145 A2 | 3/2002 |
| WO | WO-02064109 A2 | 8/2002 |
| WO | WO-02089945 A2 | 11/2002 |
| WO | WO-2004016277 A2 | 2/2004 |
| WO | WO-2006037981 A1 | 4/2006 |
| WO | WO-2010004355 A2 | 1/2010 |
| WO | WO-201050794 A1 | 5/2010 |
| WO | WO-2010064891 A1 | 6/2010 |
| WO | WO-2010150245 A1 | 12/2010 |

(Continued)

OTHER PUBLICATIONS

"U.S. Appl. No. 14/255,296, Notice of Allowance mailed Feb. 27, 2015", 12 pgs.

(Continued)

*Primary Examiner* — Michael Meller
(74) *Attorney, Agent, or Firm* — Gary J. Speier

(57) ABSTRACT

The present invention provides for methods of obtaining an extract of *Cannabis* plant material as well as subsequent processing of the extract to provide a concentrate of *Cannabis*. The present invention also provides for pharmaceutical dosage forms (e.g., oral thin films and transdermal patches) that include the concentrate (or extract) of *Cannabis*, as well as methods of medical treatment that include administering the pharmaceutical dosage forms.

20 Claims, No Drawings

(56) References Cited

FOREIGN PATENT DOCUMENTS

WO  WO-2011083397 A1  7/2011
WO  WO-2011083398 A2  7/2011

OTHER PUBLICATIONS

"U.S. Appl. No. 14/255,296, PTO Response to Rule 312 Commnication mailed Apr. 15, 2015", 2 pgs.
"U.S. Appl. No. 14/255,296, Response filed Jan. 28, 2015 go Restriction Requirement mailed Jan. 15, 2015", 9 pgs.
"U.S. Appl. No. 14/255,296, Restriction Requirement mailed Mar. 16, 2015", 9 pgs.

PHARMACEUTICAL COMPOSITION AND METHOD OF MANUFACTURING

CLAIM OF PRIORITY

This patent application is a Continuation of U.S. patent application Ser. No. 14/255,296, filed Apr. 17, 2014, and is incorporated by reference herein.

BACKGROUND

The medicinal and psychoactive properties of the *Cannabis* plant have been known for centuries. At present, *Cannabis* is not legally available in many States. However, there is growing pressure on politicians to legalize its use, especially for medicinal purposes.

Evidence suggests that *Cannabis* is a safe, versatile and potentially inexpensive drug. It has been reported as being beneficial to patients suffering from a wide range of symptoms experienced in connection with various, often very serious, medical conditions. For example, *Cannabis* has been used to alleviate symptoms associated with cancer, anorexia, AIDS, chronic pain, spacicity, glaucoma, arthritis, migraine and many other illnesses.

*Cannabis* is recognized as having anti-emetic properties and has been successfully used to treat nausea and vomiting in cancer patients undergoing chemotherapy.

Studies also report use of *Cannabis* in treating the weight loss syndrome of AIDS and in reducing intraocular pressure for the treatment of glaucoma. *Cannabis* is also reported to have muscle relaxing effects and anti-convulsant effects.

However, it is also well documented that these medicinal effects of *Cannabis* come at the cost of less desirable effects. It is alleged that the administration of *Cannabis* causes changes in mood, perception and motivation. The common euphoric effects have led to the use of *Cannabis* as a recreational, "soft" drug and its criminalization. The psychoactive effects are said to vary with dose, with the typical *Cannabis* smoker experiencing a "high" which lasts about 2 hours, during which there is impairment of cognitive functions, perception, reaction time, learning and memory. These side effects clearly have implications, such as for the operation of machinery, and in particular for driving. These effects also make *Cannabis* less attractive for widespread, mainstream use, as it can reduce a patient's ability to perform relatively simple tasks during treatment.

The euphoric effects of *Cannabis* may also constitute an undesirable side effect for patients using the drug for medicinal purposes, especially for "naive" *Cannabis* users. Furthermore, here have been reports of unpleasant reactions to *Cannabis*, such as anxiety, panic or hallucinations. It is believed that these undesirable effects are most commonly associated with higher doses of *Cannabis*.

Despite these effects, years of research have failed to show that *Cannabis* is dangerous. In fact, the results appear to have proved the opposite. *Cannabis* has been shown to be safer, with fewer serious side effects than most prescription drugs currently used as anti-emetics, muscle relaxants, hypnotics and analgesics, etc.

The physiological and pharmacological effects of *Cannabis* depend upon a number of factors, including the dosage level and the route of administration.

There are currently two main methods of *Cannabis* delivery. Lung delivery is most commonly achieved by smoking *Cannabis*. Unfortunately, there are concerns about the effect of this mode of administration on the lungs. *Cannabis* smoke carries even more tars and other particulate matter than tobacco, and so may be a cause of lung cancer. Furthermore, many patients find the act of smoking unappealing, as well as generally unhealthy. It is known that some of the chemicals produced by smoking *Cannabis* are aggressive and smoking has been shown to cause the gradual dissolving of teeth. Use of vaporizers for inhalation administration of *Cannabis* does not avoid the production of thermal byproducts, and also can produce tracheal and lung irritation. For these reasons, smoking is not an approved medical means of administration for any drug.

Attempts have been made to overcome some of the problems associated with smoking both *Cannabis* and tobacco by providing various smokeless inhalable aerosol formulations for lung delivery. A self-propelled inhalable aerosol of delta-9-tetrahydrocannabinol was developed as long ago as 1975 as a bronchodilator. Inhalable aerosol formulations were made comprising either only liquid components and or including a solid particulate component carrying the active agent, such as the *Cannabis*. The various formulations were found to be of varying effectiveness in delivering the active agent to the alveoli of the lungs in the same manner as smoke.

However, both methods of lung delivery discussed above have been found to cause a pronounced and involuntary cough, possibly from irritation of the trachea and lungs. This unpleasant side effect is not overcome by the smoke-free method of lung delivery.

An oral dosage form of *Cannabis* is available in the United States as a Schedule II drug. The capsules contain a synthetic version of delta-9-tetrahydrocannabinol (delta-9-THC), the main active substance in *Cannabis*, and they have had limited success for a number of reasons. Firstly, in light of its anti-emetic properties, the capsules are commonly used to treat nausea and vomiting. Clearly, an oral administration is not ideal as the patient may well have difficulty keeping the capsule down long enough for it to take effect. It has also been found that orally administered THC is erratically and slowly absorbed into the bloodstream, making the dose and duration of action difficult to control. Furthermore, the oral dose is less effective than smoked *Cannabis* and therefore larger doses are required in order to achieve a desired therapeutic effect.

SUMMARY

The present invention provides for a process for obtaining an extract of *Cannabis*. The process includes: (a) contacting *Cannabis* plant material with a supercritical fluid solvent system at a pressure between about 750 psi and 25,000 psi, and at a temperature between about −15° C. and 200° C., to provide an extract of *Cannabis*; and (b) optionally removing the supercritical fluid solvent system from the extract of *Cannabis* to provide a concentrate of *Cannabis*.

The present invention provides for an additional process for obtaining an extract of *Cannabis*. The process includes: (a) contacting *Cannabis* plant material with a supercritical fluid solvent system at a pressure between about 750 psi and 25,000 psi, and at a temperature between about −15° C. and 200° C., to provide an extract of *Cannabis* and an extracted *Cannabis* plant material; (b) removing the supercritical fluid solvent system from the extract of *Cannabis* to provide a concentrate of *Cannabis*; (c) contacting the extracted *Cannabis* plant material with a second supercritical fluid solvent system at a pressure between about 750 psi and 25,000 psi, and at a temperature between about −15° C. and 200° C., to provide a second extract of *Cannabis* and a second extracted *Cannabis* plant material; and (d) optionally removing the second supercritical fluid solvent system from the second extract of *Cannabis* to provide a second concentrate of *Cannabis*.

The present invention provides for an additional process for obtaining an extract of *Cannabis*. The process includes: (a) contacting *Cannabis* plant material with a supercritical fluid solvent system at a pressure between about 750 psi and 25,000 psi, and at a temperature between about −15° C. and 200° C., to provide an extract of *Cannabis* and an extracted *Cannabis* plant material; (b) removing the supercritical fluid solvent system from the extract of *Cannabis* to provide a concentrate of *Cannabis*; (c) contacting the extracted *Cannabis* plant material with a second supercritical fluid solvent system at a pressure between about 750 psi and 25,000 psi, and at a temperature between about −15° C. and 200° C., to provide a second extract of *Cannabis* and a second extracted *Cannabis* plant material; (d) removing the second supercritical fluid solvent system from the second extract of *Cannabis* to provide a second concentrate of *Cannabis*; (e) contacting the second extracted *Cannabis* plant material with a third supercritical fluid solvent system at a pressure between about 750 psi and 25,000 psi, and at a temperature between about −15° C. and 200° C., to provide a third extract of *Cannabis* and a third extracted *Cannabis* plant material; and (f) optionally removing the third supercritical fluid solvent system from the third extract of *Cannabis* to provide a third concentrate of *Cannabis*.

The present invention provides for an additional process for obtaining an extract of *Cannabis*. The process includes: (a) contacting *Cannabis* plant material with a supercritical fluid solvent system at a pressure between about 750 psi and 25,000 psi, and at a temperature between about −15° C. and 200° C., to provide an extract of *Cannabis* and an extracted *Cannabis* plant material; (b) removing the supercritical fluid solvent system from the extract of *Cannabis* to provide a concentrate of *Cannabis*; (c) contacting the extracted *Cannabis* plant material with a second supercritical fluid solvent system at a pressure between about 750 psi and 25,000 psi, and at a temperature between about −15° C. and 200° C., to provide a second extract of *Cannabis* and a second extracted *Cannabis* plant material; (d) removing the second supercritical fluid solvent system from the second extract of *Cannabis* to provide a second concentrate of *Cannabis*; (e) contacting the second extracted *Cannabis* plant material with a third supercritical fluid solvent system at a pressure between about 750 psi and 25,000 psi, and at a temperature between about −15° C. and 200° C., to provide a third extract of *Cannabis* and a third extracted *Cannabis* plant material; (f) removing the third supercritical fluid solvent system from the third extract of *Cannabis* to provide a third concentrate of *Cannabis*; (g) contacting the third extracted *Cannabis* plant material with a fourth supercritical fluid solvent system at a pressure between about 750 psi and 25,000 psi, and at a temperature between about −15° C. and 200° C., to provide a fourth extract of *Cannabis* and a fourth extracted *Cannabis* plant material; and (h) optionally removing the fourth supercritical fluid solvent system from the fourth extract of *Cannabis* to provide a fourth concentrate of *Cannabis*.

The present invention provides for an additional process for obtaining a concentrate of *Cannabis*. The process includes: (a) contacting *Cannabis* plant material with a supercritical fluid solvent system, at a pressure between about 750 psi and 25,000 psi, and at a temperature between about −15° C. and 200° C., to provide an extract of *Cannabis*; and (b) removing the supercritical fluid solvent system from the extract. The (a) contacting of the *Cannabis* plant material with the supercritical fluid solvent system and the (b) removing the supercritical fluid solvent system, is carried out multiple times, such that the process may be a fractional supercritical fluid extraction. Additionally, each contacting of the *Cannabis* plant material with a supercritical fluid solvent system independently occurs at a pressure between about 750 psi and 25,000 psi, and independently occurs at a temperature between about −15° C. and 200° C.

The present invention also provides a pharmaceutical dosage form, which can be an oral thin film (OTF) suitable for oral delivery, or an adhesive topical patch suitable for transdermal delivery. The pharmaceutical dosage form includes a *Cannabis* concentrate including at least one of cannabinol (CBN); cannabinolic acid (CBNA); Δ(9)-tetrahydrocannabinol (Δ(9)-THC); Δ(9)-tetrahydrocannabinolic acid (Δ(9)-THCA); Δ(9)-cannabidiol (Δ(9)-CBD); Δ(9)-tetrahydrocannabidiolic acid (Δ(9)-CBDA); Δ(8)-tetrahydrocannabinol (Δ(8)-THC); Δ(8)-tetrahydrocannabinolic acid (Δ(8)-THCA); Δ(8)-tetrahydrocannabidiol (Δ(8)-CBD); Δ(8)-tetrahydrocannabidiolic acid (Δ(8)-CBDA); Δ(9)-tetrahydrocannabivarin (Δ(9)-THV); cannabigerol (CBG); cannabigerolic acid (CBGA); cannabichromene (CBC); cannabichromenic acid (CBCA); cannabicyclol (CBL); cannabicyclolic acid (CBLA); β-caryophyllene epoxide; mentha-1,8(9)-dien-5-ol; pulegone; limonene; limonene oxide; α-terpinene; terpinen-4-ol; carvacrol; carvone; 1,8-cineole; p-cymene; fenchone; pulegone-1,2epoxide; β-myrcene; cannaflavin A; and cannaflavin B.

The present invention provides a method of treating a mammal afflicted with a disease or disorder. The method includes administering to a mammal in need of such treatment, the pharmaceutical dosage form described herein, in an amount and for a period of time, effective to treat the disease or disorder.

In various embodiments of the present invention, the methods of manufacturing described herein employ supercritical fluid extraction (SFE) to provide an extract of *Cannabis*. The solvent can conveniently be removed from the extract, to provide a concentrate (or an essential) of *Cannabis*. When the SFE is a fractional supercritical fluid extraction (FSFE), the desired extract of *Cannabis* can include, e.g., cannabinoids, terpenoids, and/or flavonoids. In various embodiments, the desired extract of *Cannabis* (relative to the starting plant material) will be enriched with the desired product (e.g. cannabinoids, terpenoids, and/or flavonoids). In further embodiments, the desired extract of *Cannabis* (relative to the undesired extract of *Cannabis*) will be enriched with the desired product (e.g. cannabinoids, terpenoids, and/or flavonoids). In yet further embodiments, the undesired extract of *Cannabis* (relative to the desired extract of *Cannabis*) will be enriched with the undesired product (e.g. terpenes, alkaloids, hemp oil, and/or cannabinoid acids). As such, the FSFE can be employed to selectively obtain one or more desired substances from the *Cannabis* plant material, while selectively excluding one or more undesired substances.

In other embodiments, purified fractions enriched in certain of the *Cannabis* components listed herein relative to other of the *Cannabis* components, can be prepared by a method of the invention. For instance, fractions enriched in certain cannabinoids relative to other cannbinoids, compared to proportions as occurring in the *Cannabis* plant material that is extracted, can be obtained by practice of a method of the invention. In this way, enriched purified fractions of *Cannabis* extract can be obtained, which can offer therapeutic benefits to a patient receiving treatment thereby.

While the concentrate (or essential oil) of *Cannabis* can conveniently be obtained from the desired extract of *Cannabis* upon removal of the solvent, the concentrate, or a SFE-purified fraction thereof, can subsequently be further purified by standard purification techniques. Alternatively, the concentrate, or a SFE-purified fraction thereof, or a further purified fraction thereof, can be used directly in a pharmaceutical dosage form (e.g., transdermal patch or oral thin film) without any further purification.

Transdermal patches typically include one or more adhesives positioned on the surface of the backing that contacts the user when used. The *Cannabis* concentrate, or a SFE-purified fraction thereof, or a further purified fraction thereof, can conveniently be used directly in the manufacture of a transdermal patch, e.g., by mixing the concentrate with the one or more adhesives. This will avoid the necessity to dissolve any active pharmaceutical ingredient in the adhesive layer of the transdermal patch. This may also assist in avoiding issues that may otherwise exist with a high load of desired compounds present in *Cannabis* (e.g. cannabinoids, terpenoids, and/or flavonoids) in the transdermal patch. The *Cannabis* concentrate can be used directly from the *Cannabis* extract (e.g., upon removal of the supercritical fluid solvent), or alternatively can first be purified, e.g., by SFE fractionation, or by standard purification techniques, or by a combination thereof, and then employed in the manufacture of the topical patch.

Likewise, the manufacture of an oral thin film (OTF) typically includes the casting and drying of a viscous liquid (or slurry). The *Cannabis* concentrate, or a SFE-purified fraction thereof, or a further purified fraction thereof, can be used directly in the manufacture of an OTF, e.g., by mixing the concentrate with the viscous liquid. This will avoid the necessity to dissolve any active pharmaceutical ingredient in the viscous liquid prior to drying. As such, the concentrate can conveniently be used directly in the manufacture of an OTF. This may also assist in avoiding issues that may otherwise exist with a high load of desired compounds present in *Cannabis* (e.g. cannabinoids, terpenoids, and/or flavonoids) into an OTF. The *Cannabis* concentrate can be used directly from the *Cannabis* extract (e.g., upon removal of the supercritical fluid solvent), or alternatively can first be purified, e.g., by SFE fractionation, or by standard purification techniques such as chromatography, or by a combination thereof, and then employed in the manufacture of the OTF.

In specific embodiments, advantages of a transdermal drug delivery route over other types of medication delivery such as oral, topical, intravenous, intramuscular, etc. is that the patch provides a controlled release of the medication into the patient, usually through either a porous membrane covering a reservoir of medication or through body heat melting thin layers of medication embedded in the adhesive. The fact that the transdermal patch can provide a controlled release of medication for up to seven days gives it a major advantage over other types of drug delivery, such as oral or other types of topical administration (for example, gels or creams).

The delivery of a drug via a transdermal route of application can offer the best of oral and intravenous administration. Avoidance of the first-pass effect leads to better bioavailability and may result in fewer side effects. Consistent and controlled drug delivery avoids periods of under- and overdosing. Transdermal patches deliver drugs over a longer period of time, thus allowing for reduced dosing frequency. A transdermal patch is administered by the patients themselves and administration is stopped by removal of the patch. Contrary to intravenous drips or infusion pumps, patient activity is not restricted. These numerous benefits lead to significantly improved patient compliance and as a consequence transdermal patches can offer a critical edge to new and established drugs in competitive markets.

Both transdermal patches as well as oral thin films (OTFs) serve as an alternative dosage form for patients who experience dysphagia (difficulty in swallowing). Additional reasons to use transdermal patches and/or OTFs include the convenience of a dosage form that can be taken without water as well as the inability of the patient to eat or drink (e.g., nausea and/or vomiting). Additional reasons to use transdermal patches and/or OTFs with any substance derived from a plant material that is typically inhaled, includes the avoidance of smoke and carcinogenic constituents in the smoke, both with the primary user as well as individuals in close proximity (e.g., second-hand smoke).

In specific embodiments, advantages of OTFs include the potential to improve the onset of action, lower the dosing, and enhance the efficacy and safety profile of the medicament. All tablet dosage forms, softgels and liquid formulations primarily enter the blood stream via the gastrointestinal tract, which subjects the drug to degradation from stomach acid, bile, digestive enzymes and other first-pass effects. As a result, such formulations often require higher doses and generally have a delayed onset of action. Conversely, buccal and sublingual OTF drug delivery can avoid these issues and yield quicker onsets of action at lower doses.

In specific embodiments, advantages of OTFs include the thin film is typically more stable, durable and quicker dissolving than many other conventional dosage forms.

In specific embodiments, advantages of OTFs include the thin film enables improved dosing accuracy relative to liquid formulations since every strip is manufactured to contain a precise amount of the drug.

In specific embodiments, advantages of OTFs include the thin film not only ensures more accurate administration of drugs but also can improve compliance due to the intuitive nature of the dosage form and its inherent ease of administration. These properties are especially beneficial for pediatric, geriatric and neurodegenerative disease patients where proper and complete dosing can be difficult.

In specific embodiments, advantages of OTFs include the thin film's ability to dissolve rapidly without the need for water provides an alternative to patients with swallowing disorders and to patients suffering from nausea, such as those patients receiving chemotherapy.

In specific embodiments, advantages of OTFs include the thin film drug delivery has the potential to allow the development of sensitive drug targets that may otherwise not be possible in tablet or liquid formulations.

In specific embodiments, advantages of OTFs include the ability of a sublingual film to deliver a convenient, quick-dissolving therapeutic dose contained within an abuse-deterrent film matrix that cannot be crushed or injected by patients, and rapidly absorbs under the tongue to ensure compliance.

In specific embodiments, advantages of OTFs include the ability of the thin film to facilitate absorption (e.g., 3 to 10 times) greater than an oral tablet. This includes, e.g., sublingual administration under the tongue.

In specific embodiments, advantages of employing a *Cannabis* concentrate into an OTF or topical adhesive patch include the ease and convenience in using a non-solid (e.g., liquid, tar, oil, syrup, etc.) *Cannabis* concentrate, which may otherwise be problematic in formulating, e.g., capsules, pills and tablets. In further embodiments, additional advantages include the ease and convenience in using a *Cannabis* concentrate without the need for subsequent purification.

Additional advantages include the ability to use the *Cannabis* extract (which may include a significant and/or appreciable amount of organic solvent), without subsequent removal of the solvent, prior to use in manufacturing the OTF or topical adhesive patch. In such embodiments, the presence of the solvent will not pose any significant issues or concerns in producing the OTF or topical adhesive patch, and in some situations may aid in maintaining the solubility of the desired compounds in the *Cannabis* concentrate, which is used directly in the OTF or topical adhesive patch.

DETAILED DESCRIPTION

Reference will now be made in detail to certain claims of the invention, examples of which are illustrated in the accompanying drawings. While the invention will be described in conjunction with the enumerated claims, it will be understood that they are not intended to limit those claims. On the contrary, the invention is intended to cover all alternatives, modifications, and equivalents, which can be included within the scope of the invention as defined by the claims.

References in the specification to "one embodiment," "an embodiment," "an example embodiment," and the like, indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one of ordinary skill in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods or processes described herein, the steps can be carried out in any order without departing from the principles of the invention, except when a temporal or operational sequence is explicitly recited.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

As used herein, "*Cannabis*" refers to a genus of flowering plants that includes a single species, *Cannabis sativa*, which is sometimes divided into two additional species, *Cannabis indica* and *Cannabis ruderalis*. These three taxa are indigenous to Central Asia, and South Asia. *Cannabis* has long been used for fiber (hemp), for seed and seed oils, for medicinal purposes, and as a recreational drug. Various extracts including hashish and hash oil are also produced from the plant. Suitable strains of *Cannabis* include, e.g., Indica-dominant (e.g., Blueberry, BC Bud, Holland's Hope, Kush, Northern Lights, Purple, and White Widow), Pure sativa (e.g., Acapulco Gold and Malawi Gold (Chamba)), and Sativa-dominant (e.g., Charlotte's Web, Diesel, Haze, Jack Herer, Shaman, Skunk, Sour, and Te Puke Thunder). The *Cannabis* can include any physical part of the plant material, including, e.g., the leaf, bud, flower, trichome, seed, or combination thereof. Likewise, the *Cannabis* can include any substance physically derived from *Cannabis* plant material, such as, e.g., kief and hashish.

As used herein, "kief" refers to the resin glands (or trichomes) of *Cannabis* which may accumulate in containers or be sifted from loose dry *Cannabis* flower with a mesh screen or sieve. Kief typically contains a much higher concentration of psychoactive cannabinoids, such as THC, than that of the *Cannabis* flowers from which it is derived. Traditionally, kief has been pressed into cakes of hashish for convenience in storage, but can be vaporized or smoked in either form.

As used herein, "hashish" refers to a *Cannabis* product composed of compressed or purified preparations of stalked resin glands, called trichomes. It contains the same active ingredients—such as THC and other cannabinoids—but in higher concentrations than unsifted buds or leaves.

As used herein, "leaf" refers to an organ of a vascular plant, as defined in botanical terms, and in particular, in plant morphology. In reference to *Cannabis*, the first pair of leaves usually have a single leaflet, the number gradually increasing up to a maximum of about thirteen leaflets per leaf (usually seven or nine), depending on variety and growing conditions. At the top of a flowering plant, this number again diminishes to a single leaflet per leaf. The lower leaf pairs usually occur in an opposite leaf arrangement and the upper leaf pairs in an alternate arrangement on the main stem of a mature plant.

As used herein, "bud" refers to a flower-bearing stem or branch of the *Cannabis* plant, especially a stem or branch bearing a mass of female flowers with associated leaves. The stem or branch bearing the female flowers can be fresh, or can be dried. The pistils of the female *Cannabis* flower are surrounded by a mass of trichome-rich petals and leaves, and can contain higher concentrations of cannabinoids than do the plant leaves or stems. A bud, e.g., a mass of female flowers and associated leaves, usually covered with trichomes, can be further processed mechanically, i.e., "trimming" or "cleaning" the stem bearing the female flowers by removal of larger leaves and stem material. Buds, and cleaned buds, can be used as a *Cannabis* plant material in practice of a method of the invention.

As used herein, "trichome" refers to a fine outgrowth or appendage on plants and certain protists. They are of diverse structure and function. Examples are hairs, glandular hairs, scales, and papillae. In reference to *Cannabis*, the trichome is a glandular trichome that occurs most abundantly on the floral calyxes and bracts of female plants.

As used herein, "seed" refers to an embryonic plant enclosed in a protective outer covering called the seed coat, usually with some stored food. It is a characteristic of spermatophytes (gymnosperm and angiosperm plants) and the product of the ripened ovule which occurs after fertilization and some growth within the mother plant. The formation of the seed completes the process of reproduction in seed plants (started with the development of flowers and pollination), with the embryo developed from the zygote and the seed coat from the integuments of the ovule.

As used herein, "*Cannabis sativa* L." or "*Cannabis sativa*" refers to an annual herbaceous plant in the *Cannabis* genus, a species of the Cannabaceae family.

As used herein, "*Cannabis indica* Lam" or "*Cannabis indica*" refers to an annual plant in the Cannabaceae family. A putative species of the genus *Cannabis*, it is typically distinguished from *Cannabis sativa*. *Cannabis sativa* and *Cannabis indica* can interbreed, so the two strains can be viewed as sub-species or land races. Interbred stains comprising genetic material from both sativa and indica strains can be termed "sativa-dominant" or "indica-dominant", depending upon perceived physical and psychotropic properties of the hydbrids. The mixed interbred strains can be themselves reproductively viable.

As used herein, "*Cannabis ruderalis* Janisch" or "*Cannabis ruderalis*" refers to a species of *Cannabis* originating in central Russia. It flowers earlier than *C. indica* or *C. sativa*, does not grow as tall, and can withstand much harsher climates than either of them. *Cannabis ruderalis* will produce flowers based on its age, rather than light cycle (photoperiod) changes which govern flowering in *C. sativa* and *C. indica* varieties. This kind of flowering is also known as "autoflowering."

The *Cannabis* plant material contains suitable and desirable compounds, useful in the pharmaceutical dosage forms and methods of medical treatment described herein. The suitable and desirable compounds fall within one or more the following classes of compounds: cannabinoids, terpenoids, and flavonoids. These compounds can be obtained from the *Cannabis* in a pure or partially pure state. The compounds obtained from the *Cannabis* can be in the form of an extract of *Cannabis*, or a concentrate of *Cannabis*.

As used herein, "extract" refers to a substance obtained by extracting a raw material, using a solvent system. The term "extract of *Cannabis*" refers to a substance obtained by extracting *Cannabis* (or any part thereof). In specific embodiments, the process of extracting a raw material using a solvent includes a hot solvent extraction. In alternative embodiments, the process of extracting a raw material using a solvent includes supercritical fluid extraction (SFE), such as, e.g., a fractional supercritical fluid extraction (FSFE). In reference to *Cannabis*, suitable extracts include, e.g., hash oil, tincture, or combination thereof.

In specific embodiments, the extract of *Cannabis* fulfils the definition of "botanical drug substance" provided in the Guidance for Industry Botanical Drug Products Draft Guidance, August 2000, US Department of Health and Human Services, Food and Drug Administration Center for Drug Evaluation and Research of: "A drug substance derived from one or more plants, algae, or macroscopic fungi. It is prepared from botanical raw materials by one or more of the following processes: pulverization, decoction, expression, aqueous extraction, ethanolic extraction, or other similar processes."

As used herein, "tincture" refers to a solvent extract of plant or animal material, a solution of such, or of a low volatility substance.

As used herein, "hash oil" refers to a form of *Cannabis*. It is a resinous matrix of cannabinoids obtained from the *Cannabis* plant by solvent extraction, formed into a hardened or viscous mass. Hash oil can be the most potent of the main *Cannabis* products because of its high THC content which can vary depending on the plant.

As used herein, "concentrate" or "essential oil" refers to a substance obtained by extracting a raw material, using a solvent, wherein the solvent has substantially been removed. In specific embodiments, the process of extracting a raw material using a solvent includes a hot solvent extraction. In alternative embodiments, the process of extracting a raw material using a solvent includes supercritical fluid extraction (SFE), such as, e.g., a fractional supercritical fluid extraction (FSFE).

As such, the term "*Cannabis* concentrate" or "*Cannabis* essential oil" refers to a substance obtained by extracting *Cannabis* (or any part thereof), wherein the solvent has substantially been removed. The *Cannabis* concentrate can be enriched with the desired product (e.g. cannabinoids, terpenoids, and/or flavonoids) from the *Cannabis* plant material. Additionally, compared to the *Cannabis* plant material, the *Cannabis* concentrate can contain a lower concentration of unwanted material (e.g. terpenes, alkaloids, hemp oil, and/or cannabinoid acids).

As used herein, "cannabinoid" refers to a class of diverse chemical compounds that act on cannabinoid receptors on cells that repress neurotransmitter release in the brain. These receptor proteins include the endocannabinoids (produced naturally in the body by humans and animals), the phytocannabinoids (found in *Cannabis* and some other plants), and synthetic cannabinoids (manufactured chemically). The most notable cannabinoid is the phytocannabinoid Δ9-tetrahydrocannabinol (THC), the primary psychoactive compound of *Cannabis*. Cannabidiol (CBD) is another major constituent of the plant, representing up to 40% in extracts of the plant resin. There are at least 85 different cannabinoids isolated from *Cannabis*, exhibiting varied effects.

As used herein, "terpenoid" or "isoprenoid" refers to a large and diverse class of naturally occurring organic chemicals similar to terpenes, derived from five-carbon isoprene units assembled and modified in thousands of ways. Most are multicyclic structures that differ from one another not only in functional groups but also in their basic carbon skeletons. These lipids can be found in all classes of living things, and are the largest group of natural products. Plant terpenoids are used extensively for their aromatic qualities. They play a role in traditional herbal remedies and are under investigation for antibacterial, antineoplastic, and other pharmaceutical functions. Terpenoids contribute to the scent of eucalyptus, the flavors of cinnamon, cloves, and ginger, the yellow color in sunflowers, and the red color in tomatoes. Well-known terpenoids include citral, menthol, camphor, salvinorin A in the plant *Salvia divinorum*, the cannabinoids found in *Cannabis*, ginkgolide and bilobalide found in *Ginkgo biloba*, and the curcuminoids found in turmeric and mustard seed.

As used herein, "flavonoid" refers to a class of plant secondary metabolites. Flavonoids were referred to as Vitamin P (probably because of the effect they had on the permeability of vascular capillaries) from the mid-1930s to early 50s, but the term has since fallen out of use. According to the IUPAC nomenclature, they can be classified into: flavonoids or bioflavonoids; isoflavonoids, derived from 3-phenylchromen-4-one (3-phenyl-1,4-benzopyrone) structure; and neoflavonoids, derived from 4-phenylcoumarine (4-phenyl-1,2-benzopyrone) structure.

As used herein, "supercritical fluid extraction" or "SFE" refers to the process of separating one or more components (extractant) from another (matrix) using supercritical fluids as the extracting solvent. Extraction is usually from a solid matrix (e.g., *Cannabis* plant material), but can also be from liquids or resinous material (e.g., hash oil). SFE can be used as a sample preparation step for analytical purposes, or on a larger scale to either strip unwanted material from a product (e.g. terpenes, alkaloids, hemp oil, and/or cannabinoid acids from *Cannabis* plant material) and/or collect a desired product (e.g. cannabinoids, terpenoids, and/or flavonoids). Although numerous supercritical fluids can be used, carbon dioxide ($CO_2$) is the most used supercritical fluid, sometimes modified by co-solvents such as ethanol or methanol. Extraction conditions for supercritical fluids are above the critical temperature of (e.g., 31° C. for carbon dioxide) and critical pressure of (e.g., 74 bar for carbon dioxide). Addition of modifiers may slightly alter this.

The properties of a supercritical fluid can be altered by varying the pressure and temperature, allowing selective extraction. For example, various substances can be extracted from a plant with low pressures (e.g., 100 bar), whereas extraction from the same plant (and same solvent system) with high pressure (e.g., 750 bar) provides different substances. Likewise, changing the extraction temperature (from one supercritical fluid extraction to another) can yield different substances. Moreover, various substances can be extracted from a plant with a solvent system having a specified combination of polarity (e.g., non-polar) and proticity (e.g., protic), whereas extraction from the same plant at the same temperature and pressure can provide different substances upon extraction from the plant with a solvent system having a different combination of polarity (e.g., non-polar) and proticity (e.g., aprotic). As such, various embodiments of the present invention provide for a supercritical fluid extraction carried out multiple times (i.e., a fractional supercritical fluid extraction), altering the pressure, temperature, polarity of the solvent system, and/or proticity of the solvent system. In doing so, unwanted material (e.g. terpenes, alkaloids, hemp oil, and/or cannabinoid acids) can be separated from *Cannabis* plant material, while obtaining the desired product (e.g. cannabinoids, terpenoids, and/or flavonoids).

Extraction is a diffusion-based process, with the solvent required to diffuse into the matrix, and the extracted material to diffuse out of the matrix into the solvent. Diffusivities are much faster in supercritical fluids than in liquids, and therefore extraction can occur faster. Also, there is no surface tension and viscosities are much lower than in liquids, so the solvent can penetrate into small pores within the matrix inaccessible to liquids. Both the higher diffusivity and lower viscosity significantly increase the speed of the extraction: An extraction using an organic liquid may take several hours, whereas supercritical fluid extraction can typically be completed in 10 to 60 minutes.

As used herein, "solvent system" refers to one or more solvents that dissolves a solute (a chemically different liquid, solid or gas), resulting in a solution. The maximum quantity of solute that can dissolve in a specific volume of solvent system varies with temperature and pressure. The solvent system can have a specified polarity and proticity. As such, solvent system can be polar, nonpolar, protic, or aprotic, wherein each of these terms is used in a relative manner.

As used herein, "polarity" refers to a separation of electric charge leading to a molecule or its chemical groups having an electric dipole or multipole moment. Polar molecules interact through dipole-dipole intermolecular forces and hydrogen bonds. Molecular polarity is dependent on the difference in electronegativity between atoms in a compound and the asymmetry of the compound's structure. Polarity underlies a number of physical properties including surface tension, solubility, and melting- and boiling-points.

As used herein, "polar" or "polar solvent" refers to a molecule having a net dipole as a result of the opposing charges (i.e., having partial positive and partial negative charges) from polar bonds arranged asymmetrically. Water ($H_2O$) is an example of a polar molecule since it has a slight positive charge on one side and a slight negative charge on the other. The dipoles do not cancel out resulting in a net dipole. Due to the polar nature of the water molecule itself, polar molecules are generally able to dissolve in water. Another example includes sugars (like sucrose), which have many polar oxygen-hydrogen (—OH) groups and are overall highly polar.

As used herein, "nonpolar" or "nonpolar solvent" refers to a molecule having an equal sharing of electrons between the two atoms of a diatomic molecule or because of the symmetrical arrangement of polar bonds in a more complex molecule. For example, the boron trifluoride molecule ($BF_3$) has a trigonal planar arrangement of three polar bonds at 120°. This results in no overall dipole in the molecule. In methane, the bonds are arranged symmetrically (in a tetrahedral arrangement) so there is no overall dipole. In the methane molecule ($CH_4$) the four C—H bonds are arranged tetrahedrally around the carbon atom. Each bond has polarity (though not very strong). However, the bonds are arranged symmetrically so there is no overall dipole in the molecule. The diatomic oxygen molecule ($O_2$) does not have polarity in the covalent bond because of equal electronegativity, hence there is no polarity in the molecule Examples of nonpolar solvents include, e.g., carbon dioxide ($CO_2$), hydrogen ($H_2$), neon (Ne), nitrogen ($N_2$), argon (Ar), methane ($CH_4$), ethane ($CH_3CH_3$), and propane ($CH_3CH_2CH_3$).

Organic solvents can range from nonpolar to polar, depending upon the molecular composition. For instance, organic solvents can be classified in a series ranging from nonpolar to polar, such as aliphatic hydrocarbon, aromatic hydrocarbon, halocarbon, ether, ketone, alcohol. By selection of an organic solvent, e.g. as a solvent or a cosolvent (with $CO_2$, etc.) in a supercritical fluid extraction, a selection of the polarity class of the substances extracted can be exerted. By using less polar solvent or cosolvent, a less polar set of, e.g., cannabinoid constituents can be obtained as a purified fraction. By use of a more polar solvent or cosolvent, a set of cannabinoid constituents of greater polarity can be selectively obtained as a purified fraction.

As used herein, "proticity" refers to the degree (or number) of occurrences of a hydrogen atom bound to an oxygen atom (as in a hydroxyl group), and/or a hydrogen atom bound to a nitrogen atom (as in an amine group), relative to the size or molecular weight of the molecule.

As used herein, "protic" or "protic solvent" refers to any solvent that contains labile H+. The molecules of such solvents readily donate protons (H+) to reagents.

As used herein, "aprotic" or "aprotic solvent" refers to any solvent that does not contain labile H+. The molecules of such solvents cannot readily donate protons (H+) to reagents.

As used herein, "mutually exclusive" refers to variables being related such that each excludes or precludes the other. For example, in the methods described herein to obtain a *Cannabis* extract, fractional supercritical fluid extract (FSFE) can be employed. In various embodiments of such FSFE, the SFE can be carried out two times (FSFE 1 and FSFE 2), each with the same solvent system and each at a different temperature and pressure. In such embodiments, while the solvent system of FSFE 1 and FSFE 2 are the same, the temperatures and pressures (of FSFE 1 and FSFE 2) are mutually exclusive. Specifically, each of the temperature and pressure of FSFE 1 is mutually exclusive of (e.g., different from) the temperature and pressure of FSFE 2.

As used herein, "fresh" refers to a plant (or any physical part thereof, such as a leaf, flowering bud, seed, etc.) that has been harvested within the past 21 days. In specific embodiments, the harvesting would have occurred within the past 14 days, within the past 10 days, within the past 7 days, or within the past 3 days.

As used herein, "dried" refers to a plant (or any physical part thereof, such as a leaf, bulb, seed, etc.) has undergone a drying process, such that an appreciable and significant amount of water (or moisture) has been removed. The drying process can include, e.g., an elevated temperature, a decreased pressure, or a combination thereof.

As used herein, "moisture content" or "water content" refers to the quantity of water contained in a material, such as, e.g., *Cannabis* plant material, or any part thereof. For example, dried *Cannabis* can have a moisture content of less than about 10 wt. %, less than about 5 wt. %, or less than about 1 wt. %.

As used herein, "harvested" refers to the act of gathering a crop (e.g., *Cannabis*) or any physical part thereof.

As used herein, "partially purified" refers to a raw material (e.g., *Cannabis*) that has undergone one or more processes (e.g., supercritical fluid extraction), such that the resulting product (e.g., extract of *Cannabis*) contains a desired substance (e.g., THC) in a concentration higher than the raw material. As such, the partially purified substance (e.g., extract of *Cannabis*) is said to be enriched with a desired substance (e.g., THC), relative to the raw material (e.g., *Cannabis*). As used herein, "partially purifying" refers to a process that provides a partially purified product. For example, the partially purified substance can be up to about 85% pure, up to about 75% pure, or up to about 50% pure.

"Purified fractions" can contain components present in different relative amounts or concentrations than found in the *Cannabis* plant material that has undergone a process of the invention. By this means, purified fractions of the total plant extract can be said to be "enriched" or "depleted" in specific components relative to other specific components. For instance, a purified fraction of plant material can contain a higher proportion of, e.g., cannabidiol relative to tetrahydrocannabinol, than is present in the plant material undergoing extraction. Purified fractions can be advantageous when it is desired to administer to a patient an extract that has a lower level of an undesired component (e.g., THC) and a higher level of a desired therapeutic constituent (e.g., cannabidiol).

As used herein, "purifying" refers to a process of rendering a substance, or a set of substances, pure, i.e. substantially free of, or having a lower relative content of, undesirable components. For example, the purified substance can be at least about 90% pure, at least about 95% pure, or at least about 98% pure.

As used herein, "terpene" refers to a hydrocarbon or derivative thereof, found as a natural product and biosynthesized by oligomerization of isoprene units. A terpene can be acyclic, monocyclic, bicyclic, or multicyclic. Examples include limonene, pulegone, caryophyllene epoxide, and the like.

As used herein, "alkaloid" refers to a natural product containing at least one basic nitrogen atom capable of forming salts with acids.

As used herein, "hemp oil" refers to a triglyceride, i.e., a triester of glycerol with fatty acids, typically extracted from hemp seeds with non-polar solvent.

As used herein, "cannabinoid acid" refers to a compound found naturally in a *Cannabis* species, formed by condensation of an alkyl-resorcinol and a terpene, which comprises a carboxylic acid group. Examples include cannabidiolic acid, tetrahydrocannabinolic acid, cannabichromenic acid, cannabigerolic acid, and the like.

As used herein, "multiple" refers to more than one, e.g., 2, 3, 4, 5, etc.

As used herein, "independently" refers to variables that are not influenced or controlled by other variables. Specifically, selection of one variable will not influence or control the selection of other variables. For example, in the methods described herein to obtain a *Cannabis* extract, fractional supercritical fluid extract (FSFE) can be employed. In various embodiments of such FSFE, the SFE can be carried out two times (FSFE 1 and FSFE 2), each with a different solvent system. In such embodiments, each of FSFE 1 and FSFE 2 can have the same or different temperature. Likewise, in such embodiments, each of FSFE 1 and FSFE 2 can have the same or different pressure. In such embodiments, while the solvent system of FSFE 1 and FSFE 2 are different, the temperatures and pressures (of FSFE 1 and FSFE 2) can be independently selected. In doing so, each of the temperature and pressure (of FSFE 1 and FSFE 2) can be the same, or can be different.

As used herein, "combining" refers to the act of bringing into contact two or more substances. For example, in the methods described herein, a plant material (e.g., *Cannabis*) can be combined with a solvent system. In doing so, the plant material and solvent system will be in close proximity, such that they contact each other. The solvent system can be added to a vessel containing the plant material or the plant material can be added to the vessel containing the solvent system.

As used herein, "discarding" refers to the act of casting aside, disposing of, or otherwise not using in a subsequent process, step, or article of manufacture.

As used herein, "chromatography" refers to a process for separation of constituents of a mixture of organic compounds wherein the compounds are differentially absorbed and eluted from a solid phase by a liquid solvent (liquid chromatography) or by a gas (gas chromatograph). Representative chromatography include, e.g., high pressure liquid chromatography (HPLC).

As used herein, "adsorption" refers to a physical process whereby a molecule enters into an energetically favorable association with a solid surface.

As used herein, "crystallization" refers to a process whereby a sample of a molecular entity forms crystals, usually on precipitation from a solvent or solvent mixture.

As used herein, "distillation" refers to a purification process whereby liquid components are separated on the basis of boiling point, often under reduced atmospheric pressure, in a still.

As used herein, "liquid-liquid extraction" refers to a process whereby chemical compounds are partitioned between two substantially immiscible liquid phases.

As used herein, "filtration" refers to a process whereby a solid and a liquid are separated by passage of a mixture of the two through a filter medium, where the solid material is retained and the liquid passes through.

As used herein, "fractional distillation" refers to a distillation as described above, where multiple components are separated sequentially by increasing boiling point, often under reduced atmospheric pressure.

As used herein, "precipitation" refers to a separation from a solution of a solid material.

As used herein, "recrystallization" refers to a purification process whereby a crystalline material is dissolved, then subsequently again put under conditions where crystallization occurs, usually in a highly controlled manner such that a substantial increase in purity of the compound is obtained.

As used herein, "sublimation" refers to a physical process whereby a solid material passes into a vapor phase without passing through an intervening liquid phase.

In specific embodiments, the desired extract (or concentrate) of *Cannabis*, relative to the starting plant material, will be enriched with the desired product (e.g. cannabinoids, terpenoids, and/or flavonoids). In further embodiments, the desired extract (or concentrate) of *Cannabis*, relative to the undesired extract of *Cannabis*, will be enriched with the desired product (e.g. cannabinoids, terpenoids, and/or flavonoids). In yet further embodiments, the undesired extract (or concentrate) of *Cannabis*, relative to the desired extract of *Cannabis*, will be enriched with the undesired product (e.g. terpenes, alkaloids, hemp oil, and/or cannabinoid acids). As such, the FSFE can be employed to selectively obtain one or more desired substances from the *Cannabis* plant material, while selectively excluding one or more undesired substances.

In specific embodiments, the desired extract (or concentrate) of *Cannabis*, relative to the starting plant material, will include a lower concentration of the undesired product (e.g. terpenes, alkaloids, hemp oil, and/or cannabinoid acids). In further embodiments, the desired extract (or concentrate) of *Cannabis*, relative to the undesired extract of *Cannabis*, will include a lower concentration of the undesired product (e.g. terpenes, alkaloids, hemp oil, and/or cannabinoid acids). In yet further embodiments, the undesired extract (or concentrate) of *Cannabis*, relative to the desired extract of *Cannabis*, will include a lower concentration of the desired product (e.g. cannabinoids, terpenoids, and/or flavonoids). As such, the FSFE can be employed to selectively obtain one or more desired substances from the *Cannabis* plant material, while selectively excluding one or more undesired substances.

As used herein, "enrich" refers to an increase the concentration or amount of one substance, relative to the concentration or amount of another substance; or one material containing a higher concentration or amount of a substance, compared to a second material's concentration or amount of that substance. The difference in the amount (weight/mass) can be at least about 1%, at least about 5%, at least about 10%, at least about 25%, or at least about 50%. Likewise, the difference in concentration can be at least about 1%, at least about 5%, at least about 10%, at least about 25%, or at least about 50%. In reference to "higher concentration" and "lower concentration," the difference in concentration can be at least about 1%, at least about 5%, at least about 10%, at least about 25%, or at least about 50%.

As used herein, "relative concentration" refers to the concentration of a specified substance (or a combination of specified substances) that is present in a lower concentration ("lower relative concentration"), or is present in a higher concentration ("higher relative concentration"), compared to the concentration of the same substances in the *Cannabis* plant material. In specific embodiments, the *Cannabis* concentrate (compared to the *Cannabis* plant material) can include a higher relative concentration of compound "X," or a lower relative concentration of compound "Z." In such an embodiment, the concentration of compound "X" will be higher in the *Cannabis* concentrate compared to the concentration of compound "X" in the *Cannabis* plant material. Likewise, the concentration of compound "Z" will be lower in the *Cannabis* concentrate compared to the concentration of compound "Z" in the *Cannabis* plant material. The increase (or decrease) can range anywhere from about 10% to 100,000 fold. In specific embodiments, the increase (or decrease) can be about 10% to 10,000 fold; about 20% to 1,000 fold; about 50% to 100 fold; about 2 fold to 100 fold; about 3 fold to 50 fold; or about 5 fold to 25 fold.

As used herein, "pharmaceutical dosage form" refers to a pharmaceutical product in the form in which it is marketed for use, typically involving a mixture of active drug components and nondrug components (excipients), along with other non-reusable material that may not be considered either ingredient or packaging (such as a capsule shell, for example). The term pharmaceutical dosage form can also refer only to the chemical formulation of a drug product's constituent drug substance(s) and any blends involved, without considering matters beyond that (like how it's ultimately configured as a consumable product such as a capsule, patch, etc.).

Depending on the method/route of administration, pharmaceutical dosage forms come in several types. These include many kinds of liquid, solid, and semisolid dosage forms. Common pharmaceutical dosage forms include pill, tablet, or capsule, drink or syrup, and natural or herbal form such as plant or food of sorts, among many others. Notably, the route of administration (ROA) for drug delivery is dependent on the dosage form of the substance in question. A liquid pharmaceutical dosage form is the liquid form of a dose of a chemical compound used as a drug or medication intended for administration or consumption.

Various pharmaceutical dosage forms may exist for a single particular drug, since different medical conditions can warrant different routes of administration. For example, persistent nausea and emesis or vomiting may make it difficult to use an oral dosage form, and in such a case, it may be necessary to utilize an alternate route such as inhalational, buccal, sublingual, nasal, suppository or parenteral instead. Additionally, a specific pharmaceutical dosage form may be a requirement for certain kinds of drugs, as there may be issues with various factors like chemical stability or pharmacokinetics.

Exemplary pharmaceutical dosage forms include, e.g., pills, osmotic delivery systems, elixirs, emulsions, hydrogels, suspensions, syrups, capsules, tablets, orally dissolving tablets (ODTs), gel capsules, thin films, adhesive topical patches, lollipops, lozenges, chewing gum, dry powder inhalers (DPIs), vaporizers, nebulizers, metered dose inhalers (MDIs), ointments, transdermal patches, intradermal implants, subcutaneous implants, and transdermal implants.

As used herein, "oral delivery" or "oral administration" refers to a route of administration wherein the pharmaceutical dosage form is taken through the mouth. Oral administration is a part of enteral administration, which also includes buccal (dissolved inside the cheek), sublabial (dissolved under the lip) and sublingual administration (dissolved under the tongue). Enteral medications come in various forms, including: tablets to swallow, chew or dissolve in water or under the tongue; capsules and chewable capsules (with a coating that dissolves in the stomach or bowel to release the medication there); time-release or sustained-release tablets and capsules (which release the medication gradually); powders or granules; teas; drops; and liquid medications or syrups.

As used herein, "ophthalmic delivery" or "ophthalmic administration" refers to a route of administration wherein the pharmaceutical dosage form is taken to, or through, the eye.

As used herein, "nasal delivery" or "nasal administration" refers to a route of administration wherein the pharmaceutical dosage form is taken to, or through, the nose (e.g., nasal cavity).

As used herein, "dermal delivery" or "dermal administration" refers to a route of administration wherein the pharmaceutical dosage form is taken to, or through, the dermis (i.e., layer of skin between the epidermis (with which it makes up the cutis) and subcutaneous tissues).

As used herein, "pill" refers to a small, round, solid pharmaceutical oral dosage form of medication that was in use before the advent of tablets and capsules. Pills were historically made by mixing the active ingredients with an excipient such as glucose syrup in a mortar and pestle to form a paste, then rolling the mass into a long cylindrical shape (called a "pipe"), and dividing it into equal portions, which were then rolled into balls, and often coated with sugar to make them more palatable. Today, pills include tablets, capsules, and variants thereof like caplets—essentially anything with medication that can be digested, minus the liquid forms, falls into the pill category.

As used herein, "osmotic delivery system" or "osmotic controlled release oral delivery system" or "OROS" refers to a controlled release oral drug delivery system in the form of a tablet. The tablet has a rigid water-permeable jacket with one or more laser drilled small holes. As the tablet passes through the body, the osmotic pressure of water entering the tablet pushes the active drug through the opening in the tablet.

As used herein, "capsule" refers to a solid pharmaceutical oral dosage form wherein the active (and inactive) ingredient is encapsulated. Encapsulation refers to a range of techniques used to enclose medicines in a relatively stable shell known as a capsule, allowing them to, for example, be taken orally or be used as suppositories. The two main types of capsules include hard-shelled capsules, which are typically made using gelatin and contain dry, powdered ingredients or miniature pellets made by, e.g. processes of extrusion or spheronisation. These are made in two halves: a lower-diameter "body" that is filled and then sealed using a higher-diameter "cape". The second main type of capsules include soft-shelled capsules, primarily used for oils and for active ingredients that are dissolved or suspended in oil. Both of these classes of capsules are made from aqueous solutions of gelling agents like such as animal protein mainly gelatin; and plant polysaccharides or their derivatives like carrageenans and modified forms of starch and cellulose. Other ingredients can be added to the gelling agent solution like plasticizers such as glycerin and/or sorbitol to decrease the capsule's hardness, coloring agents, preservatives, disintegrants, lubricants and surface treatment.

As used herein, "tablet" refers to a pharmaceutical dosage form that includes a mixture of active substances and excipients, usually in powder form, pressed or compacted from a powder into a solid dose. The excipients can include diluents, binders or granulating agents, glidants (flow aids) and lubricants to ensure efficient tabletting; disintegrants to promote tablet break-up in the digestive tract; sweeteners or flavours to enhance taste; and pigments to make the tablets visually attractive. A polymer coating is often applied to make the tablet smoother and easier to swallow, to control the release rate of the active ingredient, to make it more resistant to the environment (extending its shelf life), or to enhance the tablet's appearance.

As used herein, "orally dissolving tablet" or "ODT" refers to pharmaceutical dosage form designed to be dissolved on the tongue rather than swallowed whole. The ODT serves as an alternative dosage form for patients who experience dysphagia (difficulty in swallowing) or for where compliance is a known issue and therefore an easier dosage form to take ensures that medication is taken. Common among all age groups, dysphagia is observed in about 35% of the general population, as well as up to 60% of the elderly institutionalized population and 18-22% of all patients in long-term care facilities. Additional reasons to use ODTs include the convenience of a tablet that can be taken without water as well as the inability of the patient to eat or drink (e.g., nausea and/or vomiting).

As used herein, "oral thin film," "OTF," "oral dissolving film," "oral drug strip," "oral thin film," "thin film," "orally dissolvable film strip," or "oral strip" refers to a product used to administer active ingredients via absorption in the mouth (buccally or sublingually), the stomach (gastrically), and/or via the small intestines (enterically). The OTF is edible and pharmaceutically acceptable. A film is prepared typically using hydrophilic polymers that rapidly dissolves on the tongue, palatine tissue, or buccal cavity, delivering the active ingredient to the systemic circulation via dissolution when contact with liquid is made. The OTF (or more appropriately "thin film" or "TF") can also be used to adhere to mucosal tissue (e.g., at least one of mouth, nose, eye, vagina, and rectum), thereby locally delivering the active ingredient(s). As such, it is appreciated that those of skill in the art understand that reference to a thin film for use with mucosal tissue, such as nose, eye, vagina, and rectum, as an "oral thin film" or OTF is appropriate and acceptable.

The term "film" includes thin films and sheets, in any shape, including rectangular, square, or other desired shape. The films described herein may be any desired thickness and size such that it may be placed into the oral cavity of the user. For example, the films may have a relatively thin thickness of from about 0.1 to about 10 mils, or they may have a somewhat thicker thickness of from about 10 to about 30 mils. For some films, the thickness may be even larger, i.e., greater than about 30 mils. In addition, the term "film" includes single-layer compositions as well as multi-layer compositions, such as laminated films. The composition in its dried film form can effectively maintain a relatively uniform distribution of components through the application of controlled drying of the film. For example, the film can have no more than a 20%, 10%, 5%, or 1% variance of the active ingredient, per unit area of the film.

As used herein, "adhesive topical patch" or "transdermal patch" refers to a medicated adhesive patch that is placed on the skin to deliver a specific dose of medication through the skin and into the bloodstream. A transdermal patch or transdermal system (TDS) is a medicated adhesive patch that is placed on the skin to deliver a specific dose of drug through the skin and into the bloodstream. An advantage of a transdermal drug delivery route over other types of medication delivery such as oral, topical, intravenous, intramuscular, etc. is that the patch provides a controlled release of the medication into the patient, usually through either a porous membrane covering a reservoir of medication or through body heat melting thin layers of medication embedded in the adhesive. The main disadvantage to transdermal delivery systems stems from the fact that the skin is a very effective barrier; as a result, only medications whose molecules are small enough to penetrate the skin can effectively be delivered by this method.

The transdermal patch serves as an alternative dosage form for patients who experience dysphagia (difficulty in swallowing). Additional reasons to use transdermal patches include the convenience of a dosage form that can be taken without water as well as the inability of the patient to eat or drink (e.g., nausea and/or vomiting).

As used herein, "therapeutically effective amount" is intended to include an amount of a substance (or compound) described herein, or an amount of the combination of substances (or compounds) described herein, e.g., to treat or prevent the disease or disorder, or to treat the symptoms of the disease or disorder, in a host. The combination of substances (or compounds) is preferably a synergistic combination. Synergy, as described for example by Chou and Talalay, *Adv. Enzyme Regul.*, 22:27 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

As used herein, "treating" or "treat" includes: (i) preventing a pathologic condition from occurring (e.g. prophylaxis); (ii) inhibiting the pathologic condition or arresting its development; (iii) relieving the pathologic condition; and/or (iv) diminishing symptoms associated with the pathologic condition.

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

As used herein, "neuro inflammation" refers to a medical condition wherein neural tissue undergoes an inflammatory response.

As used herein, "epilepsy" refers to a medical condition characterized by petit mal or grand mal seizures, resulting from aberrant brain electrical activity.

As used herein, "Alzheimer's disease" refers to a form of dementia in patients characterized by memory loss and formation of amyloid plaques in brain tissue.

As used herein, "oxidative injury" refers to an injury sustained by tissue components due to the reaction of those components with oxidizing substances.

As used herein, "vomiting" refers to a symptom of a medical condition whereby the contents of the stomach are ejected through the mouth.

As used herein, "nausea" refers to a sensation experienced by a patient of an imminent need to vomit, accompanied by dizziness or disorientation.

As used herein, "anxiety" refers to an emotional state in which a person experiences fear of some real or imagined future event.

As used herein, "anorexia" refers to a symptom characterized by loss of appetite for food.

As used herein, "arthritis" refers to inflammation of the bone fascia producing pain and immobility.

As used herein, "schizophrenia" refers to a mental health state characterized by disorientation, delusion, disorganized thinking, lack of emotion, and mental imbalance.

As used herein, "multiple sclerosis" refers to an inflammatory disease wherein myelin-producing cells surrounding neurons undergo deterioration, resulting in physical and mental symptoms.

As used herein, "joint inflammation" refers to an inflammatory response occurring in the bone joints, producing pain and immobility.

As used herein, "joint pain" refers to pain associated with the relative motion of two or more bones at a mutual joint thereof.

As used herein, "symptoms associated with AIDS" refers to those symptoms produced by infection of a patient with Human Immunodeficiency Virus (HIV), including reduced resistance to infections and formation of opportunistic tumors.

As used herein, "chronic pain" refers to pain experienced over a prolonged period of time.

As used herein, "acute pain" refers to pain of a high degree of severity.

As used herein, "neuropathic pain and spasticity" refers to pain and loss of muscle control produced by damage or disease that affects the somatosensory system, which can results from injury or disease of the central or peripheral nervous systems.

As used herein, "inflammatory bowel diseases (IBD)" refers to inflammatory conditions afflicting the colon and small intestine, including Crohn's disease and ulcerative colitis.

As used herein, "tumor neovascularization" refers to the induction of blood vessel growth by a tumor, supplying increased blood flow to the neoplasm.

As used herein, "tumor growth" refers to the abnormal growth of neoplasms with the body.

As used herein, "cancer cell migration" refers to the physical translocation of metastatically transformed neoplastic cells within the body.

As used herein, "cancer cell adhesion" refers to the adhesion of metastatically transformed neoplastic cells to tissues and structures within the body.

As used herein, "cancer cell invasion" refers to a process whereby metastatically transformed neoplastic cells invade other tissues of the body.

As used herein, "cancer cell metastasization" refers to a cellular process whereby a cell becomes cancerous and capable of inducing metastatic transformation in normal cells, thereby spreading a cancer.

As sued herein "time release technology" refers to a mechanism used in pharmaceutical dosage forms (e.g., pill, tablet, capsule, transdermal patch, etc.) to dissolve a drug over time in order to be released slower and steadier into the bloodstream, while having the advantage of being taken at less frequent intervals than immediate-release (IR) formulations of the same drug. The time release technology can include sustained-release (SR), sustained-action (SA), extended-release (ER, XR, XL), timed-release (TR), controlled-release (CR), modified release (MR), or continuous-release (Contin).

There are certain considerations for the formation of time release formulation: (i) if the active compound has a long half-life (over 6 hours), it is sustained on its own; (ii) if the pharmacological activity of the active compound is not related to its blood levels, time releasing has little or no purpose; (iii) if the absorption of the active compound involves an active transport, the development of a time-release product may be problematic; and (iv) if the active compound has a short half-life, it would require a large amount to maintain a prolonged effective dose. In this case, a broad therapeutic window is necessary to avoid toxicity; otherwise, the risk is unwarranted and another mode of administration would be recommended.

As used herein, "single daily dosage" refers to a dose suitable for a single administration over a 24 hour period. The dose is configured for a single administration over a 24 hour period.

Supercritical Fluid Extraction (SFE)

Supercritical fluid extraction is an extraction wherein a fluid at a temperature and pressure above its critical point is employed; or a fluid above its critical temperature, regardless of pressure, is employed. Below the critical point, the fluid can coexist in both gas and liquid phases, but above the critical point there is only one phase. Equipment and techniques for carrying out supercritical fluid extraction are known to those skilled in the art. See, McHugh, M. And Krukonis, V., Supercritical Fluid Extraction, 2nd ed, Butterworth-Heinemann, Boston, 1994; Johnston, K. P., Penninger, J. M. L., Supercritical Fluid Science and Technology, ACS Symposium Series 406, American Chemical Society, Washington, D.C.; and Taylor, L. T., Supercritical Fluid Extraction, John Wiley & Sons, New York, 1996.

In a supercritical fluid extraction, thermodynamic and transport properties of supercritical fluid are a function of density, which depends strongly on the fluid's pressure and temperature. The density may be adjusted from a gas-like value of 0.1 g/ml to a liquid-like value as high as 1.2 g/ml. Furthermore, as conditions approach the critical point, the effect of temperature and pressure on density becomes much more significant. For example, increasing the density of supercritical carbon dioxide from 0.2 to 0.5 g/ml typically requires raising the pressure from 85 atm to 140 atm (8.6 megapascals to 14.2 megapascals) at 158° F. (70° C.), but at 95° F. (35° C.) the required change is only from 65 atm to 80 atm (6.61 Mpa to 8.1 Mpa).

In specific embodiments, the supercritical fluid extraction can be carried out multiple times. In such embodiments, the supercritical fluid extraction is a fractional supercritical fluid extraction. "Fractional supercritical fluid extraction" (hereinafter "FSFE") refers to a supercritical fluid extraction that is carried out multiple times. Each time the supercritical fluid extraction is carried out, at least one of the (i) solvent system (with respect to polarity and proticity), (ii) temperature and (iii) pressure will vary.

For example, in reference to Cannabis, the FSFE can include a supercritical fluid extraction that is carried out two times, three times, four times, etc. At each time (occurrence), the temperature, pressure, period of time, and supercritical fluid solvent system are each independently selected (e.g., can independently be the same or different).

When the SFE is carried out two times, the FSFE can include: (a) contacting Cannabis plant material with a supercritical fluid solvent system at a suitable pressure (e.g., between about 750 psi and 25,000 psi), and at a suitable temperature (e.g., between about −15° C. and 200° C.), to provide an extract of Cannabis and an extracted Cannabis plant material; (b) removing the supercritical fluid solvent system from the extract of Cannabis; (c) contacting the extracted Cannabis with a second supercritical fluid solvent system at a suitable pressure (e.g., between about 750 psi and 25,000 psi), and at a suitable temperature (e.g., between about −15° C. and 200° C.), to provide a second extract of Cannabis and a second extracted Cannabis plant material; and (d) removing the second supercritical fluid solvent system from the second extract of Cannabis.

When the SFE is carried out three times, the FSFE can include: (a) contacting Cannabis plant material with a supercritical fluid solvent system at a suitable pressure (e.g., between about 750 psi and 25,000 psi), and at a suitable temperature (e.g., between about −15° C. and 200° C.), to provide an extract of Cannabis and an extracted Cannabis plant material; (b) removing the supercritical fluid solvent system from the extract of Cannabis; (c) contacting the extracted Cannabis plant material with a second supercritical fluid solvent system at a suitable pressure (e.g., between about 750 psi and 25,000 psi), and at a suitable temperature (e.g., between about −15° C. and 200° C.), to provide a second extract of Cannabis and a second extracted Cannabis plant material; (d) removing the second supercritical fluid solvent system from the second extract of Cannabis; (e) contacting the second extracted Cannabis plant material with a third supercritical fluid solvent system at a suitable pressure (e.g., between about 750 psi and 25,000 psi), and at a suitable temperature (e.g., between about −15° C. and 200° C.), to provide a third extract of Cannabis and a third extracted Cannabis plant material; and (f) removing the third supercritical fluid solvent system from the third extract of Cannabis.

When the SFE is carried out four times, the FSFE can include: (a) contacting Cannabis with a supercritical fluid solvent system at a suitable pressure (e.g., between about 750 psi and 25,000 psi), and at a suitable temperature (e.g., between about −15° C. and 200° C.), to provide an extract of Cannabis and an extracted Cannabis plant material; (b) removing the supercritical fluid solvent system from the extract of Cannabis; (c) contacting the extracted Cannabis plant material with a second supercritical fluid solvent system at a suitable pressure (e.g., between about 750 psi and 25,000 psi), and at a suitable temperature (e.g., between about −15° C. and 200° C.), to provide a second extract of Cannabis and a second extracted Cannabis plant material; (d) removing the second supercritical fluid solvent system from the second extract of Cannabis; (e) contacting the second extracted Cannabis plant material with a third supercritical fluid solvent system at a suitable pressure (e.g., between about 750 psi and 25,000 psi), and at a suitable temperature (e.g., between about −15° C. and 200° C.), to provide a third extract of Cannabis and a third extracted Cannabis plant material; (f) removing the third supercritical fluid solvent system from the third extract of Cannabis; (g) contacting the third extracted Cannabis plant material with a fourth supercritical fluid solvent system at a suitable pressure (e.g., between about 750 psi and 25,000 psi), and at a suitable temperature (e.g., between about −15° C. and 200° C.), to provide a fourth extract of Cannabis and a fourth extracted *Cannabis*; and (h) removing the fourth supercritical fluid solvent system from the fourth extract of *Cannabis*.

Prior to an initial supercritical fluid extraction, the *Cannabis* may be dried of any water present. Such drying may increase the efficiency of the supercritical fluid extraction, or may just lower the cost of shipping and storage of *Cannabis* plant material. The *Cannabis* may be air-dried or dried at an elevated temperature with or without reduced pressure (i.e., in vacuo). Specifically, the *Cannabis* may be dried in vacuo at an elevated temperature. Machines capable of drying *Cannabis* are known in the art and include an oven, or similar device, such as a rotating air drum drier.

For use in the processes of the present invention, the temperature at which the *Cannabis* may be dried can be greater than about 25° C. Specifically, the temperature can be greater than about 30° C., greater than about 40° C., or greater than about 50° C. More specifically, the temperature can be greater than about 60° C., greater than about 70° C., or greater than about 80° C.

The supercritical fluid extraction can conveniently be carried out at a pressure of about 750 psi to about 50,000 psi. It is appreciated that those skilled in the art understand that higher pressures may enable faster extraction. In this case, it may be desirable to subsequently separate and purify the product. Specifically, the pressure may be about 1,000 psi to about 50,000 psi, about 1,500 psi to about 40,000 psi, about 2,000 psi to about 35,000 psi, or about 2,500 psi to about 30,000 psi. More specifically, the pressure may be about 1,000 psi to about 25,000 psi, about 1,000 psi to about 20,000 psi, about 1,000 psi to about 15,000 psi, or about 1,000 psi to about 10,000 psi. More specifically, the pressure may be about 2,000 psi to about 25,000 psi, about 2,000 psi to about 20,000 psi, about 2,000 psi to about 15,000 psi, or about 2,000 psi to about 12,000 psi.

For use in the processes of the present invention, the temperature of supercritical fluid extraction can conveniently be about 30° C. to about 250° C. Specifically, the temperature can be about 30° C. to about 200° C., about 30° C. to about 150° C., or about 30° C. to about 100° C. More specifically, the temperature can be about 35° C. to about 200° C., about 35° C. to about 150° C., or about 35° C. to about 100° C. More specifically, the temperature can be about 40° C. to about 200° C., about 40° C. to about 150° C., or about 40° C. to about 100° C.

For use in the processes of the present invention, the period of time of supercritical fluid extraction can conveniently be up to about 24 hours (e.g., about 1 minute to about 24 hours). For example, the period of time of supercritical fluid extraction can be about 5 minutes to about 12 hours, or about 10 minutes to about 1 hour. Specifically, the period of time of supercritical fluid extraction can be about 5-10 minutes, about 10-20 minutes, about 20-30 minutes, about 30-40 minutes, about 40-50 minutes, about 50-60 minutes, about 60-70 minutes, about 70-80 minutes, about 80-90 minutes, about 90-100 minutes, etc.

Supercritical fluid extraction employs a solvent (and optionally a co-solvent) which possesses physical properties suitable as a supercritical fluid. Suitable solvents (and co-solvents) useful in supercritical fluid extraction are disclosed, e.g., McHugh, M. And Krukonis, V., Supercritical Fluid Extraction, 2nd ed, Butterworth-Heinemann, Boston, 1994; Johnston, K. P., Penninger, J. M. L., Supercritical Fluid Science and Technology, ACS Symposium Series 406, American Chemical Society, Washington, D.C.; and Taylor, L. T., Supercritical Fluid Extraction, John Wiley & Sons, New York, 1996. Suitable exemplary solvents (and co-solvents) useful in supercritical fluid extraction include: carbon dioxide ($CO_2$), hydrogen ($H_2$), neon (Ne), nitrogen ($N_2$), argon (Ar), methane ($CH_4$), ethane ($CH_3CH_3$), propane ($CH_3CH_2CH_3$), ammonia ($NH_3$), water ($H_2O$), xenon (Xe), methanol, ethanol, 1-propanol, 2-propanol, 1-hexanol, 2-methoxy ethanol, tetrahydrofuran (THF), 1,4-dioxane, acetonitrile, methylene chloride, dichloroethane, chloroform, ethyl acetate, propylene carbonate, N,N-dimethylacetamide, dimethyl sulfoxide (DMSO), formic acid, carbon disulfide, acetone, toluene, hexanes, pentanes, trifluoromethane (Freon® 23), nitrous oxide ($N_2O$), sulfur hexafluroide ($SF_6$), butane (n-$C_4H_{10}$), isobutane (i-$C_4H_{10}$), ethyl ether (($C_2H_5$)$_2$O), benzotrifluoride ($C_6H_5CF_3$), (p-chlorophenyl)trifluoromethane (Cl$C_6H_4CF_3$), chlorofluorocarbon (CFC), hydrofluorocarbon (HFA), and HFA-134a (1,1,1,2-tetrafluoroethane).

Typically, when present, the co-solvent will be present in about 1 wt. % to about 50 wt. %, in about 1 wt. % to about 30 wt. %, or in about 1 wt. % to about 10 wt. % of the supercritical fluid solvent system.

The physical properties of carbon dioxide make it particularly attractive as a solvent for supercritical fluid extraction. Carbon dioxide is a major component of the atmosphere and is therefore relatively safe and abundant. In addition, carbon dioxide is relatively inexpensive. Compared to most other suitable solvents, carbon dioxide is environmentally friendly as it will not harm the atmosphere at the quantities used in the methods of the invention. Moreover, carbon dioxide is non-flammable and non-explosive. Further, carbon dioxide leaves no substantial residue or remnant upon evaporation.

Carbon dioxide also possesses physical properties which enable it to change polarity over the temperature range and pressure range normally employed in supercritical fluid extraction. As a result, carbon dioxide may act as a nonpolar solvent at one temperature and pressure but may act as a polar solvent at another temperature and pressure. By varying the temperature and pressure, the solvent properties may be modified. This allows for the isolation of more than one compound using a single solvent system.

The co-solvent can be employed for several practical reasons. The co-solvent decreases the time necessary for extraction, which decreases the costs incurred for the extraction process and increases the efficiency of the extraction process. In addition, the use of at least one co-solvent decreases the likelihood that the desired compound(s) will crystallize or gum out upon evaporation of the highly volatile solvent carbon dioxide. When the supercritical fluid extraction apparatus is dismantled and the desired compounds are obtained, the carbon dioxide will evaporate, leaving the desired crude compounds as a solid or gum-like tar. The use of the co-solvent allows the desired compound(s) to remain soluble in a solvent system.

The solvent employed in supercritical fluid extraction may be a single compound or may be a mixture of compounds. In addition, the solvent may include an additive. As used herein, an "additive" refers to a substance such that upon addition will modify the physical properties of the solvent. For example, an additive may be useful to modify the polarity, critical temperature, critical pressure, etc., of the solvent system. When present, the additive can be present in about 0.5 wt. % to about 25 wt. % of the solvent system, about 0.5 wt. % to about 20 wt. % of the solvent system, or about 0.5 wt. % to about 15 wt. % of the solvent system. Specifically, when present, the additive can be present in about 1 wt. % to about 15 wt. % of the solvent system, about 1 wt. % to about 10 wt. % of the solvent system, or about 1 wt. % to about 5 wt. % of the solvent system.

Suitable additives include, e.g., lower alcohols (e.g., methanol, ethanol, 1-propanol, 2-propanol, 1-hexanol, or 2-methoxy ethanol); ethers (e.g., tetrahydrofuran or 1,4-dioxane); substituted hydrocarbons (e.g., acetonitrile, dichloromethane, ammonia or chloroform) propylene carbonate, N,N-dimethylaceamide; dimethyl sulfoxide; carboxylic acids (e.g., formic acid); water; carbon disulfide; lower ketones (e.g., acetone), hydrocarbons (e.g., propane, toluene, hexanes and pentanes); substituted aromatics (e.g., $C_6H_5CF_3$, and $p\text{-}ClC_6H_4CF_3$).

The SFE, or any SFE of the FSFE, can be carried out over a suitable and effective period of time. For use in the processes of the present invention, the suitable and effective period of time can be about 10 seconds to about 60 minutes. Specifically, the suitable and effective period of time can be about 20 seconds to about 60 minutes, about 30 seconds to about 60 minutes, or about 40 seconds to about 60 minutes. More specifically, the suitable and effective period of time can be about 10 seconds to about 30 minutes, about 10 seconds to about 20 minutes, or about 10 seconds to about 10 minutes. More specifically, the suitable and effective period of time can be about 20 seconds to about 40 minutes, about 30 seconds to about 30 minutes, or about 40 seconds to about 20 minutes.

Additional conditions (e.g., time, temperature and pressure), solvents, co-solvents, and apparatus, for carrying out the SFE are described, e.g., in U.S. Pat. Nos. 8,501,250; 8,003,144; 7,811,997; 7,368,589; 7,214,379; 7,083,748; 6,909,021; 6,773,473; 6,746,695; 6,737,552; and 6,576,274.

Cannabis Concentrate

The present invention provides for a pharmaceutical dosage form that includes a *Cannabis* concentrate. The *Cannabis* concentrate is obtained from the *Cannabis* extract, which is obtained from the *Cannabis* plant material. The *Cannabis* concentrate can include, e.g., cannabinoids, terpenoids, and/or flavonoids. In various embodiments, the *Cannabis* concentrate (relative to the starting plant material) can be enriched with the desired product (e.g. cannabinoids, terpenoids, and/or flavonoids, or purified fractions in which certain cannabinoid compounds are enriched or depleted relative to other cannabinoid compounds). In further embodiments, the *Cannabis* concentrate (relative to the starting plant material) can be enriched with one or more specific desired products (e.g. cannabinoids) relative to other desired products (e.g., terpenoids and/or flavonoids). Additionally, compared to the *Cannabis* plant material, the *Cannabis* concentrate can contain a lower concentration of unwanted material (e.g. terpenes, alkaloids, hemp oil, and/or cannabinoid acids).

In specific embodiments, the *Cannabis* concentrate can be enriched in terpenoids, flavonoids, and/or cannabinoids. In further specific embodiments, the *Cannabis* concentrate can be enriched in at least one of cannabinol (CBN); cannabinolic acid (CBNA); Δ(9)-tetrahydrocannabinol (Δ(9)-THC); Δ(9)-tetrahydrocannabinolic acid (Δ(9)-THCA); Δ(9)-cannabidiol (Δ(9)-CBD); Δ(9)-tetrahydrocannabidiolic acid (Δ(9)-CBDA); Δ(8)-tetrahydrocannabinol (Δ(8)-THC); Δ(8)-tetrahydrocannabinolic acid (Δ(8)-THCA); Δ(8)-tetrahydrocannabidiol (Δ(8)-CBD); Δ(8)-tetrahydrocannabidiolic acid (Δ(8)-CBDA); Δ(9)-tetrahydrocannabivarin (Δ(9)-THV); cannabigerol (CBG); cannabigerolic acid (CBGA); cannabichromene (CBC); cannabichromenic acid (CBCA); cannabicyclol (CBL); cannabicyclolic acid (CBLA); β-caryophyllene epoxide; mentha-1,8(9)-dien-5-ol; pulegone; limonene; limonene oxide; α-terpinene; terpinen-4-ol; carvacrol; carvone; 1,8-cineole; p-cymene; fenchone; pulegone-1,2epoxide; β-myrcene; cannaflavin A; and cannaflavin B.

In specific embodiments, the *Cannabis* concentrate can include a therapeutically effective amount of at least one of cannabinol (CBN); cannabinolic acid (CBNA); Δ(9)-tetrahydrocannabinol (Δ(9)-THC); Δ(9)-tetrahydrocannabinolic acid (Δ(9)-THCA); Δ(9)-cannabidiol (Δ(9)-CBD); Δ(9)-tetrahydrocannabidiolic acid (Δ(9)-CBDA); Δ(8)-tetrahydrocannabinol (Δ(8)-THC); Δ(8)-tetrahydrocannabinolic acid (Δ(8)-THCA); Δ(8)-tetrahydrocannabidiol (Δ(8)-CBD); Δ(8)-tetrahydrocannabidiolic acid (Δ(8)-CBDA); Δ(9)-tetrahydrocannabivarin (Δ(9)-THV); cannabigerol (CBG); cannabigerolic acid (CBGA); cannabichromene (CBC); cannabichromenic acid (CBCA); cannabicyclol (CBL); cannabicyclolic acid (CBLA); β-caryophyllene epoxide; mentha-1,8(9)-dien-5-ol; pulegone; limonene; limonene oxide; α-terpinene; terpinen-4-ol; carvacrol; carvone; 1,8-cineole; p-cymene; fenchone; pulegone-1,2epoxide; β-myrcene; cannaflavin A; and cannaflavin B.

In specific embodiments, the *Cannabis* concentrate can be enriched in cannabinol (CBN). In additional specific embodiments, the *Cannabis* concentrate can include a therapeutically effective amount of cannabinol (CBN).

In specific embodiments, the *Cannabis* concentrate can be enriched in cannabinolic acid (CBNA). In additional specific embodiments, the *Cannabis* concentrate can include a therapeutically effective amount of cannabinolic acid (CBNA).

In specific embodiments, the *Cannabis* concentrate can be enriched in Δ(9)-tetrahydrocannabinol (Δ(9)-THC). In additional specific embodiments, the *Cannabis* concentrate can include a therapeutically effective amount of Δ(9)-tetrahydrocannabinol (Δ(9)-THC).

In specific embodiments, the *Cannabis* concentrate can be enriched in Δ(9)-tetrahydrocannabinolic acid (Δ(9)-THCA). In additional specific embodiments, the *Cannabis* concentrate can include a therapeutically effective amount of Δ(9)-tetrahydrocannabinolic acid (Δ(9)-THCA).

In specific embodiments, the *Cannabis* concentrate can be enriched in Δ(9)-cannabidiol (Δ(9)-CBD). In additional specific embodiments, the *Cannabis* concentrate can include a therapeutically effective amount of Δ(9)-cannabidiol (Δ(9)-CBD).

In specific embodiments, the *Cannabis* concentrate can be enriched in Δ(9)-tetrahydrocannabidiolic acid (Δ(9)-CBDA). In additional specific embodiments, the *Cannabis* concentrate can include a therapeutically effective amount of Δ(9)-tetrahydrocannabidiolic acid (Δ(9)-CBDA).

In specific embodiments, the *Cannabis* concentrate can be enriched in Δ(8)-tetrahydrocannabinol (Δ(8)-THC). In additional specific embodiments, the *Cannabis* concentrate can include a therapeutically effective amount of Δ(8)-tetrahydrocannabinol (Δ(8)-THC).

In specific embodiments, the *Cannabis* concentrate can be enriched in Δ(8)-tetrahydrocannabinolic acid (Δ(8)-THCA). In additional specific embodiments, the *Cannabis* concentrate can include a therapeutically effective amount of Δ(8)-tetrahydrocannabinolic acid (Δ(8)-THCA).

In specific embodiments, the *Cannabis* concentrate can be enriched in Δ(8)-tetrahydrocannabidiol (Δ(8)-CBD). In additional specific embodiments, the *Cannabis* concentrate can include a therapeutically effective amount of Δ(8)-tetrahydrocannabidiol (Δ(8)-CBD).

In specific embodiments, the *Cannabis* concentrate can be enriched in Δ(8)-tetrahydrocannabidiolic acid (Δ(8)-CBDA). In additional specific embodiments, the *Cannabis* concentrate can include a therapeutically effective amount of Δ(8)-tetrahydrocannabidiolic acid (Δ(8)-CBDA).

In specific embodiments, the *Cannabis* concentrate can be enriched in Δ(9)-tetrahydrocannabivarin (Δ(9)-THV). In additional specific embodiments, the *Cannabis* concentrate can include a therapeutically effective amount of Δ(9)-tetrahydrocannabivarin (Δ(9)-THV).

In specific embodiments, the *Cannabis* concentrate can be enriched in cannabigerol (CBG). In additional specific embodiments, the *Cannabis* concentrate can include a therapeutically effective amount of cannabigerol (CBG).

In specific embodiments, the *Cannabis* concentrate can be enriched in cannabigerolic acid (CBGA). In additional specific embodiments, the *Cannabis* concentrate can include a therapeutically effective amount of cannabigerolic acid (CBGA).

In specific embodiments, the *Cannabis* concentrate can be enriched in cannabichromene (CBC). In additional specific embodiments, the *Cannabis* concentrate can include a therapeutically effective amount of cannabichromene (CBC).

In specific embodiments, the *Cannabis* concentrate can be enriched in cannabichromenic acid (CBCA). In additional specific embodiments, the *Cannabis* concentrate can include a therapeutically effective amount of cannabichromenic acid (CBCA).

In specific embodiments, the *Cannabis* concentrate can be enriched in cannabicyclol (CBL). In additional specific embodiments, the *Cannabis* concentrate can include a therapeutically effective amount of cannabicyclol (CBL).

In specific embodiments, the *Cannabis* concentrate can be enriched in cannabicyclolic acid (CBLA). In additional specific embodiments, the *Cannabis* concentrate can include a therapeutically effective amount of cannabicyclolic acid (CBLA).

In specific embodiments, the *Cannabis* concentrate can be enriched in β-caryophyllene epoxide. In additional specific embodiments, the *Cannabis* concentrate can include a therapeutically effective amount of β-caryophyllene epoxide.

In specific embodiments, the *Cannabis* concentrate can be enriched in mentha-1,8(9)-dien-5-ol. In additional specific embodiments, the *Cannabis* concentrate can include a therapeutically effective amount of mentha-1,8(9)-dien-5-ol.

In specific embodiments, the *Cannabis* concentrate can be enriched in pulegone. In additional specific embodiments, the *Cannabis* concentrate can include a therapeutically effective amount of pulegone.

In specific embodiments, the *Cannabis* concentrate can be enriched in limonene. In additional specific embodiments, the *Cannabis* concentrate can include a therapeutically effective amount of limonene.

In specific embodiments, the *Cannabis* concentrate can be enriched in limonene oxide. In additional specific embodiments, the *Cannabis* concentrate can include a therapeutically effective amount of limonene oxide.

In specific embodiments, the *Cannabis* concentrate can be enriched in α-terpinene. In additional specific embodiments, the *Cannabis* concentrate can include a therapeutically effective amount of α-terpinene.

In specific embodiments, the *Cannabis* concentrate can be enriched in terpinen-4-ol. In additional specific embodiments, the *Cannabis* concentrate can include a therapeutically effective amount of terpinen-4-ol.

In specific embodiments, the *Cannabis* concentrate can be enriched in carvacrol. In additional specific embodiments, the *Cannabis* concentrate can include a therapeutically effective amount of carvacrol.

In specific embodiments, the *Cannabis* concentrate can be enriched in carvone. In additional specific embodiments, the *Cannabis* concentrate can include a therapeutically effective amount of carvone.

In specific embodiments, the *Cannabis* concentrate can be enriched in 1,8-cineole. In additional specific embodiments, the *Cannabis* concentrate can include a therapeutically effective amount of 1,8-cineole.

In specific embodiments, the *Cannabis* concentrate can be enriched in p-cymene. In additional specific embodiments, the *Cannabis* concentrate can include a therapeutically effective amount of p-cymene.

In specific embodiments, the *Cannabis* concentrate can be enriched in fenchone. In additional specific embodiments, the *Cannabis* concentrate can include a therapeutically effective amount of fenchone.

In specific embodiments, the *Cannabis* concentrate can be enriched in pulegone-1,2epoxide. In additional specific embodiments, the *Cannabis* concentrate can include a therapeutically effective amount of pulegone-1,2epoxide.

In specific embodiments, the *Cannabis* concentrate can be enriched in β-myrcene. In additional specific embodiments, the *Cannabis* concentrate can include a therapeutically effective amount of β-myrcene.

In specific embodiments, the *Cannabis* concentrate can be enriched in cannaflavin A. In additional specific embodiments, the *Cannabis* concentrate can include a therapeutically effective amount of cannaflavin A.

In specific embodiments, the *Cannabis* concentrate can be enriched in cannaflavin B. In additional specific embodiments, the *Cannabis* concentrate can include a therapeutically effective amount of cannaflavin B.

In specific embodiments, relative to the *Cannabis* plant material, the *Cannabis* concentrate can include a higher concentration of cannabinol (CBN). In alternative specific embodiments, relative to the *Cannabis* plant material, the *Cannabis* concentrate can include a lower concentration of cannabinol (CBN).

In specific embodiments, relative to the *Cannabis* plant material, the *Cannabis* concentrate can include a higher concentration of cannabinolic acid (CBNA). In alternative specific embodiments, relative to the *Cannabis* plant material, the *Cannabis* concentrate can include a lower concentration of cannabinolic acid (CBNA).

In specific embodiments, relative to the *Cannabis* plant material, the *Cannabis* concentrate can include a higher concentration of Δ(9)-tetrahydrocannabinol (Δ(9)-THC). In alternative specific embodiments, relative to the *Cannabis* plant material, the *Cannabis* concentrate can include a lower concentration of Δ(9)-tetrahydrocannabinol (Δ(9)-THC).

In specific embodiments, relative to the *Cannabis* plant material, the *Cannabis* concentrate can include a higher concentration of Δ(9)-tetrahydrocannabinolic acid (Δ(9)-THCA). In alternative specific embodiments, relative to the *Cannabis* plant material, the *Cannabis* concentrate can include a lower concentration of Δ(9)-tetrahydrocannabinolic acid (Δ(9)-THCA).

In specific embodiments, relative to the *Cannabis* plant material, the *Cannabis* concentrate can include a higher concentration of Δ(9)-cannabidiol (Δ(9)-CBD). In alternative specific embodiments, relative to the *Cannabis* plant material, the *Cannabis* concentrate can include a lower concentration of Δ(9)-cannabidiol (Δ(9)-CBD).

In specific embodiments, relative to the *Cannabis* plant material, the *Cannabis* concentrate can include a higher concentration of Δ(9)-tetrahydrocannabidiolic acid (Δ(9)-CBDA). In specific embodiments, relative to the *Cannabis* plant material, the *Cannabis* concentrate can include a lower concentration of Δ(9)-tetrahydrocannabidiolic acid (Δ(9)-CBDA).

In specific embodiments, relative to the *Cannabis* plant material, the *Cannabis* concentrate can include a higher concentration of Δ(8)-tetrahydrocannabinol (Δ(8)-THC). In specific embodiments, relative to the *Cannabis* plant material, the *Cannabis* concentrate can include a lower concentration of Δ(8)-tetrahydrocannabinol (Δ(8)-THC).

In specific embodiments, relative to the *Cannabis* plant material, the *Cannabis* concentrate can include a higher concentration of Δ(8)-tetrahydrocannabinolic acid (Δ(8)-THCA). In specific embodiments, relative to the *Cannabis* plant material, the *Cannabis* concentrate can include a lower concentration of Δ(8)-tetrahydrocannabinolic acid (Δ(8)-THCA).

In specific embodiments, relative to the *Cannabis* plant material, the *Cannabis* concentrate can include a higher concentration of Δ(8)-tetrahydrocannabidiol (Δ(8)-CBD). In specific embodiments, relative to the *Cannabis* plant material, the *Cannabis* concentrate can include a lower concentration of Δ(8)-tetrahydrocannabidiol (Δ(8)-CBD).

In specific embodiments, relative to the *Cannabis* plant material, the *Cannabis* concentrate can include a higher concentration of Δ(8)-tetrahydrocannabidiolic acid (Δ(8)-CBDA). In specific embodiments, relative to the *Cannabis* plant material, the *Cannabis* concentrate can include a lower concentration of Δ(8)-tetrahydrocannabidiolic acid (Δ(8)-CBDA).

In specific embodiments, relative to the *Cannabis* plant material, the *Cannabis* concentrate can include a higher concentration of Δ(9)-tetrahydrocannabivarin (Δ(9)-THV). In specific embodiments, relative to the *Cannabis* plant material, the *Cannabis* concentrate can include a lower concentration of Δ(9)-tetrahydrocannabivarin (Δ(9)-THV).

In specific embodiments, relative to the *Cannabis* plant material, the *Cannabis* concentrate can include a higher concentration of cannabigerol (CBG). In specific embodiments, relative to the *Cannabis* plant material, the *Cannabis* concentrate can include a lower concentration of cannabigerol (CBG).

In specific embodiments, relative to the *Cannabis* plant material, the *Cannabis* concentrate can include a higher concentration of cannabigerolic acid (CBGA). In specific embodiments, relative to the *Cannabis* plant material, the *Cannabis* concentrate can include a lower concentration of cannabigerolic acid (CBGA).

In specific embodiments, relative to the *Cannabis* plant material, the *Cannabis* concentrate can include a higher concentration of cannabichromene (CBC). In alternative specific embodiments, relative to the *Cannabis* plant material, the *Cannabis* concentrate can include a lower concentration of cannabichromene (CBC).

In specific embodiments, relative to the *Cannabis* plant material, the *Cannabis* concentrate can include a higher concentration of cannabichromenic acid (CBCA). In alternative specific embodiments, relative to the *Cannabis* plant material, the *Cannabis* concentrate can include a lower concentration of cannabichromenic acid (CBCA).

In specific embodiments, relative to the *Cannabis* plant material, the *Cannabis* concentrate can include a higher concentration of cannabicyclol (CBL). In alternative specific embodiments, relative to the *Cannabis* plant material, the *Cannabis* concentrate can include a lower concentration of cannabicyclol (CBL).

In specific embodiments, relative to the *Cannabis* plant material, the *Cannabis* concentrate can include a higher concentration of cannabicyclolic acid (CBLA). In alternative specific embodiments, relative to the *Cannabis* plant material, the *Cannabis* concentrate can include a lower concentration of cannabicyclolic acid (CBLA).

In specific embodiments, relative to the *Cannabis* plant material, the *Cannabis* concentrate can include a higher concentration of β-caryophyllene epoxide. In alternative specific embodiments, relative to the *Cannabis* plant material, the *Cannabis* concentrate can include a lower concentration of β-caryophyllene epoxide.

In specific embodiments, relative to the *Cannabis* plant material, the *Cannabis* concentrate can include a higher concentration of mentha-1,8(9)-dien-5-ol. In alternative specific embodiments, relative to the *Cannabis* plant material, the *Cannabis* concentrate can include a lower concentration of mentha-1,8(9)-dien-5-ol.

In specific embodiments, relative to the *Cannabis* plant material, the *Cannabis* concentrate can include a higher concentration of pulegone. In alternative specific embodiments, relative to the *Cannabis* plant material, the *Cannabis* concentrate can include a lower concentration of pulegone.

In specific embodiments, relative to the *Cannabis* plant material, the *Cannabis* concentrate can include a higher concentration of limonene. In alternative specific embodiments, relative to the *Cannabis* plant material, the *Cannabis* concentrate can include a lower concentration of limonene.

In specific embodiments, relative to the *Cannabis* plant material, the *Cannabis* concentrate can include a higher concentration of limonene oxide. In alternative specific embodiments, relative to the *Cannabis* plant material, the *Cannabis* concentrate can include a lower concentration of limonene oxide.

In specific embodiments, relative to the *Cannabis* plant material, the *Cannabis* concentrate can include a higher concentration of α-terpinene. In alternative specific embodiments, relative to the *Cannabis* plant material, the *Cannabis* concentrate can include a lower concentration of α-terpinene.

In specific embodiments, relative to the *Cannabis* plant material, the *Cannabis* concentrate can include a higher concentration of terpinen-4-ol. In alternative specific embodiments, relative to the *Cannabis* plant material, the *Cannabis* concentrate can include a lower concentration of terpinen-4-ol.

In specific embodiments, relative to the *Cannabis* plant material, the *Cannabis* concentrate can include a higher concentration of carvacrol. In alternative specific embodiments, relative to the *Cannabis* plant material, the *Cannabis* concentrate can include a lower concentration of carvacrol.

In specific embodiments, relative to the *Cannabis* plant material, the *Cannabis* concentrate can include a higher concentration of carvone. In alternative specific embodiments, relative to the *Cannabis* plant material, the *Cannabis* concentrate can include a lower concentration of carvone.

In specific embodiments, relative to the *Cannabis* plant material, the *Cannabis* concentrate can include a higher concentration of 1,8-cineole. In alternative specific embodiments, relative to the *Cannabis* plant material, the *Cannabis* concentrate can include a lower concentration of 1,8-cineole.

In specific embodiments, relative to the *Cannabis* plant material, the *Cannabis* concentrate can include a higher concentration of p-cymene. In alternative specific embodiments, relative to the *Cannabis* plant material, the *Cannabis* concentrate can include a lower concentration of p-cymene.

In specific embodiments, relative to the *Cannabis* plant material, the *Cannabis* concentrate can include a higher concentration of fenchone. In alternative specific embodiments, relative to the *Cannabis* plant material, the *Cannabis* concentrate can include a lower concentration of fenchone.

In specific embodiments, relative to the *Cannabis* plant material, the *Cannabis* concentrate can include a higher concentration of pulegone-1,2epoxide. In alternative specific embodiments, relative to the *Cannabis* plant material, the *Cannabis* concentrate can include a lower concentration of pulegone-1,2epoxide.

In specific embodiments, relative to the *Cannabis* plant material, the *Cannabis* concentrate can include a higher concentration of β-myrcene. In alternative specific embodiments, relative to the *Cannabis* plant material, the *Cannabis* concentrate can include a lower concentration of β-myrcene.

In specific embodiments, relative to the *Cannabis* plant material, the *Cannabis* concentrate can include a higher concentration of cannaflavin A. In alternative specific embodiments, relative to the *Cannabis* plant material, the *Cannabis* concentrate can include a lower concentration of cannaflavin A.

In specific embodiments, relative to the *Cannabis* plant material, the *Cannabis* concentrate can include a higher concentration of cannaflavin B. In alternative specific embodiments, relative to the *Cannabis* plant material, the *Cannabis* concentrate can include a lower concentration of cannaflavin B.

In specific embodiments, relative to the *Cannabis* plant material, the *Cannabis* concentrate can include a higher concentration of cannabinoids. In additional specific embodiments, relative to the *Cannabis* plant material, the *Cannabis* concentrate can include a lower concentration of terpenoids. In further specific embodiments, relative to the *Cannabis* plant material, the *Cannabis* concentrate can include a higher concentration of cannabinoids and a lower concentration of terpenoids.

In specific embodiments, relative to the *Cannabis* plant material, the *Cannabis* concentrate can include a lower concentration of cannabinoids. In additional specific embodiments, relative to the *Cannabis* plant material, the *Cannabis* concentrate can include a higher concentration of terpenoids. In further specific embodiments, relative to the *Cannabis* plant material, the *Cannabis* concentrate can include a lower concentration of cannabinoids and a higher concentration of terpenoids.

Active Pharmaceutical Ingredient (API)

As described herein, the SFE (or FSFE) can be used to remove unwanted material (e.g. terpenes, alkaloids, hemp oil, and/or cannabinoid acids) from *Cannabis* plant material. Additionally, the SFE (or FSFE) can be used to obtain a desired product (e.g. cannabinoids, terpenoids, and/or flavonoids) from the *Cannabis* plant material. Exemplary desired products naturally present in *Cannabis* are illustrated in the table below.

| Chemical Name | Structural Formula | Solubility |
| --- | --- | --- |
| cannabinol (CBN) | | insol. water; sol. MeOH, EtOH, lipids, non-polar organic solvents |
| cannabinolic acid (CBNA) | | sol water, alkaline solutions; sol. alcohols Water Solubility Estimate from Log Kow (WSKOW v1.41): Water Solubility at 25° C. (mg/L): 0.001206 |
| Δ(9)-tetrahydrocannabinol (Δ(9)-THC) | | 0.0028 mg/mL (23° C.) water sol. MeOH, EtOH sol. lipids sol. non-polar organic solvents |
| Δ(9)-tetrahydrocannabinolic acid (Δ(9)-THCA) | | sol water, alkaline solutions; sol. alcohols |

-continued

| Chemical Name | Structural Formula | Solubility |
|---|---|---|
| Δ(9)-cannabidiol (Δ(9)-CBD) | | insol. water<br>sol. pentane |
| Δ(9)-tetrahydrocannabidiolic acid (Δ(9)-CBDA) | | sol water, alkaline solutions;<br>sol. alcohols |
| Δ(8)-tetrahydrocannabinol (Δ(8)-THC) | | insol. water<br>sol. MeOH, EtOH<br>sol. lipids<br>sol. non-polar organic solvents |
| Δ(8)-tetrahydrocannabinolic acid (Δ(8)-THCA) | | sol water, alkaline solutions;<br>sol. alcohols |
| Δ(8)-tetrahydrocannabidiol (Δ(8)-CBD) | | insol. water<br>sol. pentane |
| Δ(8)-tetrahydrocannabidiolic acid (Δ(8)-CBDA) | | sol water, alkaline solutions;<br>sol. alcohols |
| Δ(9)-tetrahydrocannabivarin (Δ(9)-THV) | | sol water, alkaline solutions;<br>sol. alcohols |

-continued

| Chemical Name | Structural Formula | Solubility |
|---|---|---|
| cannabigerol (CBG) | 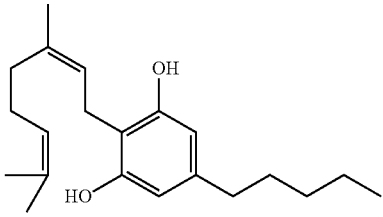 [SMILES: CCCCCc1cc(O)c(C/C=C(/C)CCC=C(C)C)c(O)c1] | insol. water<br>Water Solubility<br>Estimate from Log Kow<br>(WSKOW v1.41): Water<br>Solubility at 25° C.<br>(mg/L): 0.003756<br>sol. pentane |
| cannabigerolic acid (CBGA) | 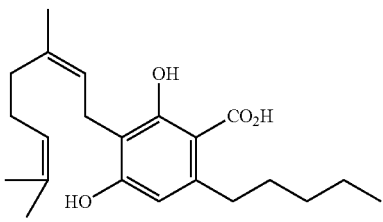 [SMILES: CCCCCc1cc(O)c(C/C=C(/C)CCC=C(C)C)c(O)c1C(=O)O] | sol water, alkaline solutions;<br>sol. alcohols; |
| cannabichromene (CBC) | 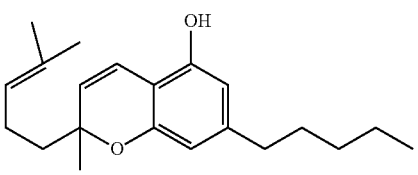 [SMILES: CCCCCc1cc(O)c2c(c1)OC(C)(CCC=C(C)C)C=C2] | insol. water<br>sol. pentane |
| cannabichromenic acid (CBCA) | 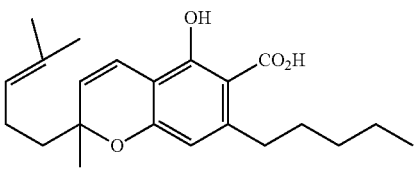 [SMILES: CCCCCc1cc2c(c(O)c1C(=O)O)C=CC(C)(CCC=C(C)C)O2] | sol water, alkaline solutions;<br>sol. alcohols |
| cannabicyclol (CBL) | 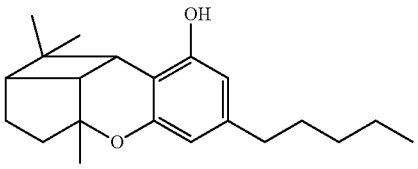 [SMILES: CCCCCc1cc(O)c2c(c1)OC1(C)CCC3C1C2C3(C)C] | insol. water<br>sol. pentane |
| cannabicyclolic acid (CBLA) | 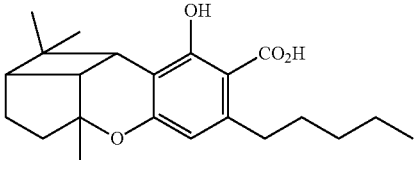 [SMILES: CCCCCc1cc2c(c(O)c1C(=O)O)C1C3C(CCC3(C)O2)C1(C)C] | sol water, alkaline solutions;<br>sol. alcohols |
| β-caryophyllene epoxide | 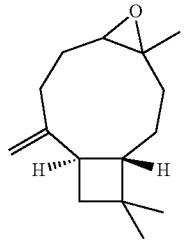 | insol. water<br>sol. alcohols, organic solvents (ethers, halocarbons) |

-continued

| Chemical Name | Structural Formula | Solubility |
| --- | --- | --- |
| mentha-1,8(9)-dien-5-ol | | insol. water<br>sol. alcohols, organic solvents (ethers, halocarbons) |
| pulegone | | insol. water<br>sol. alcohols, organic solvents (ethers, halocarbons) |
| limonene | | insol. water<br>sol. alcohols, organic solvents (ethers, halocarbons), hydrocarbons |
| limonene oxide | | insol. water<br>sol. alcohols, organic solvents (ethers, halocarbons) |
| α-terpinene | | insol. water<br>sol. alcohols, organic solvents (ethers, halocarbons), hydrocarbons |
| terpinen-4-ol | | insol. water<br>sol. alcohols, organic solvents (ethers, halocarbons) |
| carvacrol | | sp. sol. water<br>sol. alcohols, organic solvents (ethers, halocarbons) |

-continued

| Chemical Name | Structural Formula | Solubility |
| --- | --- | --- |
| carvone | | insol. water<br>sol. alcohols, organic solvents (ethers, halocarbons) |
| 1,8-cineole | | insol. water<br>sol. alcohols, organic solvents (ethers, halocarbons) |
| p-cymene | | insol. water<br>sol. alcohols, organic solvents (ethers, halocarbons), hydrocarbons |
| fenchone | | insol. water<br>sol. alcohols, organic solvents (ethers, halocarbons) |
| pulegone-1,2epoxide | | insol. water<br>sol. alcohols, organic solvents (ethers, halocarbons) |
| β-myrcene | | insol. water<br>sol. alcohols, organic solvents (ethers, halocarbons), hydrocarbons |
| cannaflavin A | | insol. water<br>sol. alkalai<br>sol. alcohols, ethers, halocarbons |

| Chemical Name | Structural Formula | Solubility |
| --- | --- | --- |
| cannaflavin B | | insol. water<br>sol. alkalai<br>sol. alcohols, ethers, halocarbons |

Oral Thin Film (OTF)

The OTF includes a *Cannabis* concentrate. Formulation of oral thin films involves the application of both aesthetic and performance characteristics, such as, e.g., strip-forming polymers, plasticizers, active pharmaceutical ingredient, sweetening agents, saliva stimulating agent, flavoring agents, coloring agents, stabilizing and thickening agents. From the regulatory perspectives, all excipients used in the formulation of oral drug strips should be approved for use in oral pharmaceutical dosage forms.

The substances can be selected in an amount such that a desired dissolution rate can be targeted. Upon contact with mucosal tissue (including, e.g., oral mucosa) the TF will completely dissolve within the desired period of time. The period of time will vary but in reference to the oral cavity, the period of time will typically be within about 30-300 seconds.

The OTF can be placed on any suitable surface within the mouth (oral mucosa), including the roof of the mouth, cheek, tongue, and under the tongue (sublingual mucosa).

Dissolving films generally fall into three main classes: fast dissolving, moderate dissolving and slow dissolving. Fast dissolving films generally dissolve in about 1 second to about 30 seconds. Moderate dissolving films generally dissolve in about 1 to about 30 minutes, and slow dissolving films generally dissolve in more than 30 minutes.

The thin film can be manufactured in a manner, employing suitable ingredients, such that any one or more of the desired pharmacokinetic metrics (e.g., dose, area under the curve, peak plasma concentration, dosing intervals, time to reach peak plasma concentration, clearance, bioavailability, etc.) are achieved. For example, the thin film can be manufactured such that the thin film provides for an immediate release (IR) or a time-release (e.g., controlled release (CR), modified release (MR), extended release (ER), or combination thereof) of active ingredient. The thin films described herein therefore possess the potential to allow the development of sensitive drug targets that may otherwise not be feasible in tablet or liquid formulations.

The thin film described herein can include a mucoadhesive agent. The mucoadhesive agent, when placed in the oral cavity in contact with the mucosa therein, adheres to the mucosa. The mucoadhesive agent is especially effective in transmucosal delivery of the active ingredient, as the mucoadhesive agent permits a close and extended contact of the composition with the mucosal surface by promoting adherence of the composition or drug to the mucosa, and facilitates the release of the active ingredient from the composition. The mucoadhesive agent can be a polymeric compound, such as a cellulose derivative but it may be also a natural gum, alginate, pectin, or such similar polymer. The concentration of the mucoadhesive agent in the coating, such as a powder matrix coating, may be adjusted to vary the length of time that the film adheres to the mucosa or to vary the adhesive forces generated between the film and mucosa. The mucoadhesive agent may adhere to oral mucosa or to mucosa or tissue in other parts of the body, including the mouth, nose, eyes, vagina, and rectum.

Mucoadhesive agents include, e.g., carboxymethyl cellulose, polyvinyl alcohol, polyvinyl pyrrolidone (povidone), sodium alginate, methyl cellulose, hydroxypropyl cellulose, hydroxypropyl methyl cellulose, polyethylene glycols, carbopols, polycarbophils, carboxyvinyl copolymers, propylene glycol alginate, alginic acid, methyl methacrylate copolymers, tragacanth gum, guar gum, karaya gum, ethylene vinyl acetate, dimenthylpolysiloxanes, polyoxyalkylene block copolymers, pectin, chitosan, carrageenan, xanthan gum, gellan gum, locust bean gum, and hydroxyethylmethacrylate copolymers.

The thin film described herein can include a flavoring agent. "Flavoring agent" refers to a substance capable of providing a flavor. In addition to providing a palatable and pleasurable factor to the user, the flavoring agent can also mask undesirable flavors present in the OTF. The flavoring agent can include natural flavoring agents (e.g., extracts).

The thin film described herein can include a flavoring extract. "Flavor extract" refers to a flavoring agent obtained by extracting a part of a raw material, e.g., animal or plant material, often by using a solvent such as ethanol or water. The majority of natural essences are obtained by extracting the essential oil from the blossoms, fruit, roots, etc., or the whole plants, through four techniques: expression (when the oil is very plentiful and easily obtained, as in lemon peel), absorption (generally accomplished by steeping in alcohol, as vanilla beans), maceration (used to create smaller bits of the whole, as in making peppermint extract, etc.), and distillation (used with maceration, but in many cases, it requires expert chemical knowledge and the erection of costly stills).

Flavoring agents can include breath freshening compounds like menthol, spearmint, and cinnamon, coffee beans, other flavors or fragrances such as fruit (e.g., cherry, orange, grape, etc.) flavors, especially those used for oral hygiene, as well as actives used in dental and oral cleansing such as quaternary ammonium bases. The effect of flavors may be enhanced using flavor enhancers like tartaric acid, citric acid, vanillin, or the like.

The thin film described herein can include a sweetener. "Sweetener" refers to a substance capable of providing a palatable and pleasurable factor to the user, and/or capable of masking undesirable flavors present in the OTF. The sweetener can include one or more artificial sweeteners, one or more natural sweeteners, or a combination thereof.

Artificial sweeteners include, e.g., acesulfame and its various salts such as the potassium salt (available as Sunett®), alitame, aspartame (available as NutraSweet® and Equal®), salt of aspartame-acesulfame (available as Twinsweet®), neohesperidin dihydrochalcone, naringin dihydrochalcone, dihydrochalcone compounds, neotame, sodium cyclamate, saccharin and its various salts such as the sodium salt (available as Sweet'N Low®), stevia, chloro derivatives of sucrose such as sucralose (available as Kaltame® and Splenda®), and mogrosides.

Natural sweeteners include, e.g., glucose, dextrose, invert sugar, fructose, sucrose, glycyrrhizin; monoammonium glycyrrhizinate (sold under the trade name MagnaSweet®); Stevia rebaudiana (Stevioside), natural intensive sweeteners, such as Lo Han Kuo, polyols such as sorbitol, mannitol, xylitol, erythritol, and the like.

The thin film described herein can include a bitter blocker. "Bitter blocker" refers to a substance capable of blocking or diminishing the bitter taste of another substance.

In specific embodiments, the thin film described can be palatable. "Palatable" refers to a substance (e.g., oral thin film) being relatively acceptable or agreeable to the palate or taste (e.g., sweet or savory), and in some cases to the olfactory nerves.

The thin film described herein can include a dye, pigment or coloring agent. "Dye or pigment" or "coloring agent" refers to a substance that imparts coloring and/or aesthetic appearance to the OTF. A dye is a colored substance that has an affinity to the substrate to which it is being applied. The dye is generally applied in an aqueous solution, and requires a mordant to improve the fastness of the dye on the fiber. A pigment is a material that changes the color of reflected or transmitted light as the result of wavelength-selective absorption. This physical process differs from fluorescence, phosphorescence, and other forms of luminescence, in which a material emits light. Both dyes and pigments appear to be colored because they absorb some wavelengths of light more than others. In contrast with a dye, a pigment generally is insoluble, and has no affinity for the substrate. Some dyes can be precipitated with an inert salt to produce a lake pigment, and based on the salt used they could be aluminum lake, calcium lake or barium lake pigments.

One or more dyes, pigments, and coloring agents can be employed in the manufacture of the thin film, such that the thin film has the desired color. Suitable colors include, e.g., white, black, yellow, blue, green, pink, red, orange, violet, indigo, and brown. In specific embodiments, the color of the thin film can indicate the contents (e.g., one or more active ingredients) contained therein.

In specific embodiments, the thin film described herein can include a preservative. "Preservative" refers to an agent that extends the storage life of food and non-food products by retarding or preventing deterioration of flavor, odor, color, texture, appearance, nutritive value, or safety. A preservative need not provide a lethal, irreversible action resulting in partial or complete microbial cell destruction or incapacitation. Sterilants, sanitizers, disinfectants, sporicides, viracides and tuberculocidal agents provide such an irreversible mode of action, sometimes referred to as "bactericidal" action. In contrast, a preservative can provide an inhibitory or bacteriostatic action that is reversible, in that the target microbes can resume multiplication if the preservative is removed. The principal differences between a preservative and a sanitizer primarily involve mode of action (a preservative prevents growth rather than killing microorganisms) and exposure time (a preservative has days to months to act whereas a sanitizer has at most a few minutes to act).

In specific embodiments, the thin film described herein can have a suitable tensile strength. "Tensile strength" refers to the maximum stress that a material can withstand while being stretched or pulled before failing or breaking Tensile strength is the opposite of compressive strength and the values can be quite different. Tensile strength is defined as a stress, which is measured as force per unit area. For some non-homogeneous materials (or for assembled components) it can be reported just as a force or as a force per unit width. In the SI system, the unit is the pascal (Pa) (or a multiple thereof, often megapascals (MPa), using the mega-prefix); or, equivalently to pascals, newtons per square meter ($N/m^2$). The customary unit is pounds-force per square inch ($lbf/in^2$ or psi), or kilo-pounds per square inch (ksi, or sometimes kpsi), which is equal to 1000 psi; kilo-pounds per square inch are commonly used for convenience when measuring tensile strengths. Typically, the testing involves taking a small sample with a fixed cross-section area, and then pulling it with a controlled, gradually increasing force until the sample changes shape or breaks.

In specific embodiments, the thin film described herein can be pliable. "Pliable" refers to the ability of an article to readily bend, be flexible, or to be supple.

In specific embodiments, the thin film described herein can be non-sticky. "Non-sticky" refers to an article (e.g., thin film) not having the property of readily adhering or sticking to another surface (e.g., another article, manufacturing equipment, packaging material, the user, etc.) while not in use.

In specific embodiments, the thin film described herein can be soft. "Soft" refers to an article being relatively smooth and agreeable to the touch; not rough or coarse. Such an article will be capable of producing agreeable sensations, pleasant or comfortable, upon contact with an animal such as a human.

In specific embodiments, the thin film described herein can have chewable configuration. "Chewable configuration" refers to an article being manufactured in such a manner and with ingredients, that it possesses a configuration capable of being readily chewed by an animal, such as a human.

In specific embodiments, the thin film described herein can have a malleable configuration. "Malleable configuration" refers to refers to an article being manufactured in such a manner and with ingredients, that it possesses a configuration capable of being readily shaped or changed in form (e.g., folded, bent, rolled, twisted, flexed, etc.) without breaking.

In specific embodiments, the thin film described herein can have a ductile property. "Ductile property" refers to the ability of an article (e.g., thin film) being readily shaped or changed in form (e.g., folded, bent, rolled, twisted, flexed, etc.) without breaking.

In specific embodiments, the thin films described herein can be perforated. "Perforated" refers to the one or more holes, apertures or scores existing along a line to facilitate separation. Perforations on the thin films allow the user to conveniently administer smaller dosages of the active ingredient. This is especially useful, for example, when the patient is a child, who should receive a smaller dosage. Accurate dosing can be metered, e.g., by the weight, size, age, etc. of the patient.

The OTF serves as an alternative dosage form for patients who experience dysphagia (difficulty in swallowing) or for where compliance is a known issue and therefore an easier dosage form to take ensures that medication is taken. Additional reasons (and advantages) to use OTFs include the convenience of a dosage form that can be taken without water as well as the inability of the patient to eat or drink (e.g., experiencing nausea and/or vomiting).

Suitable oral thin films, and methods of preparing oral thin films, are described, e.g., in WO/2012/103464A2; WO/2013/085224A1; US 2013/0039955; US 2011/0305768; WO/2011/072208A1; US 2011/0142942; US 2013/0309294; WO/2012/104834A1; US 2012/0125351; and US 2011/0280925.

Transdermal Patch

The topical adhesive patch includes a backing having a front side and a back side. The patch includes a formulation that is in contact with the front side of the backing. The formulation includes an adhesive and *Cannabis* concentrate.

Since the backing can be porous and/or vapor permeable, many consumers typically refer to the device as a "patch," a "skin patch," a "topical patch," or an "adhesive skin patch." As such, the device will herein be referred interchangeably to as a patch, a skin patch, and/or an adhesive skin patch. It is appreciated that those skilled in the art understand that the term "patch" is used to refer to the device and is not otherwise limiting in any manner.

The topical adhesive patch can be manufactured in a manner, employing suitable ingredients, such that any one or more of the desired pharmacokinetic metrics (e.g., dose, area under the curve, peak plasma concentration, dosing intervals, time to reach peak plasma concentration, clearance, bioavailability, etc.) are achieved. For example, the topical adhesive patch can be manufactured such that the topical adhesive patch provides for an immediate release (IR) or a time-release (e.g., controlled release (CR), modified release (MR), extended release (ER), or combination thereof) of active ingredient. The topical adhesive patch described herein therefore possess the potential to allow the development of sensitive drug targets that may otherwise not be feasible in tablet or liquid formulations.

Backing

The backing is defined by a front side (the side exposed to the subject, or an article of clothing of the subject, during use) and a back side (the side exposed to the environment during use). The backing should be nonirritating to human skin. The backing is a self-supporting sheet of water soluble or water insoluble, polymeric or natural material that provides strength and integrity for the formulation. The backing of the adhesive patch can be vapor permeable. The backing can also be porous, since porosity provides openings for receiving the formulation, and it helps to assure that the adhesive skin patch is vapor permeable. Specifically, the backing can retain the formulation while allowing moisture from the skin to pass. Alternatively, the backing can be non-porous. The backing can have any suitable thickness. In specific embodiments, the suitable thickness allows for a flexible, bendable, pliable, vapor permeable, and/or a stretchable sheet of water insoluble porous material. Specifically, the thickness of the backing can be about 0.001 mm to about 5.0 mm, about 0.001 mm to about 3.0 mm, or about 0.025 mm to about 1.25 mm.

The backing can be manufactured from any suitable material. In specific embodiments, the suitable material forms a flexible, bendable, pliable, and/or stretchable backing. The backing includes a porous or non-porous sheet of water soluble or water insoluble material that provides support for the adhesive skin patch. The backing can include water soluble or water insoluble polymeric fibers, a porous film, or any other kind of matrix with spaces within the matrix. A specific backing is a lightweight, porous, pliable strip composed of a nonwoven fabric of polymeric or natural fibers such as polyester, cotton, or cellulose fibers bonded together with a sizing resin. The backing can be woven or nonwoven. In one embodiment, the backing includes nonwoven fabric. Specifically, the backing can include polyester fibers, polyurethane fibers, polyolefin fibers, polyamide fibers, natural fibers, cotton fibers, copolyester, copolyester fibers, cellulose acetate fibers, polycellulose fibers, or any mixture thereof. Additional stable, water insoluble flexible sheet materials and methods for manufacturing the suitable backings 2 are disclosed, e.g., in U.S. Pat. Nos. 4,675,009; 5,536,263; 4,696,854; 5,741,510; and references cited therein, and are suitable as backings 2 according to the present invention. The infusion of the formulation into the backing can be accomplished, e.g., with the use of a continuous process mixer, as disclosed, e.g., in U.S. Pat. No. 5,536,263, and references cited therein; or as discussed herein.

In a specific embodiment, the backing can be manufactured from a substance or substances that are generally recognized as safe (GRAS) for topical use.

The backing can be manufactured from a suitable nonwoven fabric that is commercially available from, e.g., Freudenberg Faservliesstoffe K G (Weinham, Germany); Sontara Technologies (division of DuPont Corporation) (Old Hickory, Tenn.); Lystil S. A. (Brignoud Cedex, France); Dexter Nonwovens (Windsor Locks, Conn.); Testfabrics, Inc. (West Pittiston, Pa.); and Chicopee (New Brusnwick, N.J.). Other commercial vendors that supply suitable nonwoven fabrics can be found at the Technical Textile website (http://www.technical-textiles.net/technical-textiles-index/orgL.htm).

Alternatively, the fibers of the backing can be interlocked mechanically by air or water.

The backing can include a front side and a back side. The adhesive skin patch can include a formulation located in at least a portion of the front side of the backing, on at least a portion of the front side of the backing, or on and in at least a portion of the front side of the backing. As such, the formulation can be located on the entire surface of the front side of the backing, or the formulation can be located on a portion of the surface of the front side of the backing.

In one embodiment, the formulation can be located on the entire surface of the front side of the backing. In addition to being located on the surface of the front side of the backing, the formulation can be located in at least a portion of the underlying surface of the front side of the backing (e.g., the formulation can be partially embedded into the backing).

The formulation can penetrate a substantial portion of the front side of the backing, as disclosed, e.g., in U.S. Pat. No. 5,536,263, and references cited therein. For example, the formulation can penetrate about one-tenth to about nine-tenths the thickness of the backing, or about one-fourth to about nine-tenths the thickness of the backing. As such, the formulation can be partially embedded into the backing. In one embodiment, the formulation can be located on the entire front side of the backing and partially in the front side of the backing (e.g., the formulation is partially embedded into the backing).

Alternatively, a portion of the front side of the backing can include the formulation and other portions of the front side of the backing can include any suitable and effective combination of the pressure sensitive adhesive and, optionally, the solvent. For example, a central circular portion of the front side of the backing can include the formulation while the remaining portions of the front side of the backing include only the pressure sensitive adhesive. The formulation, when partially embedded into the front side of the backing, can impart strength and structure into the adhesive patch. For example, when the formulation is partially embedded into the backing, the likelihood that the adhesive patch tears apart when separated from the release liner or when removed from the skin after use, is lowered.

When the adhesive skin patch is placed upon the skin of a subject (e.g., a human), the formulation can be in continuous contact with the skin surface of the subject.

In one embodiment, the adhesive skin patch, upon contact with skin, can allow the skin to breathe. In one embodiment, the adhesive skin patch, upon prolonged contact with skin, holds in place the formulation, and permits the skin to breathe over prolonged periods of time typically experienced with the use of the patch, e.g., up to about 7 days, up to about 24 hours, up to about 12 hours, up to about 8 hours, or up to about 6 hours.

The adhesive skin patch can be reversibly attached to a release liner. The release liner helps to maintain the adhesiveness of the adhesive skin patch prior to use, such as during manufacturing, packaging, shipping, and/or storage. Any suitable release liner can be employed for use in the present invention. Suitable release liners 10 are readily known to those of skill in the art. See, e.g., U.S. Pat. Nos. 4,675,009; 5,536,263; 4,696,854; 5,741,510; and references cited therein for further descriptions of release liners 10 useful in the present invention. The release liner can include a perforation that allows the tab section of the release liner to be removed. Removal of the tab section of the release liner can allow the adhesive skin patch to be removed from the release liner with relative ease.

The backing can be a porous or non-porous, self-supporting sheet of water insoluble or water soluble, polymeric or natural material that provides strength and integrity for the formulation. For example, the backing can be water insoluble polymeric fibers, open cell foam backing (e.g., polyurethane, polyvinyl chloride, or polyethylene), a porous film, or any other kind of matrix with spaces within the matrix. In one embodiment, the backing can include polyester, polyurethane, polyolefin, polyamide fibers, natural fibers, cotton fibers, polycellulose fibers, or any mixture thereof.

The back side of the backing of the patch can be relatively dry to the touch, such that upon contact, e.g., with a skin surface or article of clothing, no appreciable or significant amount of liquid, gel, ointment, fluid, lotion, and the like, present in the back side of the backing of the patch is transferred there from and deposited upon the skin surface or article of clothing.

The back side of the backing of the patch can have a relatively small degree of moisture, while still being considered a "dry" patch, and would still be relatively dry to the touch, such that upon contact, e.g., with a skin surface or article of clothing, no appreciable or significant amount of liquid, gel, ointment, fluid, lotion, and the like, present in the back side of the backing of the patch is transferred there from and deposited upon the skin surface or article of clothing.

In one embodiment, the back side of the backing of the patch can be relatively dry, upon touching.

Formulation

The patch can include a formulation that includes the Cannabis concentrate and adhesive, and optionally any one or more of a skin penetration enhancer, solvent, adhesive, polymer, humectant, topical moisturizer, polyhydric alcohol, and water.

The backing can include a front side and a back side. The patch can include a formulation located in at least a portion of the front side of the backing, located on at least a portion of the front side of the backing, or located on and in at least a portion of the front side of the backing. In one embodiment, the formulation is located on the entire front side of the backing and partially in the front side of the backing (e.g., the formulation is partially embedded into the backing).

The formulation can be positioned on and in any portion of the front side of the backing, i.e., the formulation can be positioned on at least a portion on the front side of the backing, in at least a portion on the front side of the backing, or on and in at least a portion on the front side of the backing. The formulation can be positioned in a portion of the front side of the backing (e.g., the formulation penetrates a substantial portion of the front side of the backing) as disclosed in, e.g., U.S. Pat. No. 5,536,263, and references cited therein. For example, the formulation can penetrate a substantial portion of the front side of the backing, e.g., typically between about one-fourth to about nine-tenths the thickness of the backing.

In one embodiment, the formulation can be positioned on the entire front side of the backing. In this latter configuration, the formulation is in continuous contact with the entire front side of the backing. When the adhesive skin patch is placed upon the skin surface of a subject, the formulation is in continuous contact with the skin surface of the subject.

Alternatively, a portion of the front side of the backing can contain the formulation and other portions of the front side of the backing can contain any combination of the adhesive, and, optionally, the solvent. For example, a central circular portion of the front side of the backing can contain the formulation while the remaining portions of the front side of the backing contains only the adhesive.

The formulation can include a *Cannabis* concentrate and an adhesive, and optionally one or more of the following components: a solvent, one or more polymers, a humectant, a topical moisturizer, and one or more polyhydric alcohols.

The formulation can remain stable over the period of time typically experienced with the manufacturing, packaging, shipping, and/or storage of the adhesive skin patch, e.g., up to about a month, up to about a year, or up to about two years.

Solvent

The solvent can act as a carrier for, and in one embodiment, can dissolve, the adhesive. Any suitable solvent can be employed, provided the solvent effectively and independently dissolves the adhesive, and the solvent remains stable in the formulation. In one embodiment, the stability is over a prolonged period of time, e.g., up to about 2 years, up to about 1 year, or up to about 6 months, typically experienced in the manufacturing, packaging, shipping, and/or storage of the patch.

The solvent can include one or more organic compounds, one or more inorganic compounds, or mixtures thereof. In one embodiment, the solvent will include one or more organic compounds, e.g., esters, alcohols, ketones, aldehydes, fatty acids, partially or fully esterified fatty acids, wherein the structures are cyclic, non-cyclic (e.g., alkyl), alicyclic (e.g., a bridged ring compound) or aromatic, as well as organic compounds having combinations of these functional groups. Suitable exemplary solvents are disclosed, e.g., in Aldrich Handbook of Fine Chemicals, 2000-2001 (Milwaukee, Wis.). In one embodiment, the solvent includes water (e.g., deionized water).

In one embodiment of the present invention, the solvent can include a ($C_1$-$C_{12}$) acyclic hydrocarbon, a ($C_3$-$C_{12}$) cyclic hydrocarbon, a ($C_6$-$C_{12}$) aryl hydrocarbon, a ($C_6$-$C_{12}$) heteroaryl hydrocarbon, or a ($C_3$-$C_{12}$) heterocyclic hydrocarbon;

wherein any of the hydrocarbons can optionally include one or more carbon-carbon double bonds and any of the hydrocarbons can optionally include one or more carbon-carbon triple bonds;

wherein any of the hydrocarbons can optionally include one or more oxy (—O—), carbonyl (—C(=O)C—), carboxylato (—C(=O)O—), dioxy (—O—O—), dithio (—S—S—), imino (—NH—), methylene dioxy (—OCH$_2$O—), sulfinyl (—SO—), sulfonyl (—SO$_2$—), or thio (—S—);

wherein any of the hydrocarbons can optionally be substituted with one or more amino, hydroxyl, cyano, nitro, ($C_1$-$C_{12}$)alkoxy, halo, trifluoro, trifluoro ($C_1$-$C_{12}$)alkyl, NR$^1$R$^2$, or COOR$^1$; wherein R$^1$ and R$^2$ are each independently hydrogen, a ($C_1$-$C_{12}$) acyclic hydrocarbon or a ($C_3$-$C_{12}$) cyclic hydrocarbon.

The solvent can be employed in any suitable amount, provided the amount of solvent is effective to independently dissolve the adhesive and the effective amount of solvent remains stable in the formulation. In one embodiment, the stability is over a prolonged period of time, e.g., up to about 2 years, up to about 1 year, or up to about 6 months, typically experienced in the manufacturing, packaging, shipping, and/or storage of the patch.

In a specific embodiment, the nature and amount of the solvent is selected, such that it will be generally recognized as safe (GRAS) for topical use.

Adhesive

Any suitable adhesive can be employed, provided the adhesive provides the requisite adhesiveness to the patch and the adhesive remains stable in the formulation. In one embodiment, the stability is over a prolonged period of time, e.g., up to about 2 years, up to about 1 year, or up to about 6 months, typically experienced in the manufacturing, packaging, shipping, and/or storage of the patch. It is appreciated that the suitable adhesives would be known to those skilled in the art. Suitable adhesives are disclosed, e.g., in U.S. Pat. No. 4,675,009; U.S. Pat. No. 5,536,263; U.S. Pat. No. 4,696,854; U.S. Pat. No. 5,741,510, and references cited therein. In one embodiment the adhesive is an acrylic ester copolymer.

Any suitable amount of adhesive can be employed, provided the amount of adhesive effectively provides the requisite adhesiveness to the patch and the effective amount of the adhesive remains stable in the formulation over a prolonged period of time. Typically, the suitable amount of adhesive depends upon the specific adhesive or adhesives employed. The formulation can include an adhesive in about 0.1 wt. % to about 50 wt. % of the formulation. In one embodiment, the formulation can include an adhesive in about 0.5 wt. % to about 10.0 wt. % of the formulation. In one embodiment, the formulation can include an adhesive in about 1.0 wt. % to about 15.0 wt. % of the formulation.

Alternatively, the adhesive can include a hot melt pressure sensitive adhesive or solvent based pressure sensitive adhesive (e.g., polyacrylate, polyisobutylene, and polybutene), rubber, silicone based pressure sensitive adhesives (e.g., polydimethylsiloxane and resin mixtures), polystyrene-polybutadiene-polystyrene, polystyrene-polyisoprene-polystyrene, polystyrene-poly(ethylene-butylene)-polystyrene block polymers, or any combination thereof. In addition, the adhesive can include a resin emulsion adhesive, wherein the resin emulsion adhesive can include vinyl acetate resin, acrylic ester copolymer, vinyl actetate/diocyl maleate copolymer, acrylic copolymer, or any combination thereof.

Other suitable adhesives are disclosed, e.g., in U.S. Pat. Nos. 4,675,009; 5,536,263; 4,696,854; 5,741,510; and references cited therein.

The adhesive can be located on and in any portion of the formulation. In one embodiment, the adhesive can be located on the entire skin contact side of the formulation. When the adhesive skin patch is placed upon the skin surface of a subject, the adhesive in this configuration is in continuous contact with the skin surface of the subject.

In a specific embodiment, the nature and amount of the adhesive is selected, such that it will be generally recognized as safe (GRAS) for topical use.

Polymers

The formulation can optionally include one or more polymers. The polymer provides structure and strength to the adhesive or can contain and release the active agent in a second formulation. Any suitable polymer can be employed, provided the polymer provides structure and strength to the adhesive and the polymer remains stable in the formulation. In one embodiment, the stability is over a prolonged period of time, e.g., up to about 2 years, up to about 1 year, or up to about 6 months, typically experienced in the manufacturing, packaging, shipping, and/or storage of the patch.

The suitable amount of polymer can depend upon the specific polymer or polymers employed. For example, gum karaya can be employed as the polymer in about 10 wt. % to about 55 wt. % of the formulation, in about 20 wt. % to about 35 wt. % of the formulation, or in about 23 wt. % to about 29 wt. % of the formulation. In one embodiment, gum karaya can be employed as the polymer in about 24 wt. % to about 28 wt. % of the formulation.

Suitable polymers include, e.g., starch, starch derivatives, polyvinyl pyrrolidone, polyethylene oxide, polyacrylate quats, polymaleic acid, polymaleic anhydride, polyurethanes, polyureas, gum karaya, gum acacia, locust bean gum, xanthan gum, guar gum, modified guar gum, maltodextrin, carboxymethyl cellulose, carboxypropyl cellulose, polyacrylamide, polyvinyl alcohol, poly AMPS, and polyacrylates. Other suitable polymers are disclosed, e.g., in U.S. Pat. Nos. 4,675,009; 5,536,263; 4,696,854; 5,741,510; and references cited therein. In one embodiment, the polymer is gum karaya. The term "gum karaya" refers to a vegetable gum produced as an exudate by trees of the genus *Sterculia*. Chemically, gum karaya is an acid polysaccharide composed of the sugars galactose, rhamnose, and galacturonic acid.

In a specific embodiment, the nature and amount of the polymer is selected, such that it will be generally recognized as safe (GRAS) for topical use.

Humectant

The formulation can optionally include one or more humectants to provide a moistening effect to the adhesive. For example, the humectant can hydrate the polymer. Any suitable humectant can be employed, provided the humectant effectively provides a moistening effect to the adhesive and the humectant remains stable in the formulation. In one embodiment, the stability is over a prolonged period of time, e.g., up to about 2 years, up to about 1 year, or up to about 6 months, typically experienced in the manufacturing, packaging, shipping, and/or storage of the patch. One suitable humectant is glycerin. Other suitable humectants include polyhydric alcohols such as ethylene glycol, propylene glycol, triethylene glycol, tetraethylene glycol, and sorbitol.

Any suitable amount of humectant can be employed, provided the amount of humectant effectively provides a moistening effect to the adhesive and the effective amount of humectant remains stable in the formulation. The suitable amount of humectant can depend upon the specific humectant or humectants employed and the specific polymer or polymers employed. For example, gum karaya can be employed as the polymer and glycerin can be employed as the humectant in about 20 wt. % to about 70 wt. % of the formulation, and in one embodiment about 30 wt. % to about 60 wt. % of the formulation, or about 40 wt. % to about 50 wt. % of the formulation.

In a specific embodiment, the nature and amount of the humectant is selected, such that it will be generally recognized as safe (GRAS) for topical use.

Topical Moisturizer

The formulation can optionally include a topical moisturizer (e.g., skin protectant). Any suitable topical skin protectant can be employed, provided the skin is effectively protected or moisturized and the skin protectant remains stable in the formulation. In one embodiment, the stability is over a prolonged period of time, e.g., up to about 2 years, up to about 1 year, or up to about 6 months, typically experienced in the manufacturing, packaging, shipping, and/or storage of the patch. Suitable skin protectants include, e.g. aloe, lanolin, glycerin, calamine, Vitamin E, Vitamin E acetate, Vitamin C, allantoin, aluminum hydroxide gel, bismuth subnitrate, boric acid, calamine, cocoa butter, dimethicone, glycerin, kaolin, live yeast cell derivative, petrolatum, pyridoxine hydrochloride, shark liver oil, sodium bicarbonate, sulfur, tannic acid, topical starch, trolamine, white petrolatum, zinc acetate, zinc carbonate zinc oxide, zinc sulfate, shea butter, and any combination thereof.

As used herein, calamine is a pink powder of zinc oxide and a skin protectant containing about 98% zinc oxide and about 0.5% ferric oxide; aloe is the dried latex of leaves of Curaco Aloe (Aloe barbadenis Miller, Aloe vera Linne) or Cape Aloe (Aloe ferox Miller and hybrids), of the family Liliacaea; Vitamin E is 3,4-dihydro-2,5,7,8-tetramethyl-2-(4,8,12-trimethyltridecyl)-2H-1-benzopy-ran-6-ol; Vitamin E acetate is 3,4-dihydro-2,5,7,8-tetramethyl-2-(4,8,12-trimethyltridecyl)-2H-1-benzopy-ran-6-ol acetate; and lanolin is the fat-like secretion of the sebaceous glands of sheep (i.e., complex mixture of esters and polyesters of 33 high molecular weight alcohols and 36 fatty acids) which is deposited onto the wool fibers. In one embodiment, the topical moisturizer can be aloe and Vitamin E.

Aloe is commercially available as Aloe Vera Gel from Terry Laboratories (Melbourne, Fla.). Aloe Vera Gel is commercially available as Aloe Vera Gel 40.times. (20.0 wt. % solution in water), Aloe Vera Gel 1.times. (0.5 wt. % solution in water), Aloe Vera Gel (5.0 wt. % solution in water), or solid Aloe Vera. The solid Aloe Vera can be dissolved in a carrier, such as water, to the desired concentration. In addition, the commercially available forms of Aloe Vera are optionally available as decolorized Aloe Vera.

Any suitable amount of topical moisturizer can be employed, provided the suitable amount of topical moisturizer or skin protectant effectively protects or moisturizes the skin and the effective amount of skin protectant remains stable in the formulation over a prolonged period of time. The suitable and effective amount of topical moisturizer can depend in part upon the specific moisturizer or moisturizers present in the formulation. For example, Aloe Vera Gel can be present up to about 40.0 wt. % of the formulation. In one embodiment, Aloe Vera Gel can be present up to about 5.0 wt. % of the formulation. In one embodiment, Aloe Vera Gel can be present up to about 1.0 wt. % of the formulation. In addition, Vitamin E acetate can be present up to about 5 wt. % of the formulation. In one embodiment, Vitamin E acetate can be present up to about 1.0 wt. % of the formulation. In one embodiment, Vitamin E acetate can be present up to about 0.5 wt. % of the formulation.

In a specific embodiment, the nature and amount of the topical moisturizer is selected, such that it will be generally recognized as safe (GRAS) for topical use.

Polyhydric Alcohol

The formulation can optionally include one or more polyhydric alcohols. Suitable polyhydric alcohols include, e.g., ethylene glycol, propylene glycol, triethylene glycol, tetraethylene glycol, sorbitol, or any combination thereof. Specifically, the polyhydric alcohol can include propylene glycol.

Any suitable amount of polyhydric alcohol can be employed. For example, when present in the formulation, the polyhydric alcohol can be present up to about 35 wt. % of the formulation, up to about 15 wt. % of the formulation, or up to about 5 wt. % of the formulation. In one embodiment, the polyhydric alcohol can be present in about 0.5 wt. % to about 5.0 wt. % of the formulation.

Water

The formulation can optionally include water, e.g., deionized water (DI). Any suitable amount of water can be employed, provided the amount of water maintains the adhesiveness of the adhesive and maintains the appropriate stability of the formulation. For example, deionized water can be present up to about 50 wt. % of the formulation, up to about 40.0 wt. % of the formulation, or up to about 30.0 wt. % of the formulation. In one embodiment, deionized water can be present up to about 20.0 wt. % of the formulation. In one embodiment, deionized water can be present up to about 10.0 wt. % of the formulation. In one embodiment, deionized water can be present in about 5.0 wt. % to about 15.0 wt. % of the formulation.

Skin Penetration Enhancer

The formulation can optionally include a skin penetration enhancer (or skin permeation enhancer). Any skin penetration enhancer can be employed, provided the skin penetration enhancer is safe (e.g., is on the GRAS list) and effectively facilitates the passage of *Cannabis* concentrate (or any desired substances contained therein) across the skin membrane. Suitable skin penetration enhancers include, e.g., dimethyl sulphoxide (DMSO), monoglycerides, $C_{10}$-$C_{20}$ fatty acid esters including ethyl palmitate and isopropyl myristate; acyl lactylates such as caproyl lactylic acid and lauroyl lactylic acid; dimethyl lauramide; dodecyl (lauryl) acetate; lactate esters such as lauryl lactate, and myristyl lactate; monoalkyl ethers of polyethyleneglycol and their alkyl or aryl carboxylic acid esters and carboxymethyl ethers such as polyethylene glycol-4 lauryl ether (Laureth-4) and polyethylene glycol-2 lauryl ether (Laureth-2); Myreth-3, myristyl sarcosine, and methyl laurate; polypropylene glycol, polyethylene glycol, lecithin, urea, amino acids, 1-dodecylhexahydro-2H-azepine 2-one (Azone), oleic acid, linoleic acid, isopropyl linoleate, oleyl alcohol, 1-dodecylazacycloheptan-2-one, and butanediol.

Any suitable amount of skin penetration enhancer can be employed, provided the amount of skin penetration enhancer facilitates the passage of *Cannabis* concentrate (or any desired substances contained therein) across the skin membrane. For example, the skin penetration enhancer can be present up to about 50 wt. % of the formulation, up to about 40.0 wt. % of the formulation, or up to about 30.0 wt. % of the formulation. In one embodiment, the skin penetration enhancer can be present up to about 20.0 wt. % of the formulation. In one embodiment, the skin penetration enhancer can be present up to about 10.0 wt. % of the formulation. In one embodiment, the skin penetration enhancer can be present in about 0.25 wt. % to about 15.0 wt. % of the formulation.

The Patch

The adhesive skin patch can have any suitable size and shape. In addition, the adhesive skin patch can be cut, as desired, to provide an adhesive skin patch of a suitable size and shape. The adhesive skin patch can be cut with any suitable cutting device such as a scissors, scalpel, or knife.

In one embodiment, the adhesive skin patch has a length of about 0.1 inch to about 12 inches (about 2.54 mm to about 304.8 mm), about 0.1 inch to about 8 inches (about 2.54 mm to about 203.2 mm), of about 0.20 inch to about 4 inches (about 5.08 mm to about 101.6 mm), or about 0.2 inches to about 2.0 inches (about 5.08 mm to about 50.8 mm). In one embodiment, the adhesive skin patch has a length of about 1.0 inch to about 8 inches (about 25.4 mm to about 203.2 mm), about 2 inches (about 50.8 mm to about 152.4 mm) to about 6 inches (about 5.08 mm to about 152.4 mm), or about 3 inches to about 4 inches (about 76.2 mm to about 101.6 mm).

In one embodiment, the adhesive skin patch has a width of about 0.1 inch to about 12.0 inches (about 2.54 mm to about 304.8 mm), about 0.1 inch to about 4 inches (about 2.54 mm to about 101.6 mm), about 0.20 inches to about 2.0 inches (about 5.08 mm to about 50.8 mm), or about 0.2 inches to about 1.0 inch (about 5.08 mm to about 25.4 mm). In one embodiment, the adhesive skin patch has a width of about 1.0 inch to about 8 inches (about 25.4 mm to about 203.2 mm), about 2 inches to about 6 inches (about 50.8 to about 152.4 mm), or about 3 inches to about 4 inches (about 76.2 mm to about 101.6 mm).

In one specific embodiment of the present invention, the adhesive skin patch can be oval or elliptical in shape. The oval or elliptical patch can have a length of about 0.25 inches to about 0.50 inches (6.35 mm to about 12.7 mm) and a width of about 0.25 inches to about 0.50 inches (6.35 mm to about 12.7 mm). In another specific embodiment of the present invention, the adhesive skin patch can have a circular shape. The circular patch can have a diameter of about 0.25 inches to about 0.50 inches (6.35 mm to about 12.7 mm).

In one embodiment, the adhesive skin patch can be individually wrapped. Some consumers have shown a preference for adhesive skin patches that are individually wrapped. The individually wrapped adhesive skin patch offers to the consumer the ability and convenience of being able to carry a few (e.g., 1, 2, or 3) adhesive skin patches that are each individually wrapped. In such an embodiment, the use of one patch will not compromise the cleanliness and/or sterility of the remaining patches. Alternatively, more than one adhesive skin patch can be wrapped together. For example, 2 to about 20, 2 to about 15, or 2 to about 10 adhesive skin patches can be wrapped together. The cost of such packaging and wrapping can be decreased, compared to skin patches that are individually wrapped. In one specific embodiment, the adhesive skin patch can be individually wrapped as a right and left handed pair. The cost of having two or more patches wrapped together is typically less expensive than skin patches that are individually wrapped.

In one embodiment of the present invention, the adhesive patch is sterile. The adhesive patch can be sterilized by any suitable means known to those of skill in the art. For example, the adhesive patch of the present invention can be sterilized by irradiation. Specifically, the adhesive patch of the present invention can be sterilized by terminal irradiation (e.g., when the adhesive patch of the present invention is in the package).

Production of the Patch

The adhesive patch of the present invention can be formulated or manufactured employing the above components. The adhesive patch of the present invention can be formulated or manufactured using any suitable technique. In one embodiment, the adhesive patch can be formulated or manufactured as described in U.S. Pat. Nos. 5,536,263; 5,741,510; and references cited therein.

The adhesive patch can be applied to any skin surface of a subject. The subject can be a human (e.g., child that is younger than 18 years of age). The adhesive patch can be applied by the subject, or by another person (e.g., parent, nurse, or physician).

Additional transdermal patches, and methods of preparing transdermal patches, are described, e.g., in US 2009/0028929; WO/2012/026829A1; US 2013/0220846; U.S. Pat. No. 8,095,213; U.S. Pat. No. 5,948,433; US 2014/0031770; WO/2013/027681A1; WO/2012/105624A1; WO/2008/008135A1; US 2008/0008747; WO/2008/133982A2; EP0674913A2; WO/2000/069405A1; U.S. Pat. No. 5,536,263; U.S. Pat. No. 5,741,510; U.S. Pat. No. 6,096,334; and US 2011/0293681.

Specific Ranges, Values, and Embodiments

Specific ranges, values, and embodiments provided below are for illustration purposes only and do not otherwise limit the scope of the invention, as defined by the claims. The specific ranges, values, and embodiments described below encompass all combinations and sub-combinations of each disclosed range, value, and embodiment, whether or not expressly described as such Solvent System When the SFE is carried out one time, the SFE can include: (i) a polar protic solvent system, (ii) a polar aprotic solvent system, (iii) a nonpolar protic solvent system, or (iv) a nonpolar aprotic solvent system.

In specific embodiments, the SFE is carried out one time, wherein the SFE includes a solvent systems illustrated in any one of 1-4 below.

| No. | SFE solvent system |
|---|---|
| 1 | polar protic |
| 2 | polar aprotic |
| 3 | nonpolar protic |
| 4 | nonpolar aprotic |

When the SFE is carried out two times, each FSFE can independently include: (i) a polar protic solvent system, (ii) a polar aprotic solvent system, (iii) a nonpolar protic solvent system, or (iv) a nonpolar aprotic solvent system.

In specific embodiments, the SFE is carried out two times, wherein the first and second FSFEs include solvent systems illustrated in any one of 1-16 below. When the first and second FSFEs include solvent systems having the same combination of polarity and proticity (e.g., both the first and second FSFEs include polar aprotic solvent systems), those FSFEs will typically be carried out at a different temperature and/or pressure.

| No. | First FSFE solvent system | Second FSFE solvent system |
|---|---|---|
| 1 | polar protic | polar protic |
| 2 | polar protic | polar aprotic |
| 3 | polar protic | nonpolar protic |
| 4 | polar protic | nonpolar aprotic |
| 5 | polar aprotic | polar protic |
| 6 | polar aprotic | polar aprotic |
| 7 | polar aprotic | nonpolar protic |
| 8 | polar aprotic | nonpolar aprotic |
| 9 | nonpolar protic | polar protic |
| 10 | nonpolar protic | polar aprotic |
| 11 | nonpolar protic | nonpolar protic |
| 12 | nonpolar protic | nonpolar aprotic |
| 13 | nonpolar aprotic | polar protic |
| 14 | nonpolar aprotic | polar aprotic |
| 15 | nonpolar aprotic | nonpolar protic |
| 16 | nonpolar aprotic | nonpolar aprotic |

When the SFE is carried out three times, each FSFE can independently include: (i) a polar protic solvent system, (ii) a polar aprotic solvent system, (iii) a nonpolar protic solvent system, or (iv) a nonpolar aprotic solvent system.

In specific embodiments, the SFE is carried out three times, wherein the first, second and third FSFEs include solvent systems illustrated in any one of 1-64 below. When at least two of the first, second and third FSFEs include solvent systems having the same combination of polarity and proticity (e.g., both the second and third FSFEs include polar aprotic solvent systems), those FSFEs will typically be carried out at a different temperature and/or pressure.

| No. | First FSFE solvent system | Second FSFE solvent system | Third FSFE solvent system |
|---|---|---|---|
| 1 | polar protic | polar protic | polar protic |
| 2 | polar protic | polar protic | polar aprotic |
| 3 | polar protic | polar protic | nonpolar protic |
| 4 | polar protic | polar protic | nonpolar aprotic |
| 5 | polar protic | polar aprotic | polar protic |
| 6 | polar protic | polar aprotic | polar aprotic |
| 7 | polar protic | polar aprotic | nonpolar protic |
| 8 | polar protic | polar aprotic | nonpolar aprotic |
| 9 | polar protic | nonpolar protic | polar protic |
| 10 | polar protic | nonpolar protic | polar aprotic |
| 11 | polar protic | nonpolar protic | nonpolar protic |
| 12 | polar protic | nonpolar protic | nonpolar aprotic |
| 13 | polar protic | nonpolar aprotic | polar protic |
| 14 | polar protic | nonpolar aprotic | polar aprotic |
| 15 | polar protic | nonpolar aprotic | nonpolar protic |
| 16 | polar protic | nonpolar aprotic | nonpolar aprotic |
| 17 | polar aprotic | polar protic | polar protic |
| 18 | polar aprotic | polar protic | polar aprotic |
| 19 | polar aprotic | polar protic | nonpolar protic |
| 20 | polar aprotic | polar protic | nonpolar aprotic |
| 21 | polar aprotic | polar aprotic | polar protic |
| 22 | polar aprotic | polar aprotic | polar aprotic |
| 23 | polar aprotic | polar aprotic | nonpolar protic |
| 24 | polar aprotic | polar aprotic | nonpolar aprotic |
| 25 | polar aprotic | nonpolar protic | polar protic |
| 26 | polar aprotic | nonpolar protic | polar aprotic |
| 27 | polar aprotic | nonpolar protic | nonpolar protic |
| 28 | polar aprotic | nonpolar protic | nonpolar aprotic |
| 29 | polar aprotic | nonpolar aprotic | polar protic |
| 30 | polar aprotic | nonpolar aprotic | polar aprotic |
| 31 | polar aprotic | nonpolar aprotic | nonpolar protic |
| 32 | polar aprotic | nonpolar aprotic | nonpolar aprotic |
| 33 | nonpolar protic | polar protic | polar protic |
| 34 | nonpolar protic | polar protic | polar aprotic |
| 35 | nonpolar protic | polar protic | nonpolar protic |
| 36 | nonpolar protic | polar protic | nonpolar aprotic |
| 37 | nonpolar protic | polar aprotic | polar protic |
| 38 | nonpolar protic | polar aprotic | polar aprotic |
| 39 | nonpolar protic | polar aprotic | nonpolar protic |
| 40 | nonpolar protic | polar aprotic | nonpolar aprotic |
| 41 | nonpolar protic | nonpolar protic | polar protic |
| 42 | nonpolar protic | nonpolar protic | polar aprotic |
| 43 | nonpolar protic | nonpolar protic | nonpolar protic |
| 44 | nonpolar protic | nonpolar protic | nonpolar aprotic |
| 45 | nonpolar protic | nonpolar aprotic | polar protic |
| 46 | nonpolar protic | nonpolar aprotic | polar aprotic |
| 47 | nonpolar protic | nonpolar aprotic | nonpolar protic |
| 48 | nonpolar protic | nonpolar aprotic | nonpolar aprotic |
| 49 | nonpolar aprotic | polar protic | polar protic |
| 50 | nonpolar aprotic | polar protic | polar aprotic |
| 51 | nonpolar aprotic | polar protic | nonpolar protic |
| 52 | nonpolar aprotic | polar protic | nonpolar aprotic |
| 53 | nonpolar aprotic | polar aprotic | polar protic |
| 54 | nonpolar aprotic | polar aprotic | polar aprotic |
| 55 | nonpolar aprotic | polar aprotic | nonpolar protic |
| 56 | nonpolar aprotic | polar aprotic | nonpolar aprotic |
| 57 | nonpolar aprotic | nonpolar protic | polar protic |
| 58 | nonpolar aprotic | nonpolar protic | polar aprotic |
| 59 | nonpolar aprotic | nonpolar protic | nonpolar protic |
| 60 | nonpolar aprotic | nonpolar protic | nonpolar aprotic |
| 61 | nonpolar aprotic | nonpolar aprotic | polar protic |
| 62 | nonpolar aprotic | nonpolar aprotic | polar aprotic |
| 63 | nonpolar aprotic | nonpolar aprotic | nonpolar protic |
| 64 | nonpolar aprotic | nonpolar aprotic | nonpolar aprotic |

When the SFE is carried out four times, each FSFE can independently include: (i) a polar protic solvent system, (ii) a polar aprotic solvent system, (iii) a nonpolar protic solvent system, or (iv) a nonpolar aprotic solvent system.

In specific embodiments, the SFE is carried out four times, wherein the first, second, third and fourth FSFEs include solvent systems illustrated in any one of 1-256 below. When at least two of the first, second, third and fourth FSFEs include solvent systems having the same combination of polarity and proticity (e.g., both the third and fourth FSFEs include polar aprotic solvent systems), those FSFEs will typically be carried out at a different temperature and/or pressure.

| No. | First FSFE solvent system | Second FSFE solvent system | Third FSFE solvent system | Fourth FSFE solvent system |
|---|---|---|---|---|
| 1 | polar protic | polar protic | polar protic | polar protic |
| 2 | polar protic | polar protic | polar protic | polar aprotic |
| 3 | polar protic | polar protic | polar protic | nonpolar protic |
| 4 | polar protic | polar protic | polar protic | nonpolar aprotic |
| 5 | polar protic | polar protic | polar aprotic | polar protic |
| 6 | polar protic | polar protic | polar aprotic | polar aprotic |
| 7 | polar protic | polar protic | polar aprotic | nonpolar protic |
| 8 | polar protic | polar protic | polar aprotic | nonpolar aprotic |
| 9 | polar protic | polar protic | nonpolar protic | polar protic |
| 10 | polar protic | polar protic | nonpolar protic | polar aprotic |
| 11 | polar protic | polar protic | nonpolar protic | nonpolar protic |
| 12 | polar protic | polar protic | nonpolar protic | nonpolar aprotic |
| 13 | polar protic | polar protic | nonpolar aprotic | polar protic |
| 14 | polar protic | polar protic | nonpolar aprotic | polar aprotic |
| 15 | polar protic | polar protic | nonpolar aprotic | nonpolar protic |
| 16 | polar protic | polar protic | nonpolar aprotic | nonpolar aprotic |
| 17 | polar protic | polar aprotic | polar protic | polar protic |
| 18 | polar protic | polar aprotic | polar protic | polar aprotic |
| 19 | polar protic | polar aprotic | polar protic | nonpolar protic |
| 20 | polar protic | polar aprotic | polar protic | nonpolar aprotic |
| 21 | polar protic | polar aprotic | polar aprotic | polar protic |
| 22 | polar protic | polar aprotic | polar aprotic | polar aprotic |
| 23 | polar protic | polar aprotic | polar aprotic | nonpolar protic |
| 24 | polar protic | polar aprotic | polar aprotic | nonpolar aprotic |
| 25 | polar protic | polar aprotic | nonpolar protic | polar protic |
| 26 | polar protic | polar aprotic | nonpolar protic | polar aprotic |
| 27 | polar protic | polar aprotic | nonpolar protic | nonpolar protic |
| 28 | polar protic | polar aprotic | nonpolar protic | nonpolar aprotic |
| 29 | polar protic | polar aprotic | nonpolar aprotic | polar protic |
| 30 | polar protic | polar aprotic | nonpolar aprotic | polar aprotic |

| No. | First FSFE solvent system | Second FSFE solvent system | Third FSFE solvent system | Fourth FSFE solvent system |
| --- | --- | --- | --- | --- |
| 31 | polar protic | polar aprotic | nonpolar aprotic | nonpolar protic |
| 32 | polar protic | polar aprotic | nonpolar aprotic | nonpolar aprotic |
| 33 | polar protic | nonpolar protic | polar protic | polar protic |
| 34 | polar protic | nonpolar protic | polar protic | polar aprotic |
| 35 | polar protic | nonpolar protic | polar protic | nonpolar protic |
| 36 | polar protic | nonpolar protic | polar protic | nonpolar aprotic |
| 37 | polar protic | nonpolar protic | polar aprotic | polar protic |
| 38 | polar protic | nonpolar protic | polar aprotic | polar aprotic |
| 39 | polar protic | nonpolar protic | polar aprotic | nonpolar protic |
| 40 | polar protic | nonpolar protic | polar aprotic | nonpolar aprotic |
| 41 | polar protic | nonpolar protic | nonpolar protic | polar protic |
| 42 | polar protic | nonpolar protic | nonpolar protic | polar aprotic |
| 43 | polar protic | nonpolar protic | nonpolar protic | nonpolar protic |
| 44 | polar protic | nonpolar protic | nonpolar protic | nonpolar aprotic |
| 45 | polar protic | nonpolar protic | nonpolar aprotic | polar protic |
| 46 | polar protic | nonpolar protic | nonpolar aprotic | polar aprotic |
| 47 | polar protic | nonpolar protic | nonpolar aprotic | nonpolar protic |
| 48 | polar protic | nonpolar protic | nonpolar aprotic | nonpolar aprotic |
| 49 | polar protic | nonpolar aprotic | polar protic | polar protic |
| 50 | polar protic | nonpolar aprotic | polar protic | polar aprotic |
| 51 | polar protic | nonpolar aprotic | polar protic | nonpolar protic |
| 52 | polar protic | nonpolar aprotic | polar protic | nonpolar aprotic |
| 53 | polar protic | nonpolar aprotic | polar aprotic | polar protic |
| 54 | polar protic | nonpolar aprotic | polar aprotic | polar aprotic |
| 55 | polar protic | nonpolar aprotic | polar aprotic | nonpolar protic |
| 56 | polar protic | nonpolar aprotic | polar aprotic | nonpolar aprotic |
| 57 | polar protic | nonpolar aprotic | nonpolar protic | polar protic |
| 58 | polar protic | nonpolar aprotic | nonpolar protic | polar aprotic |
| 59 | polar protic | nonpolar aprotic | nonpolar protic | nonpolar protic |
| 60 | polar protic | nonpolar aprotic | nonpolar protic | nonpolar aprotic |
| 61 | polar protic | nonpolar aprotic | nonpolar aprotic | polar protic |
| 62 | polar protic | nonpolar aprotic | nonpolar aprotic | polar aprotic |
| 63 | polar protic | nonpolar aprotic | nonpolar aprotic | nonpolar protic |
| 64 | polar protic | nonpolar aprotic | nonpolar aprotic | nonpolar aprotic |
| 65 | polar aprotic | polar protic | polar protic | polar protic |
| 66 | polar aprotic | polar protic | polar protic | polar aprotic |
| 67 | polar aprotic | polar protic | polar protic | nonpolar protic |
| 68 | polar aprotic | polar protic | polar protic | nonpolar aprotic |
| 69 | polar aprotic | polar protic | polar aprotic | polar protic |
| 70 | polar aprotic | polar protic | polar aprotic | polar aprotic |
| 71 | polar aprotic | polar protic | polar aprotic | nonpolar protic |
| 72 | polar aprotic | polar protic | polar aprotic | nonpolar aprotic |
| 73 | polar aprotic | polar protic | nonpolar protic | polar protic |
| 74 | polar aprotic | polar protic | nonpolar protic | polar aprotic |
| 75 | polar aprotic | polar protic | nonpolar protic | nonpolar protic |
| 76 | polar aprotic | polar protic | nonpolar protic | nonpolar aprotic |
| 77 | polar aprotic | polar protic | nonpolar aprotic | polar protic |
| 78 | polar aprotic | polar protic | nonpolar aprotic | polar aprotic |
| 79 | polar aprotic | polar protic | nonpolar aprotic | nonpolar protic |
| 80 | polar aprotic | polar protic | nonpolar aprotic | nonpolar aprotic |
| 81 | polar aprotic | polar aprotic | polar protic | polar protic |
| 82 | polar aprotic | polar aprotic | polar protic | polar aprotic |
| 83 | polar aprotic | polar aprotic | polar protic | nonpolar protic |
| 84 | polar aprotic | polar aprotic | polar protic | nonpolar aprotic |
| 85 | polar aprotic | polar aprotic | polar aprotic | polar protic |
| 86 | polar aprotic | polar aprotic | polar aprotic | polar aprotic |
| 87 | polar aprotic | polar aprotic | polar aprotic | nonpolar protic |
| 88 | polar aprotic | polar aprotic | polar aprotic | nonpolar aprotic |
| 89 | polar aprotic | polar aprotic | nonpolar protic | polar protic |
| 90 | polar aprotic | polar aprotic | nonpolar protic | polar aprotic |
| 91 | polar aprotic | polar aprotic | nonpolar protic | nonpolar protic |
| 92 | polar aprotic | polar aprotic | nonpolar protic | nonpolar aprotic |
| 93 | polar aprotic | polar aprotic | nonpolar aprotic | polar protic |
| 94 | polar aprotic | polar aprotic | nonpolar aprotic | polar aprotic |
| 95 | polar aprotic | polar aprotic | nonpolar aprotic | nonpolar protic |
| 96 | polar aprotic | polar aprotic | nonpolar aprotic | nonpolar aprotic |
| 97 | polar aprotic | nonpolar protic | polar protic | polar protic |
| 98 | polar aprotic | nonpolar protic | polar protic | polar aprotic |
| 99 | polar aprotic | nonpolar protic | polar protic | nonpolar protic |
| 100 | polar aprotic | nonpolar protic | polar protic | nonpolar aprotic |
| 101 | polar aprotic | nonpolar protic | polar aprotic | polar protic |
| 102 | polar aprotic | nonpolar protic | polar aprotic | polar aprotic |
| 103 | polar aprotic | nonpolar protic | polar aprotic | nonpolar protic |
| 104 | polar aprotic | nonpolar protic | polar aprotic | nonpolar aprotic |
| 105 | polar aprotic | nonpolar protic | nonpolar protic | polar protic |
| 106 | polar aprotic | nonpolar protic | nonpolar protic | polar aprotic |
| 107 | polar aprotic | nonpolar protic | nonpolar protic | nonpolar protic |
| 108 | polar aprotic | nonpolar protic | nonpolar protic | nonpolar aprotic |
| 109 | polar aprotic | nonpolar protic | nonpolar aprotic | polar protic |
| 110 | polar aprotic | nonpolar protic | nonpolar aprotic | polar aprotic |
| 111 | polar aprotic | nonpolar protic | nonpolar aprotic | nonpolar protic |
| 112 | polar aprotic | nonpolar protic | nonpolar aprotic | nonpolar aprotic |
| 113 | polar aprotic | nonpolar aprotic | polar protic | polar protic |
| 114 | polar aprotic | nonpolar aprotic | polar protic | polar aprotic |
| 115 | polar aprotic | nonpolar aprotic | polar protic | nonpolar protic |
| 116 | polar aprotic | nonpolar aprotic | polar protic | nonpolar aprotic |
| 117 | polar aprotic | nonpolar aprotic | polar aprotic | polar protic |
| 118 | polar aprotic | nonpolar aprotic | polar aprotic | polar aprotic |
| 119 | polar aprotic | nonpolar aprotic | polar aprotic | nonpolar protic |
| 120 | polar aprotic | nonpolar aprotic | polar aprotic | nonpolar aprotic |
| 121 | polar aprotic | nonpolar aprotic | nonpolar protic | polar protic |
| 122 | polar aprotic | nonpolar aprotic | nonpolar protic | polar aprotic |
| 123 | polar aprotic | nonpolar aprotic | nonpolar protic | nonpolar protic |
| 124 | polar aprotic | nonpolar aprotic | nonpolar protic | nonpolar aprotic |
| 125 | polar aprotic | nonpolar aprotic | nonpolar aprotic | polar protic |
| 126 | polar aprotic | nonpolar aprotic | nonpolar aprotic | polar aprotic |
| 127 | polar aprotic | nonpolar aprotic | nonpolar aprotic | nonpolar protic |
| 128 | polar aprotic | nonpolar aprotic | nonpolar aprotic | nonpolar aprotic |
| 129 | nonpolar protic | polar protic | polar protic | polar protic |
| 130 | nonpolar protic | polar protic | polar protic | polar aprotic |
| 131 | nonpolar protic | polar protic | polar protic | nonpolar protic |
| 132 | nonpolar protic | polar protic | polar protic | nonpolar aprotic |
| 133 | nonpolar protic | polar protic | polar aprotic | polar protic |
| 134 | nonpolar protic | polar protic | polar aprotic | polar aprotic |
| 135 | nonpolar protic | polar protic | polar aprotic | nonpolar protic |
| 136 | nonpolar protic | polar protic | polar aprotic | nonpolar aprotic |
| 137 | nonpolar protic | polar protic | nonpolar protic | polar protic |
| 138 | nonpolar protic | polar protic | nonpolar protic | polar aprotic |
| 139 | nonpolar protic | polar protic | nonpolar protic | nonpolar protic |
| 140 | nonpolar protic | polar protic | nonpolar protic | nonpolar aprotic |
| 141 | nonpolar protic | polar protic | nonpolar aprotic | polar protic |
| 142 | nonpolar protic | polar protic | nonpolar aprotic | polar aprotic |
| 143 | nonpolar protic | polar protic | nonpolar aprotic | nonpolar protic |
| 144 | nonpolar protic | polar protic | nonpolar aprotic | nonpolar aprotic |
| 145 | nonpolar protic | polar aprotic | polar protic | polar protic |
| 146 | nonpolar protic | polar aprotic | polar protic | polar aprotic |
| 147 | nonpolar protic | polar aprotic | polar protic | nonpolar protic |
| 148 | nonpolar protic | polar aprotic | polar protic | nonpolar aprotic |
| 149 | nonpolar protic | polar aprotic | polar aprotic | polar protic |
| 150 | nonpolar protic | polar aprotic | polar aprotic | polar aprotic |
| 151 | nonpolar protic | polar aprotic | polar aprotic | nonpolar protic |
| 152 | nonpolar protic | polar aprotic | polar aprotic | nonpolar aprotic |
| 153 | nonpolar protic | polar aprotic | nonpolar protic | polar protic |
| 154 | nonpolar protic | polar aprotic | nonpolar protic | polar aprotic |
| 155 | nonpolar protic | polar aprotic | nonpolar protic | nonpolar protic |
| 156 | nonpolar protic | polar aprotic | nonpolar protic | nonpolar aprotic |
| 157 | nonpolar protic | polar aprotic | nonpolar aprotic | polar protic |
| 158 | nonpolar protic | polar aprotic | nonpolar aprotic | polar aprotic |
| 159 | nonpolar protic | polar aprotic | nonpolar aprotic | nonpolar protic |
| 160 | nonpolar protic | polar aprotic | nonpolar aprotic | nonpolar aprotic |
| 161 | nonpolar protic | nonpolar protic | polar protic | polar protic |
| 162 | nonpolar protic | nonpolar protic | polar protic | polar aprotic |
| 163 | nonpolar protic | nonpolar protic | polar protic | nonpolar protic |
| 164 | nonpolar protic | nonpolar protic | polar protic | nonpolar aprotic |
| 165 | nonpolar protic | nonpolar protic | polar aprotic | polar protic |
| 166 | nonpolar protic | nonpolar protic | polar aprotic | polar aprotic |
| 167 | nonpolar protic | nonpolar protic | polar aprotic | nonpolar protic |
| 168 | nonpolar protic | nonpolar protic | polar aprotic | nonpolar aprotic |
| 169 | nonpolar protic | nonpolar protic | nonpolar protic | polar protic |
| 170 | nonpolar protic | nonpolar protic | nonpolar protic | polar aprotic |
| 171 | nonpolar protic | nonpolar protic | nonpolar protic | nonpolar protic |
| 172 | nonpolar protic | nonpolar protic | nonpolar protic | nonpolar aprotic |
| 173 | nonpolar protic | nonpolar protic | nonpolar aprotic | polar protic |
| 174 | nonpolar protic | nonpolar protic | nonpolar aprotic | polar aprotic |
| 175 | nonpolar protic | nonpolar protic | nonpolar aprotic | nonpolar protic |
| 176 | nonpolar protic | nonpolar protic | nonpolar aprotic | nonpolar aprotic |
| 177 | nonpolar protic | nonpolar aprotic | polar protic | polar protic |
| 178 | nonpolar protic | nonpolar aprotic | polar protic | polar aprotic |
| 179 | nonpolar protic | nonpolar aprotic | polar protic | nonpolar protic |
| 180 | nonpolar protic | nonpolar aprotic | polar protic | nonpolar aprotic |
| 181 | nonpolar protic | nonpolar aprotic | polar aprotic | polar protic |
| 182 | nonpolar protic | nonpolar aprotic | polar aprotic | polar aprotic |

-continued

| No. | First FSFE solvent system | Second FSFE solvent system | Third FSFE solvent system | Fourth FSFE solvent system |
|---|---|---|---|---|
| 183 | nonpolar protic | nonpolar aprotic | polar aprotic | nonpolar protic |
| 184 | nonpolar protic | nonpolar aprotic | polar aprotic | nonpolar aprotic |
| 185 | nonpolar protic | nonpolar aprotic | nonpolar protic | polar protic |
| 186 | nonpolar protic | nonpolar aprotic | nonpolar protic | polar aprotic |
| 187 | nonpolar protic | nonpolar aprotic | nonpolar protic | nonpolar protic |
| 188 | nonpolar protic | nonpolar aprotic | nonpolar protic | nonpolar aprotic |
| 189 | nonpolar protic | nonpolar aprotic | nonpolar aprotic | polar protic |
| 190 | nonpolar protic | nonpolar aprotic | nonpolar aprotic | polar aprotic |
| 191 | nonpolar protic | nonpolar aprotic | nonpolar aprotic | nonpolar protic |
| 192 | nonpolar protic | nonpolar aprotic | nonpolar aprotic | nonpolar aprotic |
| 193 | nonpolar aprotic | polar protic | polar protic | polar protic |
| 194 | nonpolar aprotic | polar protic | polar protic | polar aprotic |
| 195 | nonpolar aprotic | polar protic | polar protic | nonpolar protic |
| 196 | nonpolar aprotic | polar protic | polar protic | nonpolar aprotic |
| 197 | nonpolar aprotic | polar protic | polar aprotic | polar protic |
| 198 | nonpolar aprotic | polar protic | polar aprotic | polar aprotic |
| 199 | nonpolar aprotic | polar protic | polar aprotic | nonpolar protic |
| 200 | nonpolar aprotic | polar protic | polar aprotic | nonpolar aprotic |
| 201 | nonpolar aprotic | polar protic | nonpolar protic | polar protic |
| 202 | nonpolar aprotic | polar protic | nonpolar protic | polar aprotic |
| 203 | nonpolar aprotic | polar protic | nonpolar protic | nonpolar protic |
| 204 | nonpolar aprotic | polar protic | nonpolar protic | nonpolar aprotic |
| 205 | nonpolar aprotic | polar protic | nonpolar aprotic | polar protic |
| 206 | nonpolar aprotic | polar protic | nonpolar aprotic | polar aprotic |
| 207 | nonpolar aprotic | polar protic | nonpolar aprotic | nonpolar protic |
| 208 | nonpolar aprotic | polar protic | nonpolar aprotic | nonpolar aprotic |
| 209 | nonpolar aprotic | polar aprotic | polar protic | polar protic |
| 210 | nonpolar aprotic | polar aprotic | polar protic | polar aprotic |
| 211 | nonpolar aprotic | polar aprotic | polar protic | nonpolar protic |
| 212 | nonpolar aprotic | polar aprotic | polar protic | nonpolar aprotic |
| 213 | nonpolar aprotic | polar aprotic | polar aprotic | polar protic |
| 214 | nonpolar aprotic | polar aprotic | polar aprotic | polar protic |
| 215 | nonpolar aprotic | polar aprotic | polar aprotic | nonpolar aprotic |
| 216 | nonpolar aprotic | polar protic | polar protic | nonpolar aprotic |
| 217 | nonpolar aprotic | polar protic | nonpolar protic | polar protic |
| 218 | nonpolar aprotic | polar protic | nonpolar protic | polar aprotic |
| 219 | nonpolar aprotic | polar protic | nonpolar protic | nonpolar protic |
| 220 | nonpolar aprotic | polar protic | nonpolar protic | nonpolar aprotic |
| 221 | nonpolar aprotic | polar protic | nonpolar aprotic | polar protic |
| 222 | nonpolar aprotic | polar protic | nonpolar aprotic | polar aprotic |
| 223 | nonpolar aprotic | polar protic | nonpolar aprotic | nonpolar protic |
| 224 | nonpolar aprotic | polar protic | nonpolar aprotic | nonpolar aprotic |
| 225 | nonpolar aprotic | nonpolar protic | polar protic | polar protic |
| 226 | nonpolar aprotic | nonpolar protic | polar protic | polar aprotic |
| 227 | nonpolar aprotic | nonpolar protic | polar protic | nonpolar protic |
| 228 | nonpolar aprotic | nonpolar protic | polar protic | nonpolar aprotic |
| 229 | nonpolar aprotic | nonpolar protic | polar protic | polar protic |
| 230 | nonpolar aprotic | nonpolar protic | polar protic | polar aprotic |
| 231 | nonpolar aprotic | nonpolar protic | polar protic | nonpolar protic |
| 232 | nonpolar aprotic | nonpolar protic | polar protic | nonpolar aprotic |
| 233 | nonpolar aprotic | nonpolar protic | nonpolar protic | polar protic |
| 234 | nonpolar aprotic | nonpolar protic | nonpolar protic | polar aprotic |
| 235 | nonpolar aprotic | nonpolar protic | nonpolar protic | nonpolar protic |
| 236 | nonpolar aprotic | nonpolar protic | nonpolar protic | nonpolar aprotic |
| 237 | nonpolar aprotic | nonpolar protic | nonpolar aprotic | polar protic |
| 238 | nonpolar aprotic | nonpolar protic | nonpolar aprotic | polar aprotic |
| 239 | nonpolar aprotic | nonpolar protic | nonpolar aprotic | nonpolar protic |
| 240 | nonpolar aprotic | nonpolar protic | nonpolar aprotic | nonpolar aprotic |
| 241 | nonpolar aprotic | nonpolar aprotic | polar protic | polar protic |
| 242 | nonpolar aprotic | nonpolar aprotic | polar protic | polar aprotic |
| 243 | nonpolar aprotic | nonpolar aprotic | polar protic | nonpolar protic |
| 244 | nonpolar aprotic | nonpolar aprotic | polar protic | nonpolar aprotic |
| 245 | nonpolar aprotic | nonpolar aprotic | polar aprotic | polar protic |
| 246 | nonpolar aprotic | nonpolar aprotic | polar aprotic | polar aprotic |
| 247 | nonpolar aprotic | nonpolar aprotic | polar aprotic | nonpolar protic |
| 248 | nonpolar aprotic | nonpolar aprotic | polar aprotic | nonpolar aprotic |
| 249 | nonpolar aprotic | nonpolar aprotic | nonpolar protic | polar protic |
| 250 | nonpolar aprotic | nonpolar aprotic | nonpolar protic | polar aprotic |
| 251 | nonpolar aprotic | nonpolar aprotic | nonpolar protic | nonpolar protic |
| 252 | nonpolar aprotic | nonpolar aprotic | nonpolar protic | nonpolar aprotic |
| 253 | nonpolar aprotic | nonpolar aprotic | nonpolar aprotic | polar protic |
| 254 | nonpolar aprotic | nonpolar aprotic | nonpolar aprotic | polar aprotic |
| 255 | nonpolar aprotic | nonpolar aprotic | nonpolar aprotic | nonpolar protic |
| 256 | nonpolar aprotic | nonpolar aprotic | nonpolar aprotic | nonpolar aprotic |

Pressure

When the SFE is carried out two times, each FSFE can independently be carried out at a pressure of about: (i) 750-4,000 psi, (ii) 4,000-7,000 psi, or (iii) 7,000-25,000 psi.

In specific embodiments, the SFE is carried out two times, wherein the first and second FSFEs are carried out at pressures illustrated in any one of 1-9 below. When the first and second FSFEs are carried out at the same pressure range, those FSFEs will typically be carried out at a different temperature and/or solvent system having a different combination of polarity and proticity (e.g., carried out at the same pressure range, the first FSFE includes a polar aprotic solvent system and the second FSFE includes a nonpolar protic solvent system).

| No. | First FSFE pressure | Second FSFE pressure |
|---|---|---|
| 1 | 750-4,000 psi | 750-4,000 psi |
| 2 | 750-4,000 psi | 4,000-7,000 psi |
| 3 | 750-4,000 psi | 7,000-25,000 psi |
| 4 | 4,000-7,000 psi | 750-4,000 psi |
| 5 | 4,000-7,000 psi | 4,000-7,000 psi |
| 6 | 4,000-7,000 psi | 7,000-25,000 psi |
| 7 | 7,000-25,000 psi | 750-4,000 psi |
| 8 | 7,000-25,000 psi | 4,000-7,000 psi |
| 9 | 7,000-25,000 psi | 7,000-25,000 psi |

When the SFE is carried out three times, each FSFE can independently be carried out at a pressure of about: (i) 750-4,000 psi, (ii) 4,000-7,000 psi, or (iii) 7,000-25,000 psi.

In specific embodiments, the SFE is carried out three times, wherein the first, second and third FSFEs are carried out at pressures illustrated in any one of 1-27 below. When any one or more of the first, second and third FSFEs are carried out at the same pressure range, those FSFEs will typically be carried out at a different temperature and/or solvent system having a different combination of polarity and proticity (e.g., carried out at the same pressure range, the second FSFE includes a polar aprotic solvent system and the third FSFE includes a nonpolar protic solvent system).

| No. | First FSFE pressure | Second FSFE pressure | Third FSFE pressure |
|---|---|---|---|
| 1 | 750-4,000 psi | 750-4,000 psi | 750-4,000 psi |
| 2 | 750-4,000 psi | 750-4,000 psi | 4,000-7,000 psi |
| 3 | 750-4,000 psi | 750-4,000 psi | 7,000-25,000 psi |
| 4 | 750-4,000 psi | 4,000-7,000 psi | 750-4,000 psi |
| 5 | 750-4,000 psi | 4,000-7,000 psi | 4,000-7,000 psi |
| 6 | 750-4,000 psi | 4,000-7,000 psi | 7,000-25,000 psi |
| 7 | 750-4,000 psi | 7,000-25,000 psi | 750-4,000 psi |
| 8 | 750-4,000 psi | 7,000-25,000 psi | 4,000-7,000 psi |
| 9 | 750-4,000 psi | 7,000-25,000 psi | 7,000-25,000 psi |
| 10 | 4,000-7,000 psi | 750-4,000 psi | 750-4,000 psi |
| 11 | 4,000-7,000 psi | 750-4,000 psi | 4,000-7,000 psi |
| 12 | 4,000-7,000 psi | 750-4,000 psi | 7,000-25,000 psi |
| 13 | 4,000-7,000 psi | 4,000-7,000 psi | 750-4,000 psi |
| 14 | 4,000-7,000 psi | 4,000-7,000 psi | 4,000-7,000 psi |
| 15 | 4,000-7,000 psi | 4,000-7,000 psi | 7,000-25,000 psi |
| 16 | 4,000-7,000 psi | 7,000-25,000 psi | 750-4,000 psi |
| 17 | 4,000-7,000 psi | 7,000-25,000 psi | 4,000-7,000 psi |
| 18 | 4,000-7,000 psi | 7,000-25,000 psi | 7,000-25,000 psi |
| 19 | 7,000-25,000 psi | 750-4,000 psi | 750-4,000 psi |
| 20 | 7,000-25,000 psi | 750-4,000 psi | 4,000-7,000 psi |
| 21 | 7,000-25,000 psi | 750-4,000 psi | 7,000-25,000 psi |
| 22 | 7,000-25,000 psi | 4,000-7,000 psi | 750-4,000 psi |
| 23 | 7,000-25,000 psi | 4,000-7,000 psi | 4,000-7,000 psi |
| 24 | 7,000-25,000 psi | 4,000-7,000 psi | 7,000-25,000 psi |
| 25 | 7,000-25,000 psi | 7,000-25,000 psi | 750-4,000 psi |
| 26 | 7,000-25,000 psi | 7,000-25,000 psi | 4,000-7,000 psi |
| 27 | 7,000-25,000 psi | 7,000-25,000 psi | 7,000-25,000 psi |

When the SFE is carried out four times, each FSFE can independently be carried out at a pressure of about: (i) 750-4,000 psi, (ii) 4,000-7,000 psi, or (iii) 7,000-25,000 psi.

In specific embodiments, the SFE is carried out four times, wherein the first, second, third and fourth FSFEs are carried out at pressures illustrated in any one of 1-81 below. When any one or more of the first, second, third and fourth FSFEs are carried out at the same pressure range, those FSFEs will typically be carried out at a different temperature and/or solvent system having a different combination of polarity and proticity (e.g., carried out at the same pressure range, the third FSFE includes a polar aprotic solvent system and the fourth FSFE includes a nonpolar protic solvent system).

| No. | First FSFE pressure | Second FSFE pressure | Third FSFE pressure | Fourth FSFE pressure |
|---|---|---|---|---|
| 1 | 750-4,000 psi | 750-4,000 psi | 750-4,000 psi | 750-4,000 psi |
| 2 | 750-4,000 psi | 750-4,000 psi | 750-4,000 psi | 4,000-7,000 psi |
| 3 | 750-4,000 psi | 750-4,000 psi | 750-4,000 psi | 7,000-25,000 psi |
| 4 | 750-4,000 psi | 750-4,000 psi | 4,000-7,000 psi | 750-4,000 psi |
| 5 | 750-4,000 psi | 750-4,000 psi | 4,000-7,000 psi | 4,000-7,000 psi |
| 6 | 750-4,000 psi | 750-4,000 psi | 4,000-7,000 psi | 7,000-25,000 psi |
| 7 | 750-4,000 psi | 750-4,000 psi | 7,000-25,000 psi | 750-4,000 psi |
| 8 | 750-4,000 psi | 750-4,000 psi | 7,000-25,000 psi | 4,000-7,000 psi |
| 9 | 750-4,000 psi | 750-4,000 psi | 7,000-25,000 psi | 7,000-25,000 psi |
| 10 | 750-4,000 psi | 4,000-7,000 psi | 750-4,000 psi | 750-4,000 psi |
| 11 | 750-4,000 psi | 4,000-7,000 psi | 750-4,000 psi | 4,000-7,000 psi |
| 12 | 750-4,000 psi | 4,000-7,000 psi | 750-4,000 psi | 7,000-25,000 psi |
| 13 | 750-4,000 psi | 4,000-7,000 psi | 4,000-7,000 psi | 750-4,000 psi |
| 14 | 750-4,000 psi | 4,000-7,000 psi | 4,000-7,000 psi | 4,000-7,000 psi |
| 15 | 750-4,000 psi | 4,000-7,000 psi | 4,000-7,000 psi | 7,000-25,000 psi |
| 16 | 750-4,000 psi | 4,000-7,000 psi | 7,000-25,000 psi | 750-4,000 psi |
| 17 | 750-4,000 psi | 4,000-7,000 psi | 7,000-25,000 psi | 4,000-7,000 psi |
| 18 | 750-4,000 psi | 4,000-7,000 psi | 7,000-25,000 psi | 7,000-25,000 psi |
| 19 | 750-4,000 psi | 7,000-25,000 psi | 750-4,000 psi | 750-4,000 psi |
| 20 | 750-4,000 psi | 7,000-25,000 psi | 750-4,000 psi | 4,000-7,000 psi |
| 21 | 750-4,000 psi | 7,000-25,000 psi | 750-4,000 psi | 7,000-25,000 psi |
| 22 | 750-4,000 psi | 7,000-25,000 psi | 4,000-7,000 psi | 750-4,000 psi |
| 23 | 750-4,000 psi | 7,000-25,000 psi | 4,000-7,000 psi | 4,000-7,000 psi |
| 24 | 750-4,000 psi | 7,000-25,000 psi | 4,000-7,000 psi | 7,000-25,000 psi |
| 25 | 750-4,000 psi | 7,000-25,000 psi | 7,000-25,000 psi | 750-4,000 psi |
| 26 | 750-4,000 psi | 7,000-25,000 psi | 7,000-25,000 psi | 4,000-7,000 psi |
| 27 | 750-4,000 psi | 7,000-25,000 psi | 7,000-25,000 psi | 7,000-25,000 psi |
| 28 | 4,000-7,000 psi | 750-4,000 psi | 750-4,000 psi | 750-4,000 psi |
| 29 | 4,000-7,000 psi | 750-4,000 psi | 750-4,000 psi | 4,000-7,000 psi |
| 30 | 4,000-7,000 psi | 750-4,000 psi | 750-4,000 psi | 7,000-25,000 psi |
| 31 | 4,000-7,000 psi | 750-4,000 psi | 4,000-7,000 psi | 750-4,000 psi |
| 32 | 4,000-7,000 psi | 750-4,000 psi | 4,000-7,000 psi | 4,000-7,000 psi |
| 33 | 4,000-7,000 psi | 750-4,000 psi | 4,000-7,000 psi | 7,000-25,000 psi |
| 34 | 4,000-7,000 psi | 750-4,000 psi | 7,000-25,000 psi | 750-4,000 psi |
| 35 | 4,000-7,000 psi | 750-4,000 psi | 7,000-25,000 psi | 4,000-7,000 psi |
| 36 | 4,000-7,000 psi | 750-4,000 psi | 7,000-25,000 psi | 7,000-25,000 psi |
| 37 | 4,000-7,000 psi | 4,000-7,000 psi | 750-4,000 psi | 750-4,000 psi |
| 38 | 4,000-7,000 psi | 4,000-7,000 psi | 750-4,000 psi | 4,000-7,000 psi |
| 39 | 4,000-7,000 psi | 4,000-7,000 psi | 750-4,000 psi | 7,000-25,000 psi |
| 40 | 4,000-7,000 psi | 4,000-7,000 psi | 4,000-7,000 psi | 750-4,000 psi |
| 41 | 4,000-7,000 psi | 4,000-7,000 psi | 4,000-7,000 psi | 4,000-7,000 psi |
| 42 | 4,000-7,000 psi | 4,000-7,000 psi | 4,000-7,000 psi | 7,000-25,000 psi |
| 43 | 4,000-7,000 psi | 4,000-7,000 psi | 7,000-25,000 psi | 750-4,000 psi |
| 44 | 4,000-7,000 psi | 4,000-7,000 psi | 7,000-25,000 psi | 4,000-7,000 psi |
| 45 | 4,000-7,000 psi | 4,000-7,000 psi | 7,000-25,000 psi | 7,000-25,000 psi |
| 46 | 4,000-7,000 psi | 7,000-25,000 psi | 750-4,000 psi | 750-4,000 psi |
| 47 | 4,000-7,000 psi | 7,000-25,000 psi | 750-4,000 psi | 4,000-7,000 psi |
| 48 | 4,000-7,000 psi | 7,000-25,000 psi | 750-4,000 psi | 7,000-25,000 psi |
| 49 | 4,000-7,000 psi | 7,000-25,000 psi | 4,000-7,000 psi | 750-4,000 psi |
| 50 | 4,000-7,000 psi | 7,000-25,000 psi | 4,000-7,000 psi | 4,000-7,000 psi |
| 51 | 4,000-7,000 psi | 7,000-25,000 psi | 4,000-7,000 psi | 7,000-25,000 psi |
| 52 | 4,000-7,000 psi | 7,000-25,000 psi | 7,000-25,000 psi | 750-4,000 psi |
| 53 | 4,000-7,000 psi | 7,000-25,000 psi | 7,000-25,000 psi | 4,000-7,000 psi |
| 54 | 4,000-7,000 psi | 7,000-25,000 psi | 7,000-25,000 psi | 7,000-25,000 psi |
| 55 | 7,000-25,000 psi | 750-4,000 psi | 750-4,000 psi | 750-4,000 psi |
| 56 | 7,000-25,000 psi | 750-4,000 psi | 750-4,000 psi | 4,000-7,000 psi |
| 57 | 7,000-25,000 psi | 750-4,000 psi | 750-4,000 psi | 7,000-25,000 psi |
| 58 | 7,000-25,000 psi | 750-4,000 psi | 4,000-7,000 psi | 750-4,000 psi |
| 59 | 7,000-25,000 psi | 750-4,000 psi | 4,000-7,000 psi | 4,000-7,000 psi |
| 60 | 7,000-25,000 psi | 750-4,000 psi | 4,000-7,000 psi | 7,000-25,000 psi |
| 61 | 7,000-25,000 psi | 750-4,000 psi | 7,000-25,000 psi | 750-4,000 psi |
| 62 | 7,000-25,000 psi | 750-4,000 psi | 7,000-25,000 psi | 4,000-7,000 psi |
| 63 | 7,000-25,000 psi | 750-4,000 psi | 7,000-25,000 psi | 7,000-25,000 psi |
| 64 | 7,000-25,000 psi | 4,000-7,000 psi | 750-4,000 psi | 750-4,000 psi |
| 65 | 7,000-25,000 psi | 4,000-7,000 psi | 750-4,000 psi | 4,000-7,000 psi |
| 66 | 7,000-25,000 psi | 4,000-7,000 psi | 750-4,000 psi | 7,000-25,000 psi |
| 67 | 7,000-25,000 psi | 4,000-7,000 psi | 4,000-7,000 psi | 750-4,000 psi |

| No. | First FSFE pressure | Second FSFE pressure | Third FSFE pressure | Fourth FSFE pressure |
| --- | --- | --- | --- | --- |
| 68 | 7,000-25,000 psi | 4,000-7,000 psi | 4,000-7,000 psi | 4,000-7,000 psi |
| 69 | 7,000-25,000 psi | 4,000-7,000 psi | 4,000-7,000 psi | 7,000-25,000 psi |
| 70 | 7,000-25,000 psi | 4,000-7,000 psi | 7,000-25,000 psi | 750-4,000 psi |
| 71 | 7,000-25,000 psi | 4,000-7,000 psi | 7,000-25,000 psi | 4,000-7,000 psi |
| 72 | 7,000-25,000 psi | 4,000-7,000 psi | 7,000-25,000 psi | 7,000-25,000 psi |
| 73 | 7,000-25,000 psi | 7,000-25,000 psi | 750-4,000 psi | 750-4,000 psi |
| 74 | 7,000-25,000 psi | 7,000-25,000 psi | 750-4,000 psi | 4,000-7,000 psi |
| 75 | 7,000-25,000 psi | 7,000-25,000 psi | 750-4,000 psi | 7,000-25,000 psi |
| 76 | 7,000-25,000 psi | 7,000-25,000 psi | 4,000-7,000 psi | 750-4,000 psi |
| 77 | 7,000-25,000 psi | 7,000-25,000 psi | 4,000-7,000 psi | 4,000-7,000 psi |
| 78 | 7,000-25,000 psi | 7,000-25,000 psi | 4,000-7,000 psi | 7,000-25,000 psi |
| 79 | 7,000-25,000 psi | 7,000-25,000 psi | 7,000-25,000 psi | 750-4,000 psi |
| 80 | 7,000-25,000 psi | 7,000-25,000 psi | 7,000-25,000 psi | 4,000-7,000 psi |
| 81 | 7,000-25,000 psi | 7,000-25,000 psi | 7,000-25,000 psi | 7,000-25,000 psi |

Temperature

When the SFE is carried out two times, each FSFE can independently be carried out at a temperature of about: (i) −15-70° C., (ii) 70-100° C., or (iii) 100-200° C.

In specific embodiments, the SFE is carried out two times, wherein the first and second FSFEs are carried out at temperatures illustrated in any one of 1-9 below. When the first and second FSFEs are carried out at the same temperature range, those FSFEs will typically be carried out at a different pressure and/or solvent system having a different combination of polarity and proticity (e.g., carried out at the same pressure range, the first FSFE includes a polar aprotic solvent system and the second FSFE includes a nonpolar protic solvent system).

| No. | First FSFE temperature | Second FSFE temperature |
| --- | --- | --- |
| 1 | −15-70° C. | −15-70° C. |
| 2 | −15-70° C. | 70-100° C. |
| 3 | −15-70° C. | 100-200° C. |
| 4 | 70-100° C. | −15-70° C. |
| 5 | 70-100° C. | 70-100° C. |
| 6 | 70-100° C. | 100-200° C. |
| 7 | 100-200° C. | −15-70° C. |
| 8 | 100-200° C. | 70-100° C. |
| 9 | 100-200° C. | 100-200° C. |

When the SFE is carried out three times, each FSFE can independently be carried out at a temperature of about: (i) −15-70° C., (ii) 70-100° C., or (iii) 100-200° C.

In specific embodiments, the SFE is carried out three times, wherein the first, second and third FSFEs are carried out at temperatures illustrated in any one of 1-27 below. When the first, second and third FSFEs are carried out at the same temperature range, those FSFEs will typically be carried out at a different pressure and/or solvent system having a different combination of polarity and proticity (e.g., carried out at the same pressure range, the second FSFE includes a polar aprotic solvent system and the third FSFE includes a nonpolar protic solvent system).

| No. | First FSFE temperature | Second FSFE temperature | Third FSFE temperature |
| --- | --- | --- | --- |
| 1 | −15-70° C. | −15-70° C. | −15-70° C. |
| 2 | −15-70° C. | −15-70° C. | 70-100° C. |
| 3 | −15-70° C. | −15-70° C. | 100-200° C. |
| 4 | −15-70° C. | 70-100° C. | −15-70° C. |
| 5 | −15-70° C. | 70-100° C. | 70-100° C. |
| 6 | −15-70° C. | 70-100° C. | 100-200° C. |
| 7 | −15-70° C. | 100-200° C. | −15-70° C. |
| 8 | −15-70° C. | 100-200° C. | 70-100° C. |
| 9 | −15-70° C. | 100-200° C. | 100-200° C. |
| 10 | 70-100° C. | −15-70° C. | −15-70° C. |
| 11 | 70-100° C. | −15-70° C. | 70-100° C. |
| 12 | 70-100° C. | −15-70° C. | 100-200° C. |
| 13 | 70-100° C. | 70-100° C. | −15-70° C. |
| 14 | 70-100° C. | 70-100° C. | 70-100° C. |
| 15 | 70-100° C. | 70-100° C. | 100-200° C. |
| 16 | 70-100° C. | 100-200° C. | −15-70° C. |
| 17 | 70-100° C. | 100-200° C. | 70-100° C. |
| 18 | 70-100° C. | 100-200° C. | 100-200° C. |
| 19 | 100-200° C. | −15-70° C. | −15-70° C. |
| 20 | 100-200° C. | −15-70° C. | 70-100° C. |
| 21 | 100-200° C. | −15-70° C. | 100-200° C. |
| 22 | 100-200° C. | 70-100° C. | −15-70° C. |
| 23 | 100-200° C. | 70-100° C. | 70-100° C. |
| 24 | 100-200° C. | 70-100° C. | 100-200° C. |
| 25 | 100-200° C. | 100-200° C. | −15-70° C. |
| 26 | 100-200° C. | 100-200° C. | 70-100° C. |
| 27 | 100-200° C. | 100-200° C. | 100-200° C. |

When the SFE is carried out four times, each FSFE can independently be carried out at a temperature of about: (i) −15-70° C., (ii) 70-100° C., or (iii) 100-200° C.

In specific embodiments, the SFE is carried out four times, wherein the first, second, third and fourth FSFEs are carried out at temperatures illustrated in any one of 1-81 below. When the first, second, third and fourth FSFEs are carried out at the same temperature range, those FSFEs will typically be carried out at a different pressure and/or solvent system having a different combination of polarity and proticity (e.g., carried out at the same pressure range, the third FSFE includes a polar aprotic solvent system and the fourth FSFE includes a nonpolar protic solvent system).

| No. | First FSFE temperature | Second FSFE temperature | Third FSFE temperature | Fourth FSFE temperature |
| --- | --- | --- | --- | --- |
| 1 | −15-70° C. | −15-70° C. | −15-70° C. | −15-70° C. |
| 2 | −15-70° C. | −15-70° C. | −15-70° C. | 70-100° C. |
| 3 | −15-70° C. | −15-70° C. | −15-70° C. | 100-200° C. |
| 4 | −15-70° C. | −15-70° C. | 70-100° C. | −15-70° C. |
| 5 | −15-70° C. | −15-70° C. | 70-100° C. | 70-100° C. |
| 6 | −15-70° C. | −15-70° C. | 70-100° C. | 100-200° C. |
| 7 | −15-70° C. | −15-70° C. | 100-200° C. | −15-70° C. |
| 8 | −15-70° C. | −15-70° C. | 100-200° C. | 70-100° C. |
| 9 | −15-70° C. | −15-70° C. | 100-200° C. | 100-200° C. |
| 10 | −15-70° C. | 70-100° C. | −15-70° C. | −15-70° C. |
| 11 | −15-70° C. | 70-100° C. | −15-70° C. | 70-100° C. |
| 12 | −15-70° C. | 70-100° C. | −15-70° C. | 100-200° C. |
| 13 | −15-70° C. | 70-100° C. | 70-100° C. | −15-70° C. |
| 14 | −15-70° C. | 70-100° C. | 70-100° C. | 70-100° C. |
| 15 | −15-70° C. | 70-100° C. | 70-100° C. | 100-200° C. |
| 16 | −15-70° C. | 70-100° C. | 100-200° C. | −15-70° C. |
| 17 | −15-70° C. | 70-100° C. | 100-200° C. | 70-100° C. |
| 18 | −15-70° C. | 70-100° C. | 100-200° C. | 100-200° C. |
| 19 | −15-70° C. | 100-200° C. | −15-70° C. | −15-70° C. |
| 20 | −15-70° C. | 100-200° C. | −15-70° C. | 70-100° C. |
| 21 | −15-70° C. | 100-200° C. | −15-70° C. | 100-200° C. |
| 22 | −15-70° C. | 100-200° C. | 70-100° C. | −15-70° C. |
| 23 | −15-70° C. | 100-200° C. | 70-100° C. | 70-100° C. |
| 24 | −15-70° C. | 100-200° C. | 70-100° C. | 100-200° C. |
| 25 | −15-70° C. | 100-200° C. | 100-200° C. | −15-70° C. |
| 26 | −15-70° C. | 100-200° C. | 100-200° C. | 70-100° C. |
| 27 | −15-70° C. | 100-200° C. | 100-200° C. | 100-200° C. |

| No. | First FSFE temperature | Second FSFE temperature | Third FSFE temperature | Fourth FSFE temperature |
|---|---|---|---|---|
| 28 | 70-100° C. | −15-70° C. | −15-70° C. | −15-70° C. |
| 29 | 70-100° C. | −15-70° C. | −15-70° C. | 70-100° C. |
| 30 | 70-100° C. | −15-70° C. | −15-70° C. | 100-200° C. |
| 31 | 70-100° C. | −15-70° C. | 70-100° C. | −15-70° C. |
| 32 | 70-100° C. | −15-70° C. | 70-100° C. | 70-100° C. |
| 33 | 70-100° C. | −15-70° C. | 70-100° C. | 100-200° C. |
| 34 | 70-100° C. | −15-70° C. | 100-200° C. | −15-70° C. |
| 35 | 70-100° C. | −15-70° C. | 100-200° C. | 70-100° C. |
| 36 | 70-100° C. | −15-70° C. | 100-200° C. | 100-200° C. |
| 37 | 70-100° C. | 70-100° C. | −15-70° C. | −15-70° C. |
| 38 | 70-100° C. | 70-100° C. | −15-70° C. | 70-100° C. |
| 39 | 70-100° C. | 70-100° C. | −15-70° C. | 100-200° C. |
| 40 | 70-100° C. | 70-100° C. | 70-100° C. | −15-70° C. |
| 41 | 70-100° C. | 70-100° C. | 70-100° C. | 70-100° C. |
| 42 | 70-100° C. | 70-100° C. | 70-100° C. | 100-200° C. |
| 43 | 70-100° C. | 70-100° C. | 100-200° C. | −15-70° C. |
| 44 | 70-100° C. | 70-100° C. | 100-200° C. | 70-100° C. |
| 45 | 70-100° C. | 70-100° C. | 100-200° C. | 100-200° C. |
| 46 | 70-100° C. | 100-200° C. | −15-70° C. | −15-70° C. |
| 47 | 70-100° C. | 100-200° C. | −15-70° C. | 70-100° C. |
| 48 | 70-100° C. | 100-200° C. | −15-70° C. | 100-200° C. |
| 49 | 70-100° C. | 100-200° C. | 70-100° C. | −15-70° C. |
| 50 | 70-100° C. | 100-200° C. | 70-100° C. | 70-100° C. |
| 51 | 70-100° C. | 100-200° C. | 70-100° C. | 100-200° C. |
| 52 | 70-100° C. | 100-200° C. | 100-200° C. | −15-70° C. |
| 53 | 70-100° C. | 100-200° C. | 100-200° C. | 70-100° C. |
| 54 | 70-100° C. | 100-200° C. | 100-200° C. | 100-200° C. |
| 55 | 100-200° C. | −15-70° C. | −15-70° C. | −15-70° C. |
| 56 | 100-200° C. | −15-70° C. | −15-70° C. | 70-100° C. |
| 57 | 100-200° C. | −15-70° C. | −15-70° C. | 100-200° C. |
| 58 | 100-200° C. | −15-70° C. | 70-100° C. | −15-70° C. |
| 59 | 100-200° C. | −15-70° C. | 70-100° C. | 70-100° C. |
| 60 | 100-200° C. | −15-70° C. | 70-100° C. | 100-200° C. |
| 61 | 100-200° C. | −15-70° C. | 100-200° C. | −15-70° C. |
| 62 | 100-200° C. | −15-70° C. | 100-200° C. | 70-100° C. |
| 63 | 100-200° C. | −15-70° C. | 100-200° C. | 100-200° C. |
| 64 | 100-200° C. | 70-100° C. | −15-70° C. | −15-70° C. |
| 65 | 100-200° C. | 70-100° C. | −15-70° C. | 70-100° C. |
| 66 | 100-200° C. | 70-100° C. | −15-70° C. | 100-200° C. |
| 67 | 100-200° C. | 70-100° C. | 70-100° C. | −15-70° C. |
| 68 | 100-200° C. | 70-100° C. | 70-100° C. | 70-100° C. |
| 69 | 100-200° C. | 70-100° C. | 70-100° C. | 100-200° C. |
| 70 | 100-200° C. | 70-100° C. | 100-200° C. | −15-70° C. |
| 71 | 100-200° C. | 70-100° C. | 100-200° C. | 70-100° C. |
| 72 | 100-200° C. | 70-100° C. | 100-200° C. | 100-200° C. |
| 73 | 100-200° C. | 100-200° C. | −15-70° C. | −15-70° C. |
| 74 | 100-200° C. | 100-200° C. | −15-70° C. | 70-100° C. |
| 75 | 100-200° C. | 100-200° C. | −15-70° C. | 100-200° C. |
| 76 | 100-200° C. | 100-200° C. | 70-100° C. | −15-70° C. |
| 77 | 100-200° C. | 100-200° C. | 70-100° C. | 70-100° C. |
| 78 | 100-200° C. | 100-200° C. | 70-100° C. | 100-200° C. |
| 79 | 100-200° C. | 100-200° C. | 100-200° C. | −15-70° C. |
| 80 | 100-200° C. | 100-200° C. | 100-200° C. | 70-100° C. |
| 81 | 100-200° C. | 100-200° C. | 100-200° C. | 100-200° C. |

Prophetic Examples

The prophetic examples 1-8 below can be carried out employing techniques, materials, and equipment known to those reasonably skilled in the art.

General Description:

1 kg of freshly harvested *Cannabis sativa* is placed in a SFE extraction vessel (25 L). 10 L of solvent system is introduced into the SFE extraction vessel. The solvent system is initially cooled to maintain liquid conditions, then heated after pressurization. The desired temperature and pressure is achieved. The SFE extraction vessel is shaken to facilitate extraction. After the requisite period of time, the temperature and pressure are lowered to ambient conditions. The process is optionally repeated, one or more times. The spent plant material is separated from the extract, wherein the extract is optionally further processed to provide a concentrate.

| Number of SFEs/FSFEs | SFE Solvent System | SFE Pressure | SFE Temperature | SFE Time | *Cannabis* extract (expected) |
|---|---|---|---|---|---|
| Example 1: | | | | | |
| 1 | Polar protic ($CO_2$ and EtOH) | 3,500 psi | 60° C. | 60 min | cannabinolic acid (CBNA); $\Delta(9)$-tetrahydrocannabinolic acid ($\Delta(9)$-THCA); $\Delta(9)$-tetrahydrocannabidiolic acid ($\Delta(9)$-CBDA); $\Delta(8)$-tetrahydrocannabinolic acid ($\Delta(8)$-THCA); $\Delta(8)$-tetrahydrocannabidiolic acid ($\Delta(8)$-CBDA); $\Delta(9)$-tetrahydrocannabivarin ($\Delta(9)$-THV); cannabigerolic acid (CBGA); cannabichromenic acid (CBCA); and cannabicyclolic acid (CBLA) |
| Example 2: | | | | | |
| 1 | Nonpolar aprotic ($CO_2$ and pentanes) | 7,500 psi | 90° C. | 60 min | $\Delta(9)$-tetrahydrocannabinol ($\Delta(9)$-THC); cannabinol (CBN); $\Delta(9)$-cannabidiol ($\Delta(9)$-CBD); $\Delta(8)$-tetrahydrocannabinol ($\Delta(8)$-THC); $\Delta(8)$-tetrahydrocannabidiol ($\Delta(8)$-CBD); cannabigerol (CBG); cannabichromene (CBC); cannabicyclol (CBL); β-caryophyllene epoxide; mentha-1,8(9)-dien-5-ol; pulegone; limonene oxide; α-terpinene; terpinen-4-ol; |

-continued

| Number of SFEs/FSFEs | SFE Solvent System | SFE Pressure | SFE Temperature | SFE Time | *Cannabis* extract (expected) |
|---|---|---|---|---|---|
| | | | | | carvacrol; carvone; 1,8-cineole; p-cymene; fenchone; pulegone-1,2epoxide; β-myrcene; cannaflavin A; and cannaflavin B |

Example 3:

| 2 | i. Polar protic (CO$_2$ and EtOH) ii. Nonpolar aprotic (CO$_2$ and pentanes) | i. 1,500 psi ii. 7,500 psi | i. 80° C. ii. 70° C. | i. 24 min ii. 26 min | i. cannabinolic acid (CBNA); Δ(9)-tetrahydrocannabinolic acid (Δ(9)-THCA); Δ(9)-tetrahydrocannabidiolic acid (Δ(9)-CBDA); Δ(8)-tetrahydrocannabinolic acid (Δ(8)-THCA); Δ(8)-tetrahydrocannabidiolic acid (Δ(8)-CBDA); Δ(9)-tetrahydrocannabivarin (Δ(9)-THV); cannabigerolic acid (CBGA); cannabichromenic acid (CBCA); and cannabicyclolic acid (CBLA) ii. Δ(9)-tetrahydrocannabinol (Δ(9)-THC); cannabinol (CBN); Δ(9)-cannabidiol (Δ(9)-CBD); Δ(8)-tetrahydrocannabinol (Δ(8)-THC); Δ(8)-tetrahydrocannabidiol (Δ(8)-CBD); cannabigerol (CBG); cannabichromene (CBC); cannabicyclol (CBL); β-caryophyllene epoxide; mentha-1,8(9)-dien-5-ol; pulegone; limonene oxide; α-terpinene; terpinen-4-ol; carvacrol; carvone; 1,8-cineole; p-cymene; fenchone; pulegone-1,2epoxide; β-myrcene; cannaflavin A; and cannaflavin B |

Example 4:

| 2 | i. Nonpolar aprotic (CO$_2$ and pentanes) ii. Polar protic (CO$_2$ and EtOH) | i. 1,500 psi ii. 4,500 psi | i. 90° C. ii. 70° C. | i. 38 min ii. 34 min | i. Δ(9)-tetrahydrocannabinol (Δ(9)-THC); cannabinol (CBN); Δ(9)-cannabidiol (Δ(9)-CBD); Δ(8)-tetrahydrocannabinol (Δ(8)-THC); Δ(8)-tetrahydrocannabidiol (Δ(8)-CBD); cannabigerol (CBG); cannabichromene (CBC); cannabicyclol (CBL); β-caryophyllene epoxide; mentha-1,8(9)-dien-5-ol; pulegone; limonene oxide; α-terpinene; terpinen-4-ol; carvacrol; carvone; 1,8-cineole; p-cymene; fenchone; pulegone-1,2epoxide; β-myrcene; cannaflavin A; and cannaflavin B ii. cannabinolic acid (CBNA); Δ(9)-tetrahydrocannabinolic acid (Δ(9)-THCA); Δ(9)-tetrahydrocannabidiolic acid (Δ(9)-CBDA); |

-continued

| Number of SFEs/FSFEs | SFE Solvent System | SFE Pressure | SFE Temperature | SFE Time | Cannabis extract (expected) |
|---|---|---|---|---|---|
| | | | | | Δ(8)-tetrahydrocannabinolic acid (Δ(8)-THCA); Δ(8)-tetrahydrocannabidiolic acid (Δ(8)-CBDA); Δ(9)-tetrahydrocannabivarin (Δ(9)-THV); cannabigerolic acid (CBGA); cannabichromenic acid (CBCA); and cannabicyclolic acid (CBLA) |

Example 5:

| 2 | i. Polar protic ($CO_2$ and EtOH) ii. Nonpolar aprotic ($CO_2$ and pentanes) | i. 4,000 psi ii. 4,000 psi | i. 80° C. ii. 60° C. | i. 26 min ii. 28 min | i. cannabinolic acid (CBNA); Δ(9)-tetrahydrocannabinolic acid (Δ(9)-THCA); Δ(9)-tetrahydrocannabidiolic acid (Δ(9)-CBDA); Δ(8)-tetrahydrocannabinolic acid (Δ(8)-THCA); Δ(8)-tetrahydrocannabidiolic acid (Δ(8)-CBDA); Δ(9)-tetrahydrocannabivarin (Δ(9)-THV); cannabigerolic acid (CBGA); cannabichromenic acid (CBCA); and cannabicyclolic acid (CBLA) ii. Δ(9)-tetrahydrocannabinol (Δ(9)-THC); cannabinol (CBN); Δ(9)-cannabidiol (Δ(9)-CBD); Δ(8)-tetrahydrocannabinol (Δ(8)-THC); Δ(8)-tetrahydrocannabidiol (Δ(8)-CBD); cannabigerol (CBG); cannabichromene (CBC); cannabicyclol (CBL); β-caryophyllene epoxide; mentha-1,8(9)-dien-5-ol; pulegone; limonene oxide; α-terpinene; terpinen-4-ol; carvacrol; carvone; 1,8-cineole; p-cymene; fenchone; pulegone-1,2epoxide; β-myrcene; cannaflavin A; and cannaflavin B |

Example 6:

| 2 | i. Nonpolar aprotic ($CO_2$ and pentanes) ii. Polar protic ($CO_2$ and EtOH) | i. 5,000 psi ii. 5,000 psi | i. 110° C. ii. 80° C. | i. 37 min ii. 39 min | i. Δ(9)-tetrahydrocannabinol (Δ(9)-THC); cannabinol (CBN); Δ(9)-cannabidiol (Δ(9)-CBD); Δ(8)-tetrahydrocannabinol (Δ(8)-THC); Δ(8)-tetrahydrocannabidiol (Δ(8)-CBD); cannabigerol (CBG); cannabichromene (CBC); cannabicyclol (CBL); β-caryophyllene epoxide; mentha-1,8(9)-dien-5-ol; pulegone; limonene oxide; α-terpinene; terpinen-4-ol; carvacrol; carvone; 1,8-cineole; p-cymene; fenchone; pulegone-1,2epoxide; β-myrcene; cannaflavin A; and cannaflavin B ii. cannabinolic acid (CBNA); Δ(9)-tetrahydrocannabinolic acid (Δ(9)-THCA); Δ(9)-tetrahydrocannabidiolic acid (Δ(9)-CBDA); |

-continued

| Number of SFEs/FSFEs | SFE Solvent System | SFE Pressure | SFE Temperature | SFE Time | *Cannabis* extract (expected) |
|---|---|---|---|---|---|
| | | | | | Δ(8)-tetrahydrocannabinolic acid (Δ(8)-THCA); Δ(8)-tetrahydrocannabidiolic acid (Δ(8)-CBDA); Δ(9)-tetrahydrocannabivarin (Δ(9)-THV); cannabigerolic acid (CBGA); cannabichromenic acid (CBCA); and cannabicyclolic acid (CBLA) |

Example 7:

| 2 | i. Polar protic (CO₂ and EtOH) ii. Nonpolar aprotic (CO₂ and pentanes) | i. 1,500 psi ii. 7,500 psi | i. 110° C. ii. 110° C. | i. 34 min ii. 37 min | i. cannabinolic acid (CBNA); Δ(9)-tetrahydrocannabinolic acid (Δ(9)-THCA); Δ(9)-tetrahydrocannabidiolic acid (Δ(9)-CBDA); Δ(8)-tetrahydrocannabinolic acid (Δ(8)-THCA); Δ(8)-tetrahydrocannabidiolic acid (Δ(8)-CBDA); Δ(9)-tetrahydrocannabivarin (Δ(9)-THV); cannabigerolic acid (CBGA); cannabichromenic acid (CBCA); and cannabicyclolic acid (CBLA) ii. Δ(9)-tetrahydrocannabinol (Δ(9)-THC); cannabinol (CBN); Δ(9)-cannabidiol (Δ(9)-CBD); Δ(8)-tetrahydrocannabinol (Δ(8)-THC); Δ(8)-tetrahydrocannabidiol (Δ(8)-CBD); cannabigerol (CBG); cannabichromene (CBC); cannabicyclol (CBL); β-caryophyllene epoxide; mentha-1,8(9)-dien-5-ol; pulegone; limonene oxide; α-terpinene; terpinen-4-ol; carvacrol; carvone; 1,8-cineole; p-cymene; fenchone; pulegone-1,2epoxide; β-myrcene; cannaflavin A; and cannaflavin B |

Example 8:

| 2 | i. Nonpolar aprotic (CO₂ and pentanes) ii. Polar protic (CO₂ and EtOH) | i. 1,500 psi ii. 4,500 psi | i. 120° C. ii. 120° C. | i. 35 min ii. 38 min | i. Δ(9)-tetrahydrocannabinol (Δ(9)-THC); cannabinol (CBN); Δ(9)-cannabidiol (Δ(9)-CBD); Δ(8)-tetrahydrocannabinol (Δ(8)-THC); Δ(8)-tetrahydrocannabidiol (Δ(8)-CBD); cannabigerol (CBG); cannabichromene (CBC); cannabicyclol (CBL); β-caryophyllene epoxide; mentha-1,8(9)-dien-5-ol; pulegone; limonene oxide; α-terpinene; terpinen-4-ol; carvacrol; carvone; 1,8-cineole; p-cymene; fenchone; pulegone-1,2epoxide; β-myrcene; cannaflavin A; and cannaflavin B ii. cannabinolic acid (CBNA); Δ(9)-tetrahydrocannabinolic acid (Δ(9)-THCA); Δ(9)-tetrahydrocannabidiolic acid (Δ(9)-CBDA); |

| Number of SFEs/FSFEs | SFE Solvent System | SFE Pressure | SFE Temperature | SFE Time | Cannabis extract (expected) |
|---|---|---|---|---|---|
| | | | | | Δ(8)-tetrahydrocannabinolic acid (Δ(8)-THCA); Δ(8)-tetrahydrocannabidiolic acid (Δ(8)-CBDA); Δ(9)-tetrahydrocannabivarin (Δ(9)-THV); cannabigerolic acid (CBGA); cannabichromenic acid (CBCA); and cannabicyclolic acid (CBLA) |

Embodiments

Specific enumerated embodiments [1] to [146] provided below are for illustration purposes only, and do not otherwise limit the scope of the disclosed subject matter, as defined by the embodiments. These enumerated embodiments encompass all combinations, sub-combinations, and multiply referenced (e.g., multiply dependent) combinations described therein.

[1.] A process for obtaining an extract of Cannabis, the process including:

(a) contacting Cannabis with a supercritical fluid solvent system at a pressure between about 750 psi and 25,000 psi, and at a temperature between about −15° C. and 200° C., to provide an extract of Cannabis; and (b) optionally removing the supercritical fluid solvent system from the extract of Cannabis to provide a concentrate of Cannabis.

[2.] A process for obtaining an extract of Cannabis, the process including:

(a) contacting Cannabis plant material with a supercritical fluid solvent system at a pressure between about 750 psi and 25,000 psi, and at a temperature between about −15° C. and 200° C., to provide an extract of Cannabis and an extracted Cannabis;

(b) removing the supercritical fluid solvent system from the extract of Cannabis to provide a concentrate of Cannabis;

(c) contacting the extracted Cannabis plant material with a second supercritical fluid solvent system at a pressure between about 750 psi and 25,000 psi, and at a temperature between about −15° C. and 200° C., to provide a second extract of Cannabis and a second extracted Cannabis plant material; and (d) optionally removing the second supercritical fluid solvent system from the second extract of Cannabis to provide a second concentrate of Cannabis.

[3.] A process for obtaining an extract of Cannabis, the process including:

(a) contacting Cannabis with a supercritical fluid solvent system at a pressure between about 750 psi and 25,000 psi, and at a temperature between about −15° C. and 200° C., to provide an extract of Cannabis and an extracted Cannabis plant material;

(b) removing the supercritical fluid solvent system from the extract of Cannabis to provide a concentrate of Cannabis;

(c) contacting the extracted Cannabis plant material with a second supercritical fluid solvent system at a pressure between about 750 psi and 25,000 psi, and at a temperature between about −15° C. and 200° C., to provide a second extract of Cannabis and a second extracted Cannabis plant material;

(d) removing the second supercritical fluid solvent system from the second extract of Cannabis to provide a second concentrate of Cannabis;

(e) contacting the second extracted Cannabis plant material with a third supercritical fluid solvent system at a pressure between about 750 psi and 25,000 psi, and at a temperature between about −15° C. and 200° C., to provide a third extract of Cannabis and a third extracted Cannabis plant material; and (f) optionally removing the third supercritical fluid solvent system from the third extract of Cannabis to provide a third concentrate of Cannabis.

[4.] A process for obtaining an extract of Cannabis, the process including:

(a) contacting Cannabis with a supercritical fluid solvent system at a pressure between about 750 psi and 25,000 psi, and at a temperature between about −15° C. and 200° C., to provide an extract of Cannabis and an extracted Cannabis plant material;

(b) removing the supercritical fluid solvent system from the extract of Cannabis to provide a concentrate of Cannabis;

(c) contacting the extracted Cannabis plant material with a second supercritical fluid solvent system at a pressure between about 750 psi and 25,000 psi, and at a temperature between about −15° C. and 200° C., to provide a second extract of Cannabis and a second extracted Cannabis plant material;

(d) removing the second supercritical fluid solvent system from the second extract of Cannabis to provide a second concentrate of Cannabis;

(e) contacting the second extracted Cannabis plant material with a third supercritical fluid solvent system at a pressure between about 750 psi and 25,000 psi, and at a temperature between about −15° C. and 200° C., to provide a third extract of Cannabis and a third extracted Cannabis plant material;

(f) removing the third supercritical fluid solvent system from the third extract of Cannabis to provide a third concentrate of Cannabis;

(g) contacting the third extracted Cannabis plant material with a fourth supercritical fluid solvent system at a pressure between about 750 psi and 25,000 psi, and at a temperature between about −15° C. and 200° C., to provide a fourth extract of Cannabis and a fourth extracted Cannabis plant material; and (h) optionally removing the fourth supercritical fluid solvent system from the fourth extract of Cannabis to provide a fourth concentrate of Cannabis.

[5.] A process for obtaining a concentrate of Cannabis, the process including:

(a) contacting Cannabis plant material with a supercritical fluid solvent system, at a pressure between about 750 psi and 25,000 psi, and at a temperature between about −15° C. and 200° C., to provide an extract of *Cannabis*; and (b) removing the supercritical fluid solvent system from the extract;

wherein the (a) contacting of the *Cannabis* plant material with the supercritical fluid solvent system and the (b) removing the supercritical fluid solvent system, is carried out multiple times, such that the process is a fractional supercritical fluid extraction;

wherein each contacting of the *Cannabis* plant material with a supercritical fluid solvent system independently occurs at a pressure between about 750 psi and 25,000 psi, and independently occurs at a temperature between about −15° C. and 200° C.

[6.] The process of any one of embodiments [1]-[5], wherein the *Cannabis* plant material is fresh, having been harvested within the past 10 days.

[7.] The process of any one of embodiments [1]-[6], wherein the supercritical fluid solvent system is removed from the extract of *Cannabis*, to provide the concentrate of *Cannabis*.

[8.] The process of any one of embodiments [1]-[6], wherein the *Cannabis* plant material is dried, having a moisture content of less than about 10 wt. %.

[9.] The process of any one of embodiments [1]-[6], wherein the *Cannabis* plant material is dried, having a moisture content of less than about 5 wt. %.

[10.] The process of any one of embodiments [1]-[6], wherein the *Cannabis* plant material is dried, having a moisture content of less than about 1 wt. %.

[11.] The process of any one of embodiments [1]-[10], wherein the *Cannabis* plant material is a physical portion of a *Cannabis* plant.

[12.] The process of any one of embodiments [1]-[11], wherein the *Cannabis* plant material is a leaf, bud, trichome, seed, or any combination thereof, of a *Cannabis* plant.

[13.] The process of any one of embodiments [1]-[12], wherein the *Cannabis* plant comprises at least one of *Cannabis sativa* L., *Cannabis indica* Lam., and *Cannabis ruderalis* Janisch.

[14.] The process of any one of embodiments [1]-[13], wherein each pressure is independently between about 750 psi and 25,000 psi.

[15.] The process of any one of embodiments [1]-[14], wherein any one or more pressures is independently between about 750 psi and 1,500 psi.

[16.] The process of any one of embodiments [1]-[15], wherein one or more pressures is independently between about 1,500 psi and 4,000 psi.

[17.] The process of any one of embodiments [1]-[16], wherein one or more pressures is independently between about 4,000 psi and 25,000 psi.

[18.] The process of any one of embodiments [1]-[17], wherein each pressure is independently selected from (i) 750-4,000 psi, (ii) 4,000-7,000 psi, and (iii) 7,000-25,000 psi.

[19.] The process of any one of embodiments [1]-[17], wherein each fractional supercritical fluid extraction is carried out at a different range of pressure, each selected from (i) 750-4,000 psi, (ii) 4,000-7,000 psi, and (iii) 7,000-25,000 psi.

[20.] The process of any one of embodiments [1]-[19], wherein each temperature is independently between about −15° C. and 200° C.

[21.] The process of any one of embodiments [1]-[20], wherein any one or more temperatures is independently between about 25° C. and 60° C.

[22.] The process of any one of embodiments [1]-[21], wherein any one or more temperatures is independently between about 60° C. and 110° C.

[23.] The process of any one of embodiments [1]-[22], wherein any one or more temperatures is independently between about 110° C. and 200° C.

[24.] The process of any one of embodiments [1]-[23], wherein each temperature is independently selected from (i) −15-70° C., (ii) 70-100° C., and (iii) 100-200° C.

[25.] The process of any one of embodiments [1]-[24], wherein each fractional supercritical fluid extraction is carried out at a different range of temperature, each selected from (i) −15-70° C., (ii) 70-100° C., and (iii) 100-200° C.

[26.] The process of any one of embodiments [1]-[25], wherein each supercritical fluid solvent system is independently:

(i) a polar aprotic supercritical fluid solvent system,
(ii) a polar protic supercritical fluid solvent system,
(iii) a nonpolar aprotic supercritical fluid solvent system, or
(iv) a nonpolar protic supercritical fluid solvent system.

[27.] The process of embodiment [25], wherein the selection of each supercritical fluid solvent system is mutually exclusive of all other supercritical fluid solvent systems, regarding the designation of the combination of polarity and proticity.

[28.] The process of embodiment [25], wherein the selection of each supercritical fluid solvent system is the same to all other supercritical fluid solvent systems, regarding the designation of the combination of polarity and proticity.

[29.] The process of any one of embodiments [1]-[25], wherein each fractional supercritical fluid extraction is independently carried out employing a supercritical fluid solvent system which is: (i) polar aprotic, (ii) polar protic, (iii) nonpolar aprotic, or (iv) nonpolar protic.

[30.] The process of any one of embodiments [1]-[25], wherein each fractional supercritical fluid extraction is carried out with a different supercritical fluid solvent system, each selected from: (i) polar aprotic, (ii) polar protic, (iii) nonpolar aprotic, and (iv) nonpolar protic.

[31.] The process of any one of embodiments [1]-[25], wherein each supercritical fluid solvent system includes at least one of:

carbon dioxide ($CO_2$),
hydrogen ($H_2$),
neon (Ne),
nitrogen ($N_2$),
argon (Ar),
methane ($CH_4$),
ethane ($CH_3CH_3$),
propane ($CH_3CH_2CH_3$),
ammonia ($NH_3$),
water ($H_2O$),
xenon (Xe),
methanol,
ethanol,
1-propanol,
2-propanol,
1-hexanol,
2-methoxy ethanol,
tetrahydrofuran (THF),
1,4-dioxane,
acetonitrile,
methylene chloride,
dichloroethane,
chloroform,
ethyl acetate, propylene carbonate,
N,N-dimethylaceamide,
dimethyl sulfoxide (DMSO),
formic acid,
carbon disulfide,
acetone,
toluene,
hexanes,
pentanes,
trifluoromethane (Freon® 23),
nitrous oxide ($N_2O$),
sulfur hexafluroide ($SF_6$),
butane (n-$C_4H_{10}$),
isobutane (i-$C_4H_{10}$),
ethyl ether (($C_2H_5)_2O$),
benzotrifluoride ($C_6H_5CF_3$),
(p-chlorophenyl)trifluoromethane (Cl$C_6H_4CF_3$),
chlorofluorocarbon (CFC),
hydrofluorocarbon (HFA), and
HFA-134a (1,1,1,2-tetrafluoroethane).

[32.] The process of any one of embodiments [1]-[25], wherein each supercritical fluid solvent system includes carbon dioxide ($CO_2$) and at least one of:
hydrogen ($H_2$),
neon (Ne),
nitrogen ($N_2$),
argon (Ar),
methane ($CH_4$),
ethane ($CH_3CH_3$),
propane ($CH_3CH_2CH_3$),
ammonia ($NH_3$),
water ($H_2O$),
xenon (Xe),
methanol,
ethanol,
1-propanol,
2-propanol,
1-hexanol,
2-methoxy ethanol,
tetrahydrofuran (THF),
1,4-dioxane,
acetonitrile,
methylene chloride,
dichloroethane,
chloroform,
ethyl acetate,
propylene carbonate,
N,N-dimethylaceamide,
dimethyl sulfoxide (DMSO),
formic acid,
carbon disulfide,
acetone,
toluene,
hexanes,
pentanes,
trifluoromethane (Freon® 23),
nitrous oxide ($N_2O$),
sulfur hexafluroide ($SF_6$),
butane (n-$C_4H_{10}$),
isobutane (i-$C_4H_{10}$),
ethyl ether (($C_2H_5)_2O$),
benzotrifluoride ($C_6H_5CF_3$),
(p-chlorophenyl)trifluoromethane (Cl$C_6H_4CF_3$),
chlorofluorocarbon (CFC),
hydrofluorocarbon (HFA), and
HFA-134a (1,1,1,2-tetrafluoroethane).

[33.] The process of any one of embodiments [1]-[32], wherein the extract of *Cannabis* comprises an extract of at least one of kief and hashish.

[34.] The process of any one of embodiments [1]-[33], wherein any one or more extract of *Cannabis* comprises a concentrate comprising at least one of cannabinoids, terpenoids, and flavonoids.

[35.] The process of any one of embodiments [1]-[34], wherein any one or more extract of *Cannabis* comprises at least one of:
cannabinol (CBN),
cannabinolic acid (CBNA),
Δ(9)-tetrahydrocannabinol (Δ(9)-THC),
Δ(9)-tetrahydrocannabinolic acid (Δ(9)-THCA),
Δ(9)-cannabidiol (Δ(9)-CBD),
Δ(9)-tetrahydrocannabidiolic acid (Δ(9)-CBDA),
Δ(8)-tetrahydrocannabinol (Δ(8)-THC),
Δ(8)-tetrahydrocannabinolic acid (Δ(8)-THCA),
Δ(8)-tetrahydrocannabidiol (Δ(8)-CBD),
Δ(8)-tetrahydrocannabidiolic acid (Δ(8)-CBDA),
Δ(9)-tetrahydrocannabivarin (Δ(9)-THV),
cannabigerol (CBG),
cannabigerolic acid (CBGA),
cannabichromene (CBC),
cannabichromenic acid (CBCA),
cannabicyclol (CBL),
cannabicyclolic acid (CBLA),
β-caryophyllene epoxide,
mentha-1,8(9)-dien-5-ol,
pulegone,
limonene,
limonene oxide,
α-terpinene,
terpinen-4-ol,
carvacrol,
carvone,
1,8-cineole,
p-cymene,
fenchone,
pulegone-1,2epoxide,
β-myrcene,
cannaflavin A, and
cannaflavin B.

[36.] The process of any one of embodiments [1]-[35], wherein any one or more extract or concentrate of *Cannabis*, relative to the *Cannabis* plant material, is at least partially purified from at least one of terpenes, alkaloids, hemp oil, and cannabinoid acids.

[37.] The process of any one of embodiments [1]-[24], wherein any one or more extract or concentrate of *Cannabis*, relative to the *Cannabis* plant material, is at least partially purified from terpenes.

[38.] The process of any one of embodiments [1]-[37], which is a fractional supercritical fluid extraction, such that the (a) contacting of *Cannabis* plant material with the supercritical fluid solvent system, and the (b) removing the supercritical fluid solvent system to provide a concentrate of *Cannabis*, is carried out multiple times.

[39.] The process of any one of embodiments [1]-[37], which is a fractional supercritical fluid extraction, such that the (a) contacting *Cannabis* plant material with the supercritical fluid solvent system and the (b) removing the supercritical fluid solvent system to provide a concentrate of *Cannabis*, is carried out multiple times, each pressure independently between about 750 psi and 25,000 psi, each temperature independently between about −15° C. and 200° C., and each solvent system independently selected.

[40.] The process of any one of embodiments [1]-[37], which is a fractional supercritical fluid extraction, such that after removing the supercritical fluid solvent system to provide a concentrate of *Cannabis*, the extracted *Cannabis* plant material is contacted with a subsequent supercritical fluid solvent system at a pressure between about 750 psi and 25,000 psi, and at a temperature between about −15° C. and 200° C., to provide a subsequent extract of *Cannabis*, and the subsequent supercritical fluid solvent system is removed from the subsequent extract to provide a subsequent concentrate of *Cannabis*.

[41.] The process of any one of embodiments [1]-[40], further comprising combining any two or more of the multiple extracts or concentrates of *Cannabis*.

[42.] The process of any one of embodiments [1]-[41], further comprising discarding any one or more of the multiple extracts or concentrates of *Cannabis*.

[43.] The process of any one of embodiments [1]-[42], further comprising purifying any one or more extracts or concentrates of *Cannabis*, or combination thereof.

[44.] The process of any one of embodiments [1]-[43], further comprising purifying any one or more extracts or concentrates of *Cannabis*, or combination thereof, employing at least one of chromatography, adsorption, crystallization, distillation, liquid-liquid extraction, filtration, fractional distillation, precipitation, recrystallization, and sublimation.

[45.] An extract or concentrate of *Cannabis* obtained by the process of any one of embodiments [1]-[44].

[46.] A pharmaceutical dosage form that includes a *Cannabis* concentrate including at least one of cannabinol (CBN); cannabinolic acid (CBNA); Δ(9)-tetrahydrocannabinol (Δ(9)-THC); Δ(9)-tetrahydrocannabinolic acid (Δ(9)-THCA); Δ(9)-cannabidiol (Δ(9)-CBD); Δ(9)-tetrahydrocannabidiolic acid (Δ(9)-CBDA); Δ(8)-tetrahydrocannabinol (Δ(8)-THC); Δ(8)-tetrahydrocannabinolic acid (Δ(8)-THCA); Δ(8)-tetrahydrocannabidiol (Δ(8)-CBD); Δ(8)-tetrahydrocannabidiolic acid (Δ(8)-CBDA); Δ(9)-tetrahydrocannabivarin (Δ(9)-THV); cannabigerol (CBG); cannabigerolic acid (CBGA); cannabichromene (CBC); cannabichromenic acid (CBCA); cannabicyclol (CBL); cannabicyclolic acid (CBLA); β-caryophyllene epoxide; mentha-1,8(9)-dien-5-ol; pulegone; limonene; limonene oxide; α-terpinene; terpinen-4-ol; carvacrol; carvone; 1,8-cineole; p-cymene; fenchone; pulegone-1,2epoxide; β-myrcene; cannaflavin A; and cannaflavin B.

[47.] The pharmaceutical dosage form of embodiment [46], wherein compared to the *Cannabis* plant material, the *Cannabis* concentrate is enriched in at least one of cannabinol (CBN); cannabinolic acid (CBNA); Δ(9)-tetrahydrocannabinol (Δ(9)-THC); Δ(9)-tetrahydrocannabinolic acid (Δ(9)-THCA); Δ(9)-cannabidiol (Δ(9)-CBD); Δ(9)-tetrahydrocannabidiolic acid (Δ(9)-CBDA); Δ(8)-tetrahydrocannabinol (Δ(8)-THC); Δ(8)-tetrahydrocannabinolic acid (Δ(8)-THCA); Δ(8)-tetrahydrocannabidiol (Δ(8)-CBD); Δ(8)-tetrahydrocannabidiolic acid (Δ(8)-CBDA); Δ(9)-tetrahydrocannabivarin (Δ(9)-THV); cannabigerol (CBG); cannabigerolic acid (CBGA); cannabichromene (CBC); cannabichromenic acid (CBCA); cannabicyclol (CBL); cannabicyclolic acid (CBLA); β-caryophyllene epoxide; mentha-1,8(9)-dien-5-ol; pulegone; limonene; limonene oxide; α-terpinene; terpinen-4-ol; carvacrol; carvone; 1,8-cineole; p-cymene; fenchone; pulegone-1,2epoxide; β-myrcene; cannaflavin A; and cannaflavin B.

[48.] The pharmaceutical dosage form of any one of embodiments [46]-[47], wherein compared to the *Cannabis* plant material, the *Cannabis* concentrate includes a higher relative concentration of cannabinol (CBN).

[49.] The pharmaceutical dosage form of any one of embodiments [46]-[47], wherein compared to the *Cannabis* plant material, the *Cannabis* concentrate includes a lower relative concentration of cannabinol (CBN).

[50.] The pharmaceutical dosage form of any one of embodiments [46]-[49], wherein compared to the *Cannabis* plant material, the *Cannabis* concentrate includes a higher relative concentration of cannabinolic acid (CBNA).

[51.] The pharmaceutical dosage form of any one of embodiments [46]-[49], wherein compared to the *Cannabis* plant material, the *Cannabis* concentrate includes a lower relative concentration of cannabinolic acid (CBNA).

[52.] The pharmaceutical dosage form of any one of embodiments [46]-[51], wherein compared to the *Cannabis* plant material, the *Cannabis* concentrate includes a higher relative concentration of Δ(9)-tetrahydrocannabinol (Δ(9)-THC).

[53.] The pharmaceutical dosage form of any one of embodiments [46]-[51], wherein compared to the *Cannabis* plant material, the *Cannabis* concentrate includes a lower relative concentration of Δ(9)-tetrahydrocannabinol (Δ(9)-THC).

[54.] The pharmaceutical dosage form of any one of embodiments [46]-[53], wherein compared to the *Cannabis* plant material, the *Cannabis* concentrate includes a higher relative concentration of Δ(9)-tetrahydrocannabinolic acid (Δ(9)-THCA).

[55.] The pharmaceutical dosage form of any one of embodiments [46]-[53], wherein compared to the *Cannabis* plant material, the *Cannabis* concentrate includes a lower relative concentration of Δ(9)-tetrahydrocannabinolic acid (Δ(9)-THCA).

[56.] The pharmaceutical dosage form of any one of embodiments [46]-[55], wherein compared to the *Cannabis* plant material, the *Cannabis* concentrate includes a higher relative concentration of Δ(9)-cannabidiol (Δ(9)-CBD).

[57.] The pharmaceutical dosage form of any one of embodiments [46]-[55], wherein compared to the *Cannabis* plant material, the *Cannabis* concentrate includes a lower relative concentration of Δ(9)-cannabidiol (Δ(9)-CBD).

[58.] The pharmaceutical dosage form of any one of embodiments [46]-[57], wherein compared to the *Cannabis* plant material, the *Cannabis* concentrate includes a higher relative concentration of Δ(9)-tetrahydrocannabidiolic acid (Δ(9)-CBDA).

[59.] The pharmaceutical dosage form of any one of embodiments [46]-[57], wherein compared to the *Cannabis* plant material, the *Cannabis* concentrate includes a lower relative concentration of Δ(9)-tetrahydrocannabidiolic acid (Δ(9)-CBDA).

[60.] The pharmaceutical dosage form of any one of embodiments [46]-[59], wherein compared to the *Cannabis* plant material, the *Cannabis* concentrate includes a higher relative concentration of Δ(8)-tetrahydrocannabinol (Δ(8)-THC).

[61.] The pharmaceutical dosage form of any one of embodiments [46]-[59], wherein compared to the *Cannabis* plant material, the *Cannabis* concentrate includes a lower relative concentration of Δ(8)-tetrahydrocannabinol (Δ(8)-THC).

[62.] The pharmaceutical dosage form of any one of embodiments [46]-[61], wherein compared to the *Cannabis* plant material, the *Cannabis* concentrate includes a higher relative concentration of Δ(8)-tetrahydrocannabinolic acid (Δ(8)-THCA).

[63.] The pharmaceutical dosage form of any one of embodiments [46]-[61], wherein compared to the *Cannabis* plant material, the *Cannabis* concentrate includes a lower relative concentration of Δ(8)-tetrahydrocannabinolic acid (Δ(8)-THCA).

[64.] The pharmaceutical dosage form of any one of embodiments [46]-[63], wherein compared to the *Cannabis* plant material, the *Cannabis* concentrate includes a higher relative concentration of Δ(8)-tetrahydrocannabidiol (Δ(8)-CBD).

[65.] The pharmaceutical dosage form of any one of embodiments [46]-[63], wherein compared to the *Cannabis* plant material, the *Cannabis* concentrate includes a lower relative concentration of Δ(8)-tetrahydrocannabidiol (Δ(8)-CBD).

[66.] The pharmaceutical dosage form of any one of embodiments [46]-[65], wherein compared to the *Cannabis* plant material, the *Cannabis* concentrate includes a higher relative concentration of Δ(8)-tetrahydrocannabidiolic acid (Δ(8)-CBDA).

[67.] The pharmaceutical dosage form of any one of embodiments [46]-[65], wherein compared to the *Cannabis* plant material, the *Cannabis* concentrate includes a lower relative concentration of Δ(8)-tetrahydrocannabidiolic acid (Δ(8)-CBDA).

[68.] The pharmaceutical dosage form of any one of embodiments [46]-[67], wherein compared to the *Cannabis* plant material, the *Cannabis* concentrate includes a higher relative concentration of Δ(9)-tetrahydrocannabivarin (Δ(9)-THV).

[69.] The pharmaceutical dosage form of any one of embodiments [46]-[67], wherein compared to the *Cannabis* plant material, the *Cannabis* concentrate includes a lower relative concentration of Δ(9)-tetrahydrocannabivarin (Δ(9)-THV).

[70.] The pharmaceutical dosage form of any one of embodiments [46]-[69], wherein compared to the *Cannabis* plant material, the *Cannabis* concentrate includes a higher relative concentration of cannabigerol (CBG).

[71.] The pharmaceutical dosage form of any one of embodiments [46]-[69], wherein compared to the *Cannabis* plant material, the *Cannabis* concentrate includes a lower relative concentration of cannabigerol (CBG).

[72.] The pharmaceutical dosage form of any one of embodiments [46]-[71], wherein compared to the *Cannabis* plant material, the *Cannabis* concentrate includes a higher relative concentration of cannabigerolic acid (CBGA).

[73.] The pharmaceutical dosage form of any one of embodiments [46]-[71], wherein compared to the *Cannabis* plant material, the *Cannabis* concentrate includes a lower relative concentration of cannabigerolic acid (CBGA).

[74.] The pharmaceutical dosage form of any one of embodiments [46]-[73], wherein compared to the *Cannabis* plant material, the *Cannabis* concentrate includes a higher relative concentration of cannabichromene (CBC).

[75.] The pharmaceutical dosage form of any one of embodiments [46]-[73], wherein compared to the *Cannabis* plant material, the *Cannabis* concentrate includes a lower relative concentration of cannabichromene (CBC).

[76.] The pharmaceutical dosage form of any one of embodiments [46]-[75], wherein compared to the *Cannabis* plant material, the *Cannabis* concentrate includes a higher relative concentration of cannabichromenic acid (CBCA).

[77.] The pharmaceutical dosage form of any one of embodiments [46]-[75], wherein compared to the *Cannabis* plant material, the *Cannabis* concentrate includes a lower relative concentration of cannabichromenic acid (CBCA).

[78.] The pharmaceutical dosage form of any one of embodiments [46]-[77], wherein compared to the *Cannabis* plant material, the *Cannabis* concentrate includes a higher relative concentration of cannabicyclol (CBL).

[79.] The pharmaceutical dosage form of any one of embodiments [46]-[77], wherein compared to the *Cannabis* plant material, the *Cannabis* concentrate includes a lower relative concentration of cannabicyclol (CBL).

[80.] The pharmaceutical dosage form of any one of embodiments [46]-[79], wherein compared to the *Cannabis* plant material, the *Cannabis* concentrate includes a higher relative concentration of cannabicyclolic acid (CBLA).

[81.] The pharmaceutical dosage form of any one of embodiments [46]-[79], wherein compared to the *Cannabis* plant material, the *Cannabis* concentrate includes a lower relative concentration of cannabicyclolic acid (CBLA).

[82.] The pharmaceutical dosage form of any one of embodiments [46]-[81], wherein compared to the *Cannabis* plant material, the *Cannabis* concentrate includes a higher relative concentration of β-caryophyllene epoxide.

[83.] The pharmaceutical dosage form of any one of embodiments [46]-[81], wherein compared to the *Cannabis* plant material, the *Cannabis* concentrate includes a lower relative concentration of β-caryophyllene epoxide.

[84.] The pharmaceutical dosage form of any one of embodiments [46]-[83], wherein compared to the *Cannabis* plant material, the *Cannabis* concentrate includes a higher relative concentration of mentha-1, 8(9)-dien-5-ol.

[85.] The pharmaceutical dosage form of any one of embodiments [46]-[83], wherein compared to the *Cannabis* plant material, the *Cannabis* concentrate includes a lower relative concentration of mentha-1, 8(9)-dien-5-ol.

[86.] The pharmaceutical dosage form of any one of embodiments [46]-[85], wherein compared to the *Cannabis* plant material, the *Cannabis* concentrate includes a higher relative concentration of pulegone.

[87.] The pharmaceutical dosage form of any one of embodiments [46]-[85], wherein compared to the *Cannabis* plant material, the *Cannabis* concentrate includes a lower relative concentration of pulegone.

[88.] The pharmaceutical dosage form of any one of embodiments [46]-[87], wherein compared to the *Cannabis* plant material, the *Cannabis* concentrate includes a higher relative concentration of limonene.

[89.] The pharmaceutical dosage form of any one of embodiments [46]-[87], wherein compared to the *Cannabis* plant material, the *Cannabis* concentrate includes a lower relative concentration of limonene.

[90.] The pharmaceutical dosage form of any one of embodiments [46]-[89], wherein compared to the *Cannabis* plant material, the *Cannabis* concentrate includes a higher relative concentration of limonene oxide.

[91.] The pharmaceutical dosage form of any one of embodiments [46]-[89], wherein compared to the *Cannabis* plant material, the *Cannabis* concentrate includes a lower relative concentration of limonene oxide.

[92.] The pharmaceutical dosage form of any one of embodiments [46]-[91], wherein compared to the *Cannabis* plant material, the *Cannabis* concentrate includes a higher relative concentration of α-terpinene.

[93.] The pharmaceutical dosage form of any one of embodiments [46]-[91], wherein compared to the *Cannabis* plant material, the *Cannabis* concentrate includes a lower relative concentration of α-terpinene.

[94.] The pharmaceutical dosage form of any one of embodiments [46]-[93], wherein compared to the *Cannabis* plant material, the *Cannabis* concentrate includes a higher relative concentration of terpinen-4-ol.

[95.] The pharmaceutical dosage form of any one of embodiments [46]-[93], wherein compared to the *Cannabis* plant material, the *Cannabis* concentrate includes a lower relative concentration of terpinen-4-ol.

[96.] The pharmaceutical dosage form of any one of embodiments [46]-[95], wherein compared to the *Cannabis* plant material, the *Cannabis* concentrate includes a higher relative concentration of carvacrol.

[97.] The pharmaceutical dosage form of any one of embodiments [46]-[95], wherein compared to the *Cannabis* plant material, the *Cannabis* concentrate includes a lower relative concentration of carvacrol.

[98.] The pharmaceutical dosage form of any one of embodiments [46]-[97], wherein compared to the *Cannabis* plant material, the *Cannabis* concentrate includes a higher relative concentration of carvone.

[99.] The pharmaceutical dosage form of any one of embodiments [46]-[97], wherein compared to the *Cannabis* plant material, the *Cannabis* concentrate includes a lower relative concentration of carvone.

[100.] The pharmaceutical dosage form of any one of embodiments [46]-[99], wherein compared to the *Cannabis* plant material, the *Cannabis* concentrate includes a higher relative concentration of 1,8-cineole.

[101.] The pharmaceutical dosage form of any one of embodiments [46]-[99], wherein compared to the *Cannabis* plant material, the *Cannabis* concentrate includes a lower relative concentration of 1,8-cineole.

[102.] The pharmaceutical dosage form of any one of embodiments [46]-[101], wherein compared to the *Cannabis* plant material, the *Cannabis* concentrate includes a higher relative concentration of p-cymene.

[103.] The pharmaceutical dosage form of any one of embodiments [46]-[101], wherein compared to the *Cannabis* plant material, the *Cannabis* concentrate includes a lower relative concentration of p-cymene.

[104.] The pharmaceutical dosage form of any one of embodiments [46]-[103], wherein compared to the *Cannabis* plant material, the *Cannabis* concentrate includes a higher relative concentration of fenchone.

[105.] The pharmaceutical dosage form of any one of embodiments [46]-[103], wherein compared to the *Cannabis* plant material, the *Cannabis* concentrate includes a lower relative concentration of fenchone.

[106.] The pharmaceutical dosage form of any one of embodiments [46]-[105], wherein compared to the *Cannabis* plant material, the *Cannabis* concentrate includes a higher relative concentration of pulegone-1,2epoxide.

[107.] The pharmaceutical dosage form of any one of embodiments [46]-[105], wherein compared to the *Cannabis* plant material, the *Cannabis* concentrate includes a lower relative concentration of pulegone-1,2epoxide.

[108.] The pharmaceutical dosage form of any one of embodiments [46]-[107], wherein compared to the *Cannabis* plant material, the *Cannabis* concentrate includes a higher relative concentration of β-myrcene.

[109.] The pharmaceutical dosage form of any one of embodiments [46]-[107], wherein compared to the *Cannabis* plant material, the *Cannabis* concentrate includes a lower relative concentration of β-myrcene.

[110.] The pharmaceutical dosage form of any one of embodiments [46]-[109], wherein compared to the *Cannabis* plant material, the *Cannabis* concentrate includes a higher relative concentration of cannaflavin A.

[111.] The pharmaceutical dosage form of any one of embodiments [46]-[109], wherein compared to the *Cannabis* plant material, the *Cannabis* concentrate includes a lower relative concentration of cannaflavin A.

[112.] The pharmaceutical dosage form of any one of embodiments [46]-[111], wherein compared to the *Cannabis* plant material, the *Cannabis* concentrate includes a higher relative concentration of cannaflavin B.

[113.] The pharmaceutical dosage form of any one of embodiments [46]-[111], wherein compared to the *Cannabis* plant material, the *Cannabis* concentrate includes a lower relative concentration of cannaflavin B.

[114.] The pharmaceutical dosage form of embodiment [46], wherein compared to the *Cannabis* plant material, the *Cannabis* concentrate includes a higher relative concentration of each of cannabinol (CBN); cannabinolic acid (CBNA); $\Delta(9)$-tetrahydrocannabinol ($\Delta(9)$-THC); $\Delta(9)$-tetrahydrocannabinolic acid ($\Delta(9)$-THCA); $\Delta(9)$-cannabidiol ($\Delta(9)$-CBD); $\Delta(9)$-tetrahydrocannabidiolic acid ($\Delta(9)$-CBDA); $\Delta(8)$-tetrahydrocannabinol ($\Delta(8)$-THC); $\Delta(8)$-tetrahydrocannabinolic acid ($\Delta(8)$-THCA); $\Delta(8)$-tetrahydrocannabidiol ($\Delta(8)$-CBD); $\Delta(8)$-tetrahydrocannabidiolic acid ($\Delta(8)$-CBDA); $\Delta(9)$-tetrahydrocannabivarin ($\Delta(9)$-THV); cannabigerol (CBG); cannabigerolic acid (CBGA); cannabichromene (CBC); cannabichromenic acid (CBCA); cannabicyclol (CBL); cannabicyclolic acid (CBLA); β-caryophyllene epoxide; mentha-1,8(9)-dien-5-ol; pulegone; limonene; limonene oxide; α-terpinene; terpinen-4-ol; carvacrol; carvone; 1,8-cineole; p-cymene; fenchone; pulegone-1,2epoxide; β-myrcene; cannaflavin A; and cannaflavin B.

[115.] A pharmaceutical dosage form comprising a supercritical fluid extract or concentrate of *Cannabis*.

[116.] A pharmaceutical dosage form comprising a fractional supercritical fluid extract or concentrate of *Cannabis*.

[117.] The pharmaceutical dosage form of any one of embodiments [46]-[116], wherein the *Cannabis* concentrate is obtained by the process of any one of embodiments [1]-[44].

[118.] A pharmaceutical dosage form comprising the extract or concentrate of embodiment [45].

[119.] The pharmaceutical dosage form of any one of embodiments [46]-[118], which is suitable for oral delivery, ophthalmic delivery, nasal delivery, or dermal delivery.

[120.] The pharmaceutical dosage form of any one of embodiments [46]-[119], which is in the form of a pill, osmotic delivery system, elixir, emulsion, hydrogel, suspension, syrup, capsule, tablet, orally dissolving tablet (ODT), gel capsule, thin film, oral thin film (OTF), adhesive topical patch, lollipop, lozenge, chewing gum, dry powder inhaler (DPI), vaporizer, nebulizer, metered dose inhaler (MDI), ointment, transdermal patch, intradermal implant, subcutaneous implant, or transdermal implant.

[121.] The pharmaceutical dosage form of any one of embodiments [46]-[120], which is in the form of a transdermal patch.

[122.] The pharmaceutical dosage form of any one of embodiments [46]-[120], which is in the form of a thin film.

[123.] The pharmaceutical dosage form of any one of embodiments [46]-[120], which is in the form of an oral thin film (OTF).

[124.] The pharmaceutical dosage form of any one of embodiments [46]-[120], which is in the form of an orally dissolving tablet (ODT).

[125.] A method of treating a mammal afflicted with a disease or disorder, the method including administering to a mammal in need of such treatment, the pharmaceutical dosage form of any one of embodiments [46]-[124], in an amount and for a period of time, effective to treat the disease or disorder.

[126.] The method of embodiment [125], wherein the disease or disorder includes any one or more of:
neuroinflammation,
epilepsy, Alzheimer's disease,
oxidative injury,
vomiting and nausea,
anxiety,
anorexia,
arthritis,
schizophrenia,
multiple sclerosis,
joint inflammation,
joint pain,
symptoms associated with AIDS,
chronic pain,
acute pain,
anxiety,
neuropathic pain and spasticity,
inflammatory bowel diseases (IBD),
tumour neovascularization,
tumor growth,
cancer,
glaucoma,
muscle spasms,
severe pain,
severe nausea,
cachexia or dramatic weight loss and muscle atrophy (wasting syndrome)
    cancer cell migration,
    cancer cell adhesion,
    cancer cell invasion, and
    cancer cell metastasization.

[127.] The method of any one of embodiments [125]-[126], wherein the pharmaceutical dosage form provides for the time release of the extract or concentrate of *Cannabis*.

[128.] The method of any one of embodiments [125]-[126], wherein the pharmaceutical dosage form provides for the controlled release of the extract or concentrate of *Cannabis*.

[129.] The method of any one of embodiments [125]-[126], wherein the pharmaceutical dosage form provides for the continuous release of the extract or concentrate of *Cannabis*.

[130.] The method of any one of embodiments [125]-[126], wherein the pharmaceutical dosage form provides for the sustained release of the extract or concentrate of *Cannabis*.

[131.] The method of any one of embodiments [125]-[126], wherein the pharmaceutical dosage form provides for the modified release of the extract or concentrate of *Cannabis*.

[132.] The method of any one of embodiments [125]-[126], wherein the pharmaceutical dosage form provides for the immediate release of the extract or concentrate of *Cannabis*.

[133.] The method of any one of embodiments [125]-[126], wherein the pharmaceutical dosage form provides for the extended release of the extract or concentrate of *Cannabis*.

[134.] The method of any one of embodiments [125]-[133], wherein the pharmaceutical dosage form provides for the release of the extract or concentrate of *Cannabis*, over a period of time of about 1 hour to about 24 hours.

[135.] The method of any one of embodiments [125]-[133], wherein the pharmaceutical dosage form provides for the release of the extract or concentrate of *Cannabis*, over a period of time of about 4 hours to about 24 hours.

[136.] The method of any one of embodiments [125]-[133], wherein the pharmaceutical dosage form provides for the release of the extract or concentrate of *Cannabis*, over a period of time of about 6 hours to about 24 hours.

[137.] The method of any one of embodiments [125]-[133], wherein the pharmaceutical dosage form provides for the release of the extract or concentrate of *Cannabis*, over a period of time of about 8 hours to about 24 hours.

[138.] The method of any one of embodiments [125]-[133], wherein the pharmaceutical dosage form provides for the release of the extract or concentrate of *Cannabis*, over a period of time of about 1 hour to about 12 hours.

[139.] The method of any one of embodiments [125]-[133], wherein the pharmaceutical dosage form provides for the release of the extract or concentrate of *Cannabis*, over a period of time of about 2 hours to about 12 hours.

[140.] The method of any one of embodiments [125]-[133], wherein the pharmaceutical dosage form provides for the release of the extract or concentrate of *Cannabis*, over a period of time of about 4 hours to about 12 hours.

[141.] The method of any one of embodiments [125]-[133], wherein the pharmaceutical dosage form provides for the release of the extract or concentrate of *Cannabis*, over a period of time of about 6 hours to about 12 hours.

[142.] The method of any one of embodiments [125]-[133], wherein the pharmaceutical dosage form provides for the release of the extract or concentrate of *Cannabis*, over a period of time of about 1 hour to about 4 hours.

[143.] The method of any one of embodiments [125]-[133], wherein the pharmaceutical dosage form provides for the release of the extract or concentrate of *Cannabis*, over a period of time of about 1 hour to about 2 hours.

[144.] The method of any one of embodiments [125]-[143], wherein the pharmaceutical dosage form is administered up to about 8 times per day.

[145.] The method of any one of embodiments [125]-[143], wherein the pharmaceutical dosage form is administered about 1-4 times per day.

[146.] The method of any one of embodiments [125]-[143], wherein the pharmaceutical dosage form is administered in a single daily dosage, 1 time per day.

The invention claimed is:

1. A process for obtaining a concentrate of *Cannabis sativa* or *Cannabis indica*, the process comprising:
   (a) contacting *Cannabis sativa* or *Cannabis indica* plant material with a supercritical fluid solvent system, at a pressure between about 750 psi and 25,000 psi, and at a temperature between about −15° C. and 200° C., to provide an extract of *Cannabis sativa* or *Cannabis indica*; and
   (b) removing the supercritical fluid solvent system from the extract;
   wherein the (a) contacting of the *Cannabis sativa* or *Cannabis indica* plant material with the supercritical fluid solvent system and the (b) removing the supercritical fluid solvent system, is carried out multiple times, such that the process is a fractional supercritical fluid extraction;
   wherein each contacting of the *Cannabis sativa* or *Cannabis indica* with a supercritical fluid solvent system independently occurs at a pressure between about 750 psi and 25,000 psi, and independently occurs at a temperature between about −15° C. and 200° C.;
   wherein at least one of the supercritical fluid extractions is carried out at a pressure of at least about 8,000 psi; and
   wherein each supercritical fluid solvent system independently comprises carbon dioxide ($CO_2$) and optionally one or more additional solvents and optionally one or more co-solvents, selected from the group consisting of hydrogen ($H_2$), neon (Ne), nitrogen ($N_2$), argon (Ar), methane ($CH_4$), ethane ($CH_3CH_3$), propane ($CH_3CH_2CH_3$), ammonia ($NH_3$), water ($H_2O$), xenon (Xe), methanol, ethanol, 1-propanol, 2-propanol, 1-hexanol, 2-methoxy ethanol, tetrahydrofuran (THF), 1,4-dioxane, acetonitrile, methylene chloride, dichloroethane, chloroform, ethyl acetate, propylene carbonate, N,N-dimethylaceamide, dimethyl sulfoxide (DMSO), formic acid, carbon disulfide, acetone, toluene, hexanes, pentanes, trifluoromethane (Freon® 23), nitrous oxide ($N_2O$), sulfur hexafluoride ($SF_6$), butane (n-$C_4H_{10}$), isobutane (i-$C_4H_{10}$), ethyl ether (($C_2H_5)_2O$), benzotrifluoride ($C_6H_5CF_3$), p-chlorophenyl trifluoromethane ($ClC_6H_4CF_3$), chlorofluorocarbon (CFC), hydrofluorocarbon (HFA), HFA-134a (1,1,1,2-tetrafluoroethane), and mixtures thereof.

2. The process of claim 1, wherein each pressure is independently selected from (i) 750-4,000 psi, (ii) 4,000-7,000 psi, and (iii) 7,000-25,000 psi; with the proviso that at least one of the supercritical fluid extractions is carried out at a pressure of at least about 8,000 psi.

3. The process of claim 1, wherein each temperature is independently selected from (i) −15-70° C., (ii) 70-100° C., and (iii) 100-200° C.

4. The process of claim 1, wherein each fractional supercritical fluid extraction is independently carried out employing a supercritical fluid solvent system which is: (i) polar aprotic, (ii) polar protic, (iii) nonpolar aprotic, or (iv) nonpolar protic.

5. The process of claim 1, wherein the concentrate of *Cannabis sativa* or *Cannabis indica* comprises at least one of:
cannabinol (CBN),
cannabinolic acid (CBNA),
Δ(9)-tetrahydrocannabinol (Δ(9)-THC),
Δ(9)-tetrahydrocannabinolic acid (Δ(9)-THCA),
Δ(9)-cannabidiol (Δ(9)-CBD),
Δ(9)-tetrahydrocannabidiolic acid (Δ(9)-CBDA),
Δ(8)-tetrahydrocannabinol (Δ(8)-THC),
Δ(8)-tetrahydrocannabinolic acid (Δ(8)-THCA),
Δ(8)-tetrahydrocannabidiol (Δ(8)-CBD),
Δ(8)-tetrahydrocannabidiolic acid (Δ(8)-CBDA),
Δ(9)-tetrahydrocannabivarin (Δ(9)-THV),
cannabigerol (CBG),
cannabigerolic acid (CBGA),
cannabichromene (CBC),
cannabichromenic acid (CBCA),
cannabicyclol (CBL),
cannabicyclolic acid (CBLA),
β-caryophyllene epoxide,
mentha-1,8(9)-dien-5-ol,
pulegone,
limonene,
limonene oxide,
α-terpinene,
terpinen-4-ol,
carvacrol,
carvone,
1,8-cineole,
p-cymene,
fenchone,
pulegone-1,2epoxide,
β-myrcene,
cannaflavin A, and
cannaflavin B.

6. The process of claim 1, wherein the concentrate of *Cannabis sativa* or *Cannabis indica*, relative to the *Cannabis sativa* or *Cannabis indica* plant material, is at least partially purified from at least one of terpenes, alkaloids, hemp oil, and cannabinoid acids.

7. The process of claim 1, further comprising purifying the concentrate of *Cannabis sativa* or *Cannabis indica*, employing at least one of chromatography, adsorption, crystallization, distillation, liquid-liquid extraction, filtration, fractional distillation, precipitation, recrystallization, and sublimation.

8. The process of claim 1, wherein the concentrate of *Cannabis sativa* or *Cannabis indica* comprises Δ(9)-tetrahydrocannabinol (Δ(9)-THC).

9. The process of claim 1, wherein the concentrate of *Cannabis sativa* or *Cannabis indica* comprises Δ(9)-tetrahydrocannabinolic acid (Δ(9)-THCA).

10. The process of claim 1, wherein the concentrate of *Cannabis sativa* or *Cannabis indica* comprises Δ(9)-cannabidiol (Δ(9)-CBD).

11. The process of claim 1, wherein the concentrate of *Cannabis sativa* or *Cannabis indica* Δ(9)-tetrahydrocannabidiolic acid (Δ(9)-CBDA).

12. The process of claim 1, wherein the concentrate of *Cannabis sativa* or *Cannabis indica* comprises Δ(8)-tetrahydrocannabinol (Δ(8)-THC).

13. The process of claim 1, wherein the concentrate of *Cannabis sativa* or *Cannabis indica* comprises Δ(8)-tetrahydrocannabinolic acid (Δ(8)-THCA).

14. The process of claim 1, wherein the concentrate of *Cannabis sativa* or *Cannabis indica* comprises Δ(8)-tetrahydrocannabidiol (Δ(8)-CBD).

15. The process of claim 1, wherein the concentrate of *Cannabis sativa* or *Cannabis indica* comprises Δ(8)-tetrahydrocannabidiolic acid (Δ(8)-CBDA).

16. The process of claim 1, wherein the concentrate of *Cannabis sativa* or *Cannabis indica* comprises Δ(9)-tetrahydrocannabivarin (Δ(9)-THV).

17. The process of claim 1, wherein any one or more supercritical fluid solvent system independently comprises an additive selected from the group consisting of methanol, ethanol, 1-propanol, 2-propanol, 1-hexanol, 2-methoxy ethanol, tetrahydrofuran, 1,4-dioxane, acetonitrile, dichloromethane, ammonia, chloroform, propylene carbonate, N,N-dimethylaceamide, dimethyl sulfoxide, formic acid, water, carbon disulfide, acetone, propane, toluene, hexanes, pentanes, $C_6H_5CF_3$, p-$ClC_6H_4CF_3$, and mixtures thereof.

18. The process of claim 1, wherein the first fractional supercritical fluid extraction is carried out with carbon dioxide ($CO_2$) as the sole solvent.

19. The process of claim 1, wherein the second fractional supercritical fluid extraction is carried out with carbon dioxide ($CO_2$) as the sole solvent.

20. The process of claim 1, wherein the first concentrate is enriched with tetrahydrocannabinols (THCs) and the second concentrate is enriched with cannabidiols (CBDs).

* * * * *